United States Patent
Mendez-Perez et al.

(10) Patent No.: US 9,776,991 B2
(45) Date of Patent: Oct. 3, 2017

(54) THIENOMETHYLPIPERAZINE DERIVATIVES AS INHIBITORS OF SOLUBLE EPOXIDE HYDROLASE

(71) Applicant: SANOFI, Paris (FR)

(72) Inventors: Maria Mendez-Perez, Frankfurt am Main (DE); Kristin Breitschopf, Frankfurt am Main (DE); Katrin Lorenz, Frankfurt am Main (DE); Hartmut Strobel, Frankfurt am Main (DE); Li-hsing Wang, Frankfurt am Main (DE); Alexander Schiffer, Frankfurt am Main (DE); Jochen Goerlitzer, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/100,608

(22) PCT Filed: Dec. 2, 2014

(86) PCT No.: PCT/EP2014/076263
§ 371 (c)(1),
(2) Date: May 31, 2016

(87) PCT Pub. No.: WO2015/082474
PCT Pub. Date: Jun. 11, 2015

(65) Prior Publication Data
US 2016/0326146 A1 Nov. 10, 2016

(30) Foreign Application Priority Data

Dec. 4, 2013 (EP) ..................................... 13306663

(51) Int. Cl.
| | |
|---|---|
| *C07D 333/38* | (2006.01) |
| *C07D 409/12* | (2006.01) |
| *C07D 409/14* | (2006.01) |
| *C07D 413/12* | (2006.01) |
| *A61K 31/496* | (2006.01) |
| *C07D 277/56* | (2006.01) |
| *C07D 417/12* | (2006.01) |
| *C07D 417/14* | (2006.01) |
| *C07D 333/48* | (2006.01) |
| *C07D 471/04* | (2006.01) |
| *C07D 487/04* | (2006.01) |

(52) U.S. Cl.
CPC ......... *C07D 409/12* (2013.01); *C07D 277/56* (2013.01); *C07D 333/38* (2013.01); *C07D 333/48* (2013.01); *C07D 409/14* (2013.01); *C07D 413/12* (2013.01); *C07D 417/12* (2013.01); *C07D 417/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 6,162,808 A | 12/2000 | Kindon et al. | |
| 6,933,308 B2 * | 8/2005 | Boy ..................... | C07D 277/56 514/231.5 |

FOREIGN PATENT DOCUMENTS

| | | |
|---|---|---|
| WO | WO-2007/098352 A2 | 8/2007 |
| WO | WO-2007/106525 A1 | 9/2007 |
| WO | WO-2007/138110 A2 | 12/2007 |
| WO | WO-2008/079277 A1 | 7/2008 |
| WO | WO-2010/025179 A1 | 3/2010 |

OTHER PUBLICATIONS

Shen et al. J Med Chem. Mar. 8, 2012; 55(5): 1789-1808.*
Waltenberger et al. J. Chem. Inf. Model. 2016, 56, 747-762.*
De Taeye, B.M. et al. (Mar. 2010). "Expression and Regulation of Soluble Epoxide Hydrolase in Adipose Tissue," *Obesity* 18(3):489-498.
Imig, J. D. et al. (Oct. 2009). "Soluble Epoxide Hydrolase as a Therapeutic Target for Cardiovascular Diseases," *Nat. Rev. Drug Discov.* 8(10):794-805.

(Continued)

*Primary Examiner* — Emily Bernhardt
(74) *Attorney, Agent, or Firm* — Morrison & Foerster LLP

(57) ABSTRACT

The present invention relates to compounds of the formula (I), wherein R1, R2, R3, R4 and X have the meanings indicated in the claims. The compounds of formula I are valuable pharmacologically active compounds. They are highly potent and selective soluble epoxide hydrolase inhibitors and are suitable, for example, for the therapy and prophylaxis of renal failure, diabetic nephropathy, type 2 diabetes mellitus, cardiovascular diseases, inflammatory diseases or could show beneficial effects in pain, dyslipidemia, atherosclerosis wound healing and stroke. The invention furthermore relates to processes for the preparation of compounds of the formula I, their use, in particular as active ingredients in pharmaceuticals, and pharmaceutical preparations comprising them.

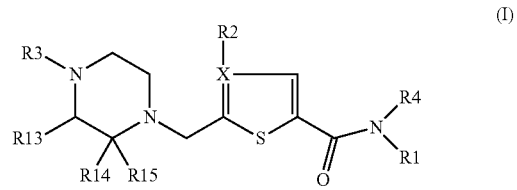

2 Claims, No Drawings

(56) References Cited

OTHER PUBLICATIONS

Jones, P.D. et al. (2005). "Fluorescent Substrates for Soluble Epoxide Hydrolase and Application to Inhibition Studies," *Analytical Biochemistry* 343:66-75.

Kaspera, R. et al. (2009). "Epoxyeicosatrienoic Acids: Formation, Metabolism and Potential Role in Tissue Physiology and Pathophysiology," *Expert Opin. Drug. Metab. Toxicol* 5(7):757-771.

Luo, P. et al. (2010). "Inhibition or Deletion of Soluble Epoxide Hydrolase Prevents Hyperglycemia, Promotes Insulin Secretion, and Reduces Islet Apoptosis," *The Journal of Pharmacology and Experimental Therapeutics* 334(2):430-438.

Montalbetti, C. et al. (2005). "Amide Bond Formation and Peptide Coupling," *Tetrahedron* 61(46):10827-10852.

Monti, J. et al. (May 2008). "Soluble Epoxide Hydrolase is a Susceptibility Factor for Heart Failure in a Rat Model of Human Disease," *Nature Genetics* 40(5):529-537.

Mustafa, S. et al. (2009). "Insulin Resistance and Endothelial Dysfunction: Are Epoxyeicosatrienoic Acids the Link?," *Exp. Clin. Cardiol.* 14(2):e41-e50.

Olearczyk, J. J. et al. (Jan. 2009). "Administration of a Substituted Adamantly-urea Inhibitor of Soluble Epoxide Hydrolase Protects the Kidney from Damage in Hypertensive Goto-Kakizaki Rats," *Clinical Science* 116(1):61-70.

Valeur, E. et al. (2009, e-pub. Dec. 2008). "Amide Bond Formation: Beyond the Myth of Coupling Reagents," *Chemical Society Reviews* 38:606-631.

Wuts, P.G.M. et al. (2006). "Protection for the Amino Group," Chapter 7 in *Greens Protective Groups in Organic Synthesis*, 4th Edition, John Wiley &Sons, Inc., pp. 706-926.

International Preliminary Report on Patentability and Written Opinion mailed Jun. 7, 2016 for PCT Application No. PCT/EP2014/076263, filed Dec. 2, 2014, five pages.

International Search Report mailed Feb. 9, 2015 for PCT Application No. PCT/EP2014/076263, filed Dec. 2, 2014, three pages.

Written Opinion of the International Searching Authority mailed Feb. 9, 2015, for PCT Application No. PCT/EP2014/076263, filed Dec. 2, 2014, four pages.

\* cited by examiner

THIENOMETHYLPIPERAZINE DERIVATIVES AS INHIBITORS OF SOLUBLE EPOXIDE HYDROLASE

CROSS REFERENCE TO RELATED APPLICATIONS

This application is a National Phase application under 35 U.S.C. §371 of International Application No. PCT/EP2014/076263 filed Dec. 2, 2014, which claims priority benefit to EP Application No. 13306663.9 filed Dec. 4, 2013, the disclosures of each of which are herein incorporated by reference in their entirety.

The present invention relates to compounds of the formula I,

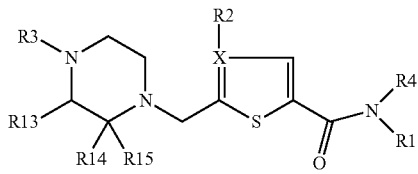

wherein R1, R2, R3, R4 and X have the meanings indicated below. The compounds of formula I are valuable pharmacologically active compounds. They are highly potent and selective soluble epoxide hydrolase inhibitors and are suitable, for example, for the therapy and prophylaxis of renal failure, diabetic nephropathy, type 2 diabetes mellitus, cardiovascular diseases, inflammatory diseases or could show beneficial effects in pain, dyslipidemia, atherosclerosis wound healing and stroke. The invention furthermore relates to processes for the preparation of compounds of the formula I, their use, in particular as active ingredients in pharmaceuticals, and pharmaceutical preparations comprising them.

The soluble epoxide hydrolase in the following sEH, is operating within the arachidonic and the linoleic acid pathway and plays an important role in the metabolism of these physiologically important signalling molecules. sEH hydrolyzes the CYP-P450-derived epoxy-metabolites of the n-6 polyunsaturated fatty acids (epoxyeicosatrienoic acids, EETs; epoxy-octadecenoic acids, EpOMEs) into the corresponding vicinal diols (dihydroxyeicosatrienoic acids, DHETs; and dihydroxyoctadecenoic acids, DiHOMEs). Whereas the biological function of EpOMES remains largely unknown, EETs biological function has been intensively studied over the last years. EETs formation and action is deeply integrated into various physiological processes and exerts numerous, beneficial biological functions. EETs play a critical role in the regulation of vascular, renal and cardiovascular function (R. Kaspera et al., *Expert Opin. Drug. Metab. Toxicol.* 2009, 5, 757-771). Important new fields emerging may include a role of CYP-derived epoxyeicosanoids in insulin secretion, in the mediation of inflammatory or anti-inflammatory processes and in pain (S. Mustafa et al., *Exp. Clin. Cardiol.* 2009, 14, e41-50).

Numerous data from the literature support the beneficial effect of sEH inhibition (J. D. Imig and B. D. Hammock, *Nat. Rev. Drug Discov.* 2009, 8, 794-805). Inhibition of the sEH by specific inhibitors in various animal models of hypertension (SHR rats, AngII-induced hypertension, salt-sensitive hypertension) reduces blood pressure, provides renal protection and decreases plasma levels of pro-inflammatory cytokines. For instance, sEH inhibitors attenuate AngII- and transverse aortic constriction (TAC)-induced hypertrophy, cardiac fibrosis and cardiac NF-κB activation in mice. In addition, sEH inhibitors ameliorate AngII-induced atherosclerosis in ApoE KO mice. In a rat model of human disease, sEH has been shown to be a susceptibility factor for heart failure (J. Monti et al., Nat. Genet. 2008, 40, 529-537).

Furthermore, protection from kidney damage is observed in hypertensive, diabetic Goto-Kakizaki rat model independent of blood pressure lowering (J. J. Olearczyk et al., *Clinical Science* 2009, 116, 61-70). Further on, it was shown that total adipose sEH activity is higher in obese vs. lean mice and is supposed to influence lipid metabolism, adipogenesis or local inflammation (B. M. De Taeye et al., *Obesity* 2010, 18, 489-498). Moreover, EETs might be involved in mediating stimulus-induced secretion of insulin from pancreatic islets. In diabetic mice, glucose tolerance is improved by sEH inhibition (P. Luo et al., *J. Pharm. Exp. Ther.* 2010, 334, 430-438).

It can therefore be concluded, that inhibition of sEH by a specific small molecule inhibitor will stabilize CYP-P450 produced epoxides of polyunsaturated fatty acids resulting in protective effects in diabetes and diabetes-associated co-morbidities including inflammation, renal and cardiac function, and pain.

Thus, the present invention relates to compounds of the formula I,

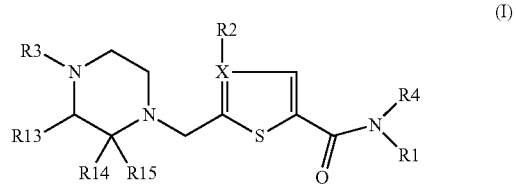

wherein
R1 is —($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R5,
—($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R6, or
—($C_1$-$C_6$)-alkyl,
R2 is hydrogen atom or —($C_1$-$C_4$)-alkyl,
R3 is -aryl, wherein aryl is an aromatic hydrocarbon radical containing from 6 to 14 carbon atoms depending on the number of carbon atoms in one, two or three rings, and wherein aryl is mono-, di- or trisubstituted independently of one another by R9,
—C(O)-aryl, wherein aryl is an aromatic hydrocarbon radical containing from 6 to 14 carbon atoms depending on the number of carbon atoms in one, two or three rings, and wherein aryl is mono-, di- or trisubstituted independently of one another by R11, —C(O)—($C_1$-$C_4$)-alkylene-aryl, wherein aryl is defined above and wherein aryl is mono-, di- or trisubstituted independently of one another by R9, —C(O)—($C_1$-$C_4$)-alkylene-O-aryl, wherein aryl is defined above and wherein aryl is mono-, di- or trisubstituted independently of one another by R11, —C(O)-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R8, —C(O)—($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R8, -heteroaryl, wherein heteroaryl is selected out of the group 1,1-dioxo-tetrahydro-1-thiophenyl, imidazolyl, morpholinyl, oxadiazolyl, piperazinyl, piperidinyl, pyrazinyl, pyridazinyl, pyridyl, pyrimidinyl, pyrrolidinyl, tetrahydrofuranyl, tetrazolyl, thiazolyl, thiodiazolyl, thiophenyl, and triazolyl, and wherein said heteroaryl is unsubstituted or mono-, di- or trisubstituted independently of one another by R12, —C(O)—($C_1$-$C_4$)-alkylene-R7, wherein said alkylene is unsubstituted or mono-, di- or trisubstituted independently of one another by R7, —C(O)—($C_1$-$C_4$)-alkylene-S—R18, wherein said alkylene is unsubstituted or mono-, di- or trisubstituted independently of one another by R7, —C(O)—($C_1$-$C_3$)-alkylene-O—($C_1$-$C_3$)-alkylene-O—($C_1$-$C_3$)-alkyl, —C(O)—($C_3$-$C_8$)-cycloalkyl, wherein said cycloalkyl is unsubstituted or mono-, di- or trisubstituted independently of one another by R10, —($C_3$-$C_8$)-cycloalkyl, wherein said cycloalkyl is unsubstituted or mono-, di- or trisubstituted independently of one another by R10, —($C_1$-$C_3$)-fluoroalkyl, or —($C_1$-$C_4$)-alkyl-R7, wherein said alkyl is unsubstituted or mono-, di- or trisubstituted independently of one another by R7, or R3 together with the nitrogen atom to which it is bonded and R13 together with the carbon atom to which they are bonded form together a five- to eight-membered monocyclic heterocyclic ring which, as well as the nitrogen atom, may additionally, according to the ring size, also contain one or two identical or different heteroatoms from the group of oxygen, nitrogen and sulfur, and wherein said five- to eight-membered monocyclic heterocyclic ring is unsubstituted or mono-, di- or trisubstituted independently of one another by =O, —($C_1$-$C_4$)-alkyl or halogen, X is carbon atom or nitrogen atom, R4, R5, R6, R7, R9, R10, and R11 are independent of one another are identical or different and are a hydrogen atom, —($C_1$-$C_4$)-alkyl, —OH, —($C_1$-$C_4$)-alkyl-OH, —$NH_2$, —N(R16)-R17, halogen, —($C_1$-$C_3$)-fluoroalkyl, —O—($C_1$-$C_4$)-alkyl, —CN, —O—($C_1$-$C_3$)-fluoroalkyl, —($C_1$-$C_3$)-alkylene-O—($C_1$-$C_3$)-alkyl, or phenyl, R8 and R12 are independent of one another are identical or different and are a hydrogen atom, =O, —($C_1$-$C_4$)-alkyl, —OH, —($C_1$-$C_4$)-alkyl-OH, halogen, —$NH_2$, —($C_1$-$C_3$)-fluoroalkyl, —O—($C_1$-$C_4$)-alkyl, —CN, —O—($C_1$-$C_3$)-fluoroalkyl, —N(R16)-R17, —C(O)—NH—($C_1$-$C_4$)-alkyl, —($C_1$-$C_3$)-alkylene-O—($C_1$-$C_3$)-alkyl, or phenyl, R13 is hydrogen atom, —($C_1$-$C_4$)-alkyl, =O, or halogen and R14, R15, R16, R17, and R18 are independent of one another are identical or different and are a hydrogen atom, or —($C_1$-$C_4$)-alkyl, in all its stereoisomeric forms and mixtures thereof in any ratio, and its physiologically tolerable salts.

2) Thus, the present invention also relates to compounds of the formula I, wherein R1 is —($C_1$-$C_4$)-alkylene-aryl, wherein aryl is selected out of the group phenyl, tetrahydronaphthalenyl, naphthyl, biphenylyl, anthryl, indanyl, bicyclo[4.2.0]octa-1(6),2,4-trienyl, and fluorenyl, and wherein said alkylene or aryl are independently from each other mono-, di- or trisubstituted independently of one another by R5, —($C_1$-$C_4$)-alkylene-heterocyclyl, wherein heterocyclyl is acridinyl, azaindole (1H-pyrrolopyridinyl), azabenzimidazolyl, azaspirodecanyl, azepinyl, azetidinyl, aziridinyl, benzimidazolyl, 2,3-dihydro-benzofuranyl, 2,3-dihydro-benzo[1,4]dioxinyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2-a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanely, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, 6H-pyranyl, pyrazinyl, pyrazolidinyl, pyrazolinyl, pyrazolyl, pyrazolo[1,5-a]pyridinyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyran, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2, 3-triazolyl, 1,2,3-triazolyl, 1,2,4-triazolyl, 1,2,5-triazolyl, 1,3,4-triazolyl and xanthenyl, and wherein said alkylene or heterocyclyl are independently from each other unsubstituted or mono-, di- or trisubstituted independently of one another by R6, or —($C_1$-$C_6$)-alkyl, R2 is hydrogen atom or —($C_1$-$C_4$)-alkyl, R3 is -aryl, wherein aryl is aryl is selected out of the group phenyl, biphenylyl, tetrahydronaphthalenyl, naphthyl, anthryl, indanyl, bicyclo[4.2.0]octa-1 (6),2,4-trienyl, and fluorenyl, and wherein aryl is mono-, di- or trisubstituted independently of one another by R9,
- —C(O)-aryl, wherein aryl is phenyl, biphenylyl, tetrahydronaphthalenyl, naphthyl, anthryl, indanyl, bicyclo [4.2.0]octa-1 (6),2,4-trienyl, and fluorenyl, and wherein aryl is mono-, di- or trisubstituted independently of one another by R11,
- —C(O)—($C_1$-$C_4$)-alkylene-aryl, wherein aryl is defined above and wherein aryl is mono-, di- or trisubstituted independently of one another by R9,
- —C(O)—($C_1$-$C_4$)-alkylene-O-aryl, wherein aryl is defined above and wherein aryl is mono-, di- or trisubstituted independently of one another by R11, —C(O)-heterocyclyl, wherein heterocyclyl is acridinyl, azaindole (1H-pyrrolopyridinyl), azabenzimidazolyl, azaspirodecanyl, azepinyl, azetidinyl, aziridinyl, benzimidazolyl, 2,3-dihydro-benzofuranyl, 2,3-dihydrobenzo[1,4]dioxinyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2-a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanely, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, 6H-pyranyl, pyrazinyl, pyrazolidinyl, pyrazolinyl, pyrazolyl, pyrazolo[1,5-a]pyridinyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bipyridinyl, tetrahydro-isoquinolinyl, tetrahydroquinolinyl, tetrahydrofuranyl, tetrahydro-pyranyl, tetrahydropyridinyl, tetrahydrothiophenyl, tetrahydrothiophenyl-1,1-dioxide, tetrahydrothiopyran, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R8,
- —C(O)—($C_1$-$C_4$)-alkylene-heterocyclyl, wherein heterocyclyl is defined above for —C(O)-heterocyclyl, and wherein said heterocyclyl is unsubstituted or mono-, di- or trisubstituted independently of one another by R8,
- -heteroaryl, wherein heteroaryl is selected out of the group 1,1-dioxo-tetrahydro-1-thiophenyl, imidazolyl, morpholinyl, oxadiazolyl, piperazinyl, piperidinyl, pyrazinyl, pyridazinyl, pyridyl, pyrimidinyl, pyrrolidinyl, tetrahydrofuranyl, tetrazolyl, thiazolyl, thiodiazolyl, thiophenyl, and triazolyl,
  and wherein said heteroaryl is unsubstituted or mono-, di- or trisubstituted independently of one another by R12,
- —C(O)—($C_1$-$C_4$)-alkylene-R7, wherein said alkylene is unsubstituted or mono-, di- or trisubstituted independently of one another by R7,
- —C(O)—($C_1$-$C_4$)-alkylene-S—R18, wherein said alkylene is unsubstituted or mono-, di- or trisubstituted independently of one another by R7,
- —C(O)—($C_1$-$C_3$)-alkylene-O—($C_1$-$C_3$)-alkylene-O—($C_1$-$C_3$)-alkyl,
- —C(O)—($C_3$-$C_8$)-cycloalkyl, wherein said cycloalkyl is unsubstituted or mono-, di- or trisubstituted independently of one another by R10,
- —($C_3$-$C_8$)-cycloalkyl, wherein said cycloalkyl is unsubstituted or mono-, di- or trisubstituted independently of one another by R10,
- —($C_1$-$C_3$)-fluoroalkyl, or
- —($C_1$-$C_4$)-alkyl-R7, wherein said alkyl is unsubstituted or mono-, di- or trisubstituted independently of one another by R7, or R3 together with the nitrogen atom to which it is bonded and R13 together with the carbon atom to which they are bonded form together a monocyclic heterocyclic ring which is selected out of the group azepanyl, azepinyl, dioxazolyl, dioxazinyl, 1,4-diazapanyl, 1,2-diazepinyl, 1,3-diazepinyl, 1,4-diazepinyle, imidazolyl, imidazolinyl, imidazolidinyl, isothiazolyl, isothiazolidinyl, isothiazolinyl, isoxazolyl, isoxazolinyl, isoxazolidinyl, 2-isoxazolinyl, morpholinyl, [1,4]oxazepanyl, oxazolyl, piperazinyl, piperidinyl, pyrazinyl, pyrazolyl, pyrazolinyl, pyrazolidinyl, pyridazinyl, pyridyl, pyrimidinyl, pyrrolyl, pyrrolidinyl, pyrrolidinonyl, pyrrolinyl, tetrahydropyridinyl, tetrazinyl, tetrazolyl, thiazolyl, thiadiazolyl, thiazolidinyl, thiazolinyl, thiomorpholinyl, 1,2,3-triazinyl, 1,2,4-triazinyl, 1,3,5-triazinyl, 1,2,3-triazolyl and 1,2,4-triazolyl, and wherein said monocyclic heterocyclic ring is unsubstituted or mono-, di- or trisubstituted independently of one another by =O, —($C_1$-$C_4$)-alkyl or halogen, X is carbon atom or nitrogen atom, R4, R5, R6, R7, R9, R10, and R11 are independent of one another are identical or different and are a hydrogen atom, —($C_1$-$C_4$)-alkyl, —OH, —($C_1$-$C_4$)-alkyl-OH, —$NH_2$, —N(R16)-R17, halogen, —($C_1$-$C_3$)-fluoroalkyl, —O—($C_1$-$C_4$)-alkyl, —CN, —O—($C_1$-$C_3$)-fluoroalkyl, —($C_1$-$C_3$)-alkylene-O—($C_1$-$C_3$)-alkyl, or phenyl, R8 and R12 are independent of one another are identical or different and are a hydrogen atom, =O, —($C_1$-$C_4$)-alkyl, —OH, —($C_1$-$C_4$)-alkyl-OH, halogen, —$NH_2$, —($C_1$-$C_3$)-fluoroalkyl, —O—($C_1$-$C_4$)-alkyl, —CN, —O—($C_1$-$C_3$)- fluoroalkyl, —N(R16)-R17, —C(O)—NH—($C_1$-$C_4$)-alkyl, —($C_1$-$C_3$)-alkylene-O—($C_1$-$C_3$)-alkyl, or phenyl, R13 is hydrogen atom, —($C_1$-$C_4$)-alkyl, =O, or halogen and R14, R15, R16, R17, and R18 are independent of one another are identical or different and are a hydrogen atom, or —($C_1$-$C_4$)-alkyl, in all its stereoisomeric forms and mixtures thereof in any ratio, and its physiologically tolerable salts.

3) Thus, the present invention also relates to compounds of the formula I, wherein R1 is —($C_1$-$C_4$)-alkylene-aryl, wherein aryl is phenyl, indanyl, or bicyclo[4.2.0]octa-1(6),2,4-trienyl, and wherein said alkylene or aryl are independently from each other mono-, di- or trisubstituted independently of one another by R5, —($C_1$-$C_4$)-alkylene-heterocyclyl, wherein heterocyclyl is benzofuranyl, 2,3-dihydro-benzo[1,4]dioxinyl, 1,4-dioxanyl, imidazo[1,2-a]-pyridyl, isoquinolinyl, isoxazolyl, morpholinyl, oxazolidinyl, pyranyl, 6H-pyranyl, pyrazolyl, pyrazolo[1,5-a]pyridinyl, pyridyl, pyrimidinyl, pyrrolidinyl, pyrrolyl, tetrahydrofuranyl, tetrahydro-pyranyl, thiazolidinyl, or thiophenyl, and wherein said alkylene or heterocyclyl are independently from each other unsubstituted or mono-, di- or trisubstituted independently of one another by R6, or —($C_1$-$C_6$)-alkyl, R2 is hydrogen atom or —($C_1$-$C_4$)-alkyl, R3 is -aryl, wherein aryl is aryl is selected out of the group phenyl, indanyl, or bicyclo[4.2.0]octa-1(6),2,4-trienyl, and wherein aryl is mono-, di- or trisubstituted independently of one another by R9,
—C(O)-aryl, wherein aryl is phenyl, indanyl, or bicyclo[4.2.0]octa-1(6),2,4-trienyl, and wherein aryl is mono-, di- or trisubstituted independently of one another by R11,
—C(O)—($C_1$-$C_4$)-alkylene-aryl, wherein aryl is defined above and wherein aryl is mono-, di- or trisubstituted independently of one another by R9,
—C(O)—($C_1$-$C_4$)-alkylene-O-aryl, wherein aryl is defined above and wherein aryl is mono-, di- or trisubstituted independently of one another by R11,
—C(O)-heterocyclyl, wherein heterocyclyl is benzofuranyl, 2,3-dihydro-benzo[1,4]dioxinyl, 1,4-dioxanyl, imidazolidinyl, imidazo[1,2-a]-pyridyl, isoquinolinyl, isoxazolyl, morpholinyl, oxazolidinyl, oxetanyl, piperidinyl, pyranyl, 6H-pyranyl, pyrazolyl, pyrazolo[1,5-a]pyridinyl, pyridyl, pyrimidinyl, pyrrolidinyl, pyrrolyl, tetrahydrofuranyl, tetrahydro-pyranyl, thiazolidinyl, or thiophenyl, and wherein said heterocyclyl is unsubstituted or mono-, di- or trisubstituted independently of one another by R8,
—C(O)—($C_1$-$C_4$)-alkylene-heterocyclyl, wherein heterocyclyl is defined above for —C(O)-heterocyclyl, and wherein said heterocyclyl is unsubstituted or mono-, di- or trisubstituted independently of one another by R8,
-heteroaryl, wherein heteroaryl is selected out of the group 1,1-dioxo-tetrahydro-1-thiophenyl, imidazolyl, pyrazinyl, pyridazinyl, pyridyl, pyrimidinyl, thiazolyl, or thiodiazolyl, and wherein said heteroaryl is unsubstituted or mono-, di- or trisubstituted independently of one another by R12,
—C(O)—($C_1$-$C_4$)-alkylene-R7, wherein said alkylene is unsubstituted or mono-, di- or trisubstituted independently of one another by R7,
—C(O)—($C_1$-$C_4$)-alkylene-S—R18, wherein said alkylene is unsubstituted or mono-, di- or trisubstituted independently of one another by R7,
—C(O)—($C_1$-$C_3$)-alkylene-O—($C_1$-$C_3$)-alkylene-O—($C_1$-$C_3$)-alkyl,
—C(O)—($C_3$-$C_8$)-cycloalkyl, wherein said cycloalkyl is unsubstituted or mono-, di- or trisubstituted independently of one another by R10,
—($C_3$-$C_8$)-cycloalkyl, wherein said cycloalkyl is unsubstituted or mono-, di- or trisubstituted independently of one another by R10,
—($C_1$-$C_3$)-fluoroalkyl, or
—($C_1$-$C_4$)-alkyl-R7, wherein said alkyl is unsubstituted or mono-, di- or trisubstituted independently of one another by R7, or R3 together with the nitrogen atom to which it is bonded and R13 together with the carbon atom to which they are bonded form together a pyrrolyl or 1,2,4-triazolyl,
and wherein said monocyclic heterocyclic ring is unsubstituted or mono-, di- or trisubstituted independently of one another by =O, —($C_1$-$C_4$)-alkyl or halogen, X is carbon atom or nitrogen atom, R4 is hydrogen atom, R5, R6, R7, R9, R10, and R11 are independent of one another are identical or different and are a hydrogen atom, —($C_1$-$C_4$)-alkyl, —OH, —($C_1$-$C_4$)-alkyl-OH, —NH$_2$, —N(R16)-R17, halogen, —($C_1$-$C_3$)-fluoroalkyl, —O—($C_1$-$C_4$)-alkyl, —CN, —O—($C_1$-$C_3$)-fluoroalkyl, —($C_1$-$C_3$)-alkylene-O—($C_1$-$C_3$)-alkyl, or phenyl, R8 and R12 are independent of one another are identical or different and are a hydrogen atom, =O, —($C_1$-$C_4$)-alkyl, —OH, —($C_1$-$C_4$)-alkyl-OH, halogen, —NH$_2$, —($C_1$-$C_3$)-fluoroalkyl, —O—($C_1$-$C_4$)-alkyl, —CN, —O—($C_1$-$C_3$)-fluoroalkyl, —N(R16)-R17, —C(O)—NH—($C_1$-$C_4$)-alkyl, —($C_1$-$C_3$)-alkylene-O—($C_1$-$C_3$)-alkyl, or phenyl, R13 is hydrogen atom, —($C_1$-$C_4$)-alkyl, =O, or halogen and R14, R15, R16, R17, and R18 are independent of one another are identical or different and are a hydrogen atom, or —($C_1$-$C_4$)-alkyl, in all its stereoisomeric forms and mixtures thereof in any ratio, and its physiologically tolerable salts.

4) Thus, the present invention also relates to compounds of the formula I, wherein R1 is —($C_1$-$C_4$)-alkylene-aryl, wherein aryl is phenyl or indanyl, and wherein said alkylene or aryl are independently from each other mono-, or disubstituted independently of one another by R5,
—($C_1$-$C_4$)-alkylene-heterocyclyl, wherein heterocyclyl is 2,3-dihydro-benzo[1,4]dioxinyl, pyrazolyl, or pyridyl, and wherein said alkylene or heterocyclyl are independently from each other unsubstituted or mono- or, disubstituted independently of one another by R6, or —($C_1$-$C_6$)-alkyl, R2 is hydrogen atom or —($C_1$-$C_4$)-alkyl, R3 is -aryl, wherein aryl is aryl is selected out of the group phenyl, or bicyclo[4.2.0]octa-1(6),2,4-trienyl, and wherein aryl is mono- or disubstituted independently of one another by R9,
—C(O)-aryl, wherein aryl is phenyl, or bicyclo[4.2.0]octa-1(6),2,4-trienyl, and wherein aryl is mono- or disubstituted independently of one another by R11,
—C(O)—($C_1$-$C_4$)-alkylene-aryl, wherein aryl is defined above and wherein aryl is mono- or disubstituted independently of one another by R9,
—C(O)—($C_1$-$C_4$)-alkylene-O-aryl, wherein aryl is defined above and wherein aryl is mono- or disubstituted independently of one another by R11,
—C(O)-heterocyclyl, wherein heterocyclyl is benzofuranyl, 1,4-dioxanyl, imidazolidinyl, imidazo[1,2-a]- pyridyl, isoquinolinyl, isoxazolyl, morpholinyl, oxetanyl, piperidinyl, pyranyl, 6H-pyranyl, pyrazolyl, pyrazolo[1,5-a]pyridinyl, pyridyl, pyrimidinyl, pyrrolidinyl, pyrrolyl, tetrahydrofuranyl, tetrahydro-pyranyl, thiazolidinyl, or thiophenyl, and wherein said heterocyclyl is unsubstituted or mono-, di- or trisubstituted independently of one another by R8,
—C(O)—($C_1$-$C_4$)-alkylene-heterocyclyl, wherein heterocyclyl is oxazolidinyl, pyrrolidinyl or, isoxazolyl, and wherein said heterocyclyl is unsubstituted or monosubstituted by R8,
-heteroaryl, wherein heteroaryl is selected out of the group 1,1-dioxo-tetrahydro-1-thiophenyl, imidazolyl, pyrazinyl, pyridazinyl, pyridyl, pyrimidinyl, thiazolyl, or thiodiazolyl, and wherein said heteroaryl is unsubstituted or mono- or disubstituted independently of one another by R12,
—C(O)—($C_1$-$C_4$)-alkylene-R7, wherein said alkylene is unsubstituted or mono- or disubstituted independently of one another by R7,
—C(O)—($C_1$-$C_4$)-alkylene-S—R18,
—C(O)—($C_1$-$C_3$)-alkylene-O—($C_1$-$C_3$)-alkylene-O—($C_1$-$C_3$)-alkyl,
—C(O)—($C_3$-$C_8$)-cycloalkyl, wherein said cycloalkyl is unsubstituted or monosubstituted by R10,
—($C_3$-$C_8$)-cycloalkyl, wherein said cycloalkyl is unsubstituted or monosubstituted by R10,
—($C_1$-$C_3$)-fluoroalkyl, or
—($C_1$-$C_4$)-alkyl-R7, wherein said alkyl is unsubstituted or monosubstituted by R7, or
R3 together with the nitrogen atom to which it is bonded and R13 together with the carbon atom to which they are bonded form together a pyrrolyl or 1,2,4-triazolyl, and wherein said monocyclic heterocyclic ring is unsubstituted or monosubstituted by =O or —($C_1$-$C_4$)-alkyl,
X is carbon atom,
R4 is hydrogen atom,
R5, R6, R7, R9, R10, and R11 are independent of one another are identical or different and are a hydrogen atom, —($C_1$-$C_4$)-alkyl, —OH, —$NH_2$, —N(R16)-R17, F, Cl, Br, —($C_1$-$C_3$)-fluoroalkyl, —O—($C_1$-$C_4$)-alkyl, —O—($C_1$-$C_3$)-fluoroalkyl, —($C_1$-$C_3$)-alkylene-O—($C_1$-$C_3$)-alkyl, or phenyl,
R8 and R12 are independent of one another are identical or different and are a hydrogen atom, =O, —($C_1$-$C_4$)-alkyl, —OH, —($C_1$-$C_4$)-alkyl-OH, F, Cl, Br, —($C_1$-$C_3$)-fluoroalkyl, —O—($C_1$-$C_4$)-alkyl, —C(O)—NH—($C_1$-$C_4$)-alkyl, or —($C_1$-$C_3$)-alkylene-O—($C_1$-$C_3$)-alkyl,
R13 is hydrogen atom, or =O, and
R14, R15, R16, R17, and R18 are independent of one another are identical or different and are a hydrogen atom or methyl,
in all its stereoisomeric forms and mixtures thereof in any ratio, and its physiologically tolerable salts.

5) Thus, the present invention also relates to compounds of the formula I, wherein
R1 is —($C_1$-$C_4$)-alkylene-aryl, wherein aryl is phenyl or indanyl, and wherein said alkylene or aryl are independently from each other mono-, or disubstituted independently of one another by R5,
—($C_1$-$C_4$)-alkylene-heterocyclyl, wherein heterocyclyl is 2,3-dihydro-benzo[1,4]dioxinyl, pyrazolyl, or pyridyl, and wherein said alkylene or heterocyclyl are independently from each other unsubstituted or mono- or, disubstituted independently of one another by R6, or
—($C_1$-$C_6$)-alkyl, R2 is hydrogen atom or —($C_1$-$C_4$)-alkyl,
R3 is —C(O)-aryl, wherein aryl is phenyl, or bicyclo[4.2.0]octa-1(6),2,4-trienyl, and wherein aryl is mono- or disubstituted independently of one another by R11,
—C(O)—($C_1$-$C_4$)-alkylene-aryl, wherein aryl is defined above and wherein aryl is mono- or disubstituted independently of one another by R9,
—C(O)—($C_1$-$C_4$)-alkylene-O-aryl, wherein aryl is defined above and wherein aryl is mono- or disubstituted independently of one another by R11,
—C(O)-heterocyclyl, wherein heterocyclyl is benzofuranyl, 1,4-dioxanyl, imidazolidinyl, imidazo[1,2-a]pyridyl, isoquinolinyl, isoxazolyl, morpholinyl, oxetanyl, piperidinyl, pyranyl, 6H-pyranyl, pyrazolyl, pyrazolo[1,5-a]pyridinyl, pyridyl, pyrimidinyl, pyrrolidinyl, pyrrolyl, tetrahydrofuranyl, tetrahydro-pyranyl, thiazolidinyl, or thiophenyl, and wherein said heterocyclyl is unsubstituted or mono-, di- or trisubstituted independently of one another by R8,
—C(O)—($C_1$-$C_4$)-alkylene-heterocyclyl, wherein heterocyclyl is oxazolidinyl, pyrrolidinyl or, isoxazolyl, and wherein said heterocyclyl is unsubstituted or monosubstituted by R8,
—C(O)—($C_1$-$C_4$)-alkylene-R7, wherein said alkylene is unsubstituted or mono- or disubstituted independently of one another by R7,
—C(O)—($C_1$-$C_4$)-alkylene-S—R18,
—C(O)—($C_1$-$C_3$)-alkylene-O—($C_1$-$C_3$)-alkylene-O—($C_1$-$C_3$)-alkyl,
—C(O)—($C_3$-$C_8$)-cycloalkyl, wherein said cycloalkyl is unsubstituted or monosubstituted by R10,
X is carbon atom,
R4 is hydrogen atom,
R5, R6, R7, R9, R10, and R11 are independent of one another are identical or different and are a hydrogen atom, —($C_1$-$C_4$)-alkyl, —OH, —$NH_2$, —N(R16)-R17, F, Cl, Br, —($C_1$-$C_3$)-fluoroalkyl, —O—($C_1$-$C_4$)-alkyl, —O—($C_1$-$C_3$)-fluoroalkyl, —($C_1$-$C_3$)-alkylene-O—($C_1$-$C_3$)-alkyl, or phenyl,
R8 and R12 are independent of one another are identical or different and are a hydrogen atom, =O, —($C_1$-$C_4$)-alkyl, —OH, —($C_1$-$C_4$)-alkyl-OH, F, Cl, Br, —($C_1$-$C_3$)-fluoroalkyl, —O—($C_1$-$C_4$)-alkyl, —C(O)—NH—($C_1$-$C_4$)-alkyl, or —($C_1$-$C_3$)-alkylene-O—($C_1$-$C_3$)-alkyl,
R13 is hydrogen atom, or =O, and
R16, R17, and R18 are independent of one another are identical or different and are a hydrogen atom or methyl,
in all its stereoisomeric forms and mixtures thereof in any ratio, and its physiologically tolerable salts.

6) The present invention also relates to compounds of the formula I and/or in all its stereoisomeric forms and mixtures thereof in any ratio, and/or a physiologically acceptable salt of the compound of the formula I, where the compound of the formula I is selected from the group consisting of
5-[4-((R)-2-Hydroxy-3-methyl-butyryl)-piperazin-1-ylmethyl]-thiophene-2-carboxylic acid (2-methoxy-pyridin-4-ylmethyl)-amide,
5-[4-(2-Hydroxy-propionyl)-piperazin-1-ylmethyl]-thiophene-2-carboxylic acid 2-trifluoromethoxy-benzylamide,
5-[4-(2,4-Dimethyl-6-oxo-6H-pyran-3-carbonyl)-piperazin-1-ylmethyl]-thiophene-2-carboxylic acid 4-chloro-2-fluoro-benzylamide,
5-[4-(1-Amino-cyclopropanecarbonyl)-piperazin-1-ylmethyl]-thiophene-2-carboxylic acid 2-trifluoromethoxy-benzylamide,
5-[4-(2,6-Dimethyl-pyridin-4-yl)-piperazin-1-ylmethyl]-thiophene-2-carboxylic acid 2,4-dichloro-benzylamide, 5-[4-(3,5-Dimethyl-1H-pyrazole-4-carbonyl)-piperazin-1-ylmethyl]-thiophene-2-carboxylic acid (2-methoxy-pyridin-4-ylmethyl)-amide, 5-[4-(3,6-Difluoro-pyridine-2-carbonyl)-piperazin-1-ylmethyl]-thiophene-2-carboxylic acid (2-methoxy-pyridin-4-ylmethyl)-amide or 2-[4-(2-Dimethylamino-propionyl)-piperazin-1-ylmethyl]-thiazole-5-carboxylic acid 2,4-dichloro-benzylamide.

As used herein, the term alkyl is to be understood in the broadest sense to mean hydrocarbon residues which can be linear, i. e. straight-chain or branched. All these statements also apply if an alkyl group occurs as a substituent on another residue, for example in an alkyloxy residue, an alkyloxycarbonyl residue or an arylalkyl residue. Examples of "—($C_1$-$C_4$)-alkyl" or "—($C_1$-$C_4$)-alkylene" are alkyl residues containing 1, 2, 3 or 4 carbon atoms which are methyl, methylene, ethyl, ethylene, propyl, propylene, butyl, or butylene, or the n-isomers of all these residues, or isopropyl, isobutyl, sec-butyl, tert-butyl.

Examples of "—($C_1$-$C_6$)-alkyl" are alkyl residues containing 1, 2, 3, 4, 5 or 6, carbon atoms which are methyl, ethyl, propyl, butyl, pentyl, hexyl, the n-isomers of all these residues, or isopropyl, isobutyl, 1-methylbutyl, isopentyl, neopentyl, 2,2-dimethylbutyl, 2-methylpentyl, 3-methylpentyl, isohexyl, secondary-butyl, tertiary-butyl, tertiary-pentyl, secondary-butyl.

The term "—($C_3$-$C_8$)-cycloalkyl" is understood as meaning cyclic alkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The term "aryl" is understood as meaning aromatic hydrocarbon radicals containing from 6 to 14 carbon atoms depending on the number of carbon atoms in one, two or three rings. Examples of aryl radicals are group phenyl, tetrahydronaphthalenyl, naphthyl, biphenylyl, anthryl, indanyl, bicyclo[4.2.0]octa-1(6),2,4-trienyl, and fluorenyl for example 2-biphenylyl, 3-biphenylyl and 4-biphenylyl, anthryl or fluorenyl. Biphenylyl radicals, naphthyl radicals and, in particular, phenyl and bicyclo[4.2.0]octa-1(6),2,4-trienyl, radicals are preferred aryl radicals.

The term "-heterocyclyl" refers to a ring system containing 4 to 15 ring carbon atoms, wherein depending on the ring size one, two, three or four of the 4 to 15 ring carbon atoms are independently replaced by nitrogen, oxygen or sulfur atoms. Examples are acridinyl, azaindole (1H-pyrrolopyridinyl), azabenzimidazolyl, azaspirodecanyl, azepinyl, azetidinyl, aziridinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2-a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1] heptanely, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, 6H-pyranyl, pyrazinyl, pyrazolidinyl, pyrazolinyl, pyrazolyl, pyrazolo[1,5-a]pyridinyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydro-pyranyl, tetrahydropyridinyl, tetrahydrothiophenyl, tetrahydrothiophenyl-1,1-dioxide, tetrahydrothiopyran, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "=O" refers to residues such as carbonyl (—C(O)—), sulfinyl (—S(O)—) or nitroso (—N=O). The term "=O" preferably refers to carbonyl (—C(O)—).

The term "R3 together with the nitrogen atom to which it is bonded and R13 together with the carbon atom to which they it is bonded form together a five- to eight-membered monocyclic heterocyclic ring which, as well as the nitrogen atom, may additionally, according to the ring size, also contain one or two identical or different heteroatoms from the group of oxygen, nitrogen and sulfur" is understood to mean radicals such as azepane, azepine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term R20-(CO)— means those R3 groups for formula I, which have a —(CO)— group; so R20-(CO)— is e.g. —C(O)-aryl, —C(O)—($C_1$-$C_4$)-alkylene-aryl, —C(O)—($C_1$-$C_4$)-alkylene-O-aryl, —C(O)-heterocyclyl, —C(O)—($C_1$-$C_4$)-alkylene-heterocyclyl, —C(O)—($C_1$-$C_4$)-alkylene-R7, —C(O)—($C_1$-$C_4$)-alkylene-S—R18, —C(O)—($C_1$-$C_3$)-alkylene-O—($C_1$-$C_3$)-alkylene-O—($C_1$-$C_3$)-alkyl or —C(O)—($C_3$-$C_8$)-cycloalkyl.

The term "—($C_1$-$C_3$)-fluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—

$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine, bromine or fluorine.

The present invention also relates to processes for the preparation of the compounds of the formula I which are outlined below and by which the compounds of the formula I and intermediates occurring in the course of their synthesis are obtainable. The following schemes are provided to more fully illustrate the present invention.

Representative compounds of formula I have been prepared by the reaction schemes below. It is understood that other synthetic approaches to these structural classes are conceivable to one skilled in the art. It is within the abilities of a person skilled in the art to replace the exemplary compounds shown in the schemes and exemplary reagent given in the text by appropriate alternative compounds or reagents or to omit or add synthetic steps when appropriate.

All such reactions, which can be used in the preparation of the compounds of the formula I, are known per se and can be carried out in a manner familiar to a person skilled in the art according to procedures which are described in the standard literature.

General Scheme for all Transformations

If the compounds of formula I comprise one or more acidic or basic groups, for example basic heterocyclic groups, the corresponding physiologically or toxicologically acceptable salts are also included in the invention, especially the pharmaceutically acceptable salts. The compounds of formula I may thus be deprotonated on an acidic group and be used for example as alkali metal salts or as ammonium salts. Compounds of formula I comprising at least one basic group may also be prepared and used in the form of their acid addition salts, for example in the form of pharmaceutically acceptable salts with inorganic acids and organic acids. Salts can in general be prepared from acidic and basic compounds of formula I by a reaction with a base or an acid in a solvent or diluent according to customary procedures. If the compounds of formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

Salts of compounds of formula I can be obtained by customary s known to those skilled in the art, for example by combining a compound of the formula I with an inorganic or organic acid or base in a solvent or dispersant, or from other salts by cation exchange or anion exchange. The present invention furthermore includes all solvates of compounds of the formula I for example hydrates or adducts with alcohols. The compounds of the formula I can be prepared by utilizing procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by analogous procedures described in this application.

The present invention also relates to processes for the preparation of the compounds of the formula I which are outlined below and by which the compounds of the formula I as well as intermediates occurring in the course of their synthesis are obtainable. The preparation of compounds of formula I is outlined below. The following schemes are provided to more fully illustrate the present invention. Representative compounds of formula I have been prepared by the reaction schemes below. It is understood that other synthetic approaches to these structural classes are conceivable to one skilled in the art. It is within the abilities of a person skilled in the art to replace the exemplary compounds shown in the schemes and exemplary reagents described in the Examples by appropriate alternative compounds or to omit or add process steps when appropriate.

The various organic group transformations and utilization of protecting groups described herein can be performed by a number of procedures other than those illustrated below, which are familiar to a person skilled in the art In general, compounds of formula I can be prepared, for example in the course of a convergent synthesis, by linking two or more fragments which can be derived retro synthetically from the formula I.

The invention also relates to a process for preparing a compound of formula I

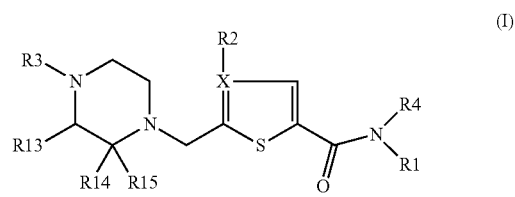

(I)

and/or a physiologically tolerated salt of the compound of formula I which comprises a) linking a compound of formula II, or any suitable salt thereof, with a compound of formula III

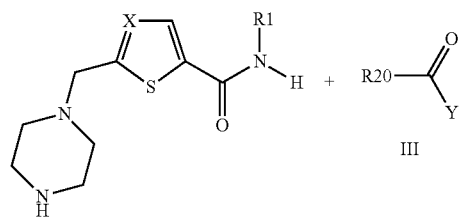

wherein X and R1 are as defined for formula I, R20-(CO)— is as defined in those R3 groups for formula I, which have a —(CO)— group, and Y is OH or Cl to form a compound of formula I or b) linking the compound of formula IV with a compound of formula V

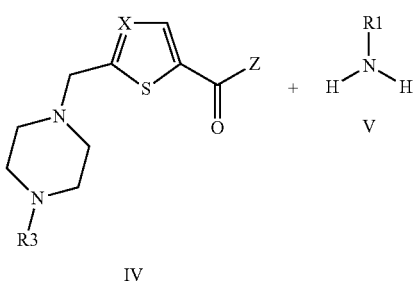

IV wherein X, R1 and R2 are as defined for formula I and Z is OH or Cl to form a compound of formula I or
c) linking the compound of formula VI with a compound of formula VII using a suitable hydride equivalent, such as a cyanoboronhydride,

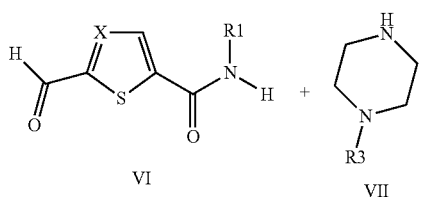

VI   VII wherein X, R1 and R2 are as defined for formula I to form a compound of formula I, or d) fractionating the compound of the formula I, which has been prepared by processes a), b) or c), which, owing to its chemical structure, occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers obtained in this way, and elimination of the chiral auxiliary groups, into the pure enantiomers or diastereomers; or e) either isolating the compound of the formula I prepared by processes a) to d) in free form or liberating it from non-physiologically acceptable salts or, in the case where acidic or basic groups are present, converting it into a physiologically acceptable salt.

Compounds of the formula I can be prepared retro synthetically by coupling building blocks as shown in the following reaction scheme I:

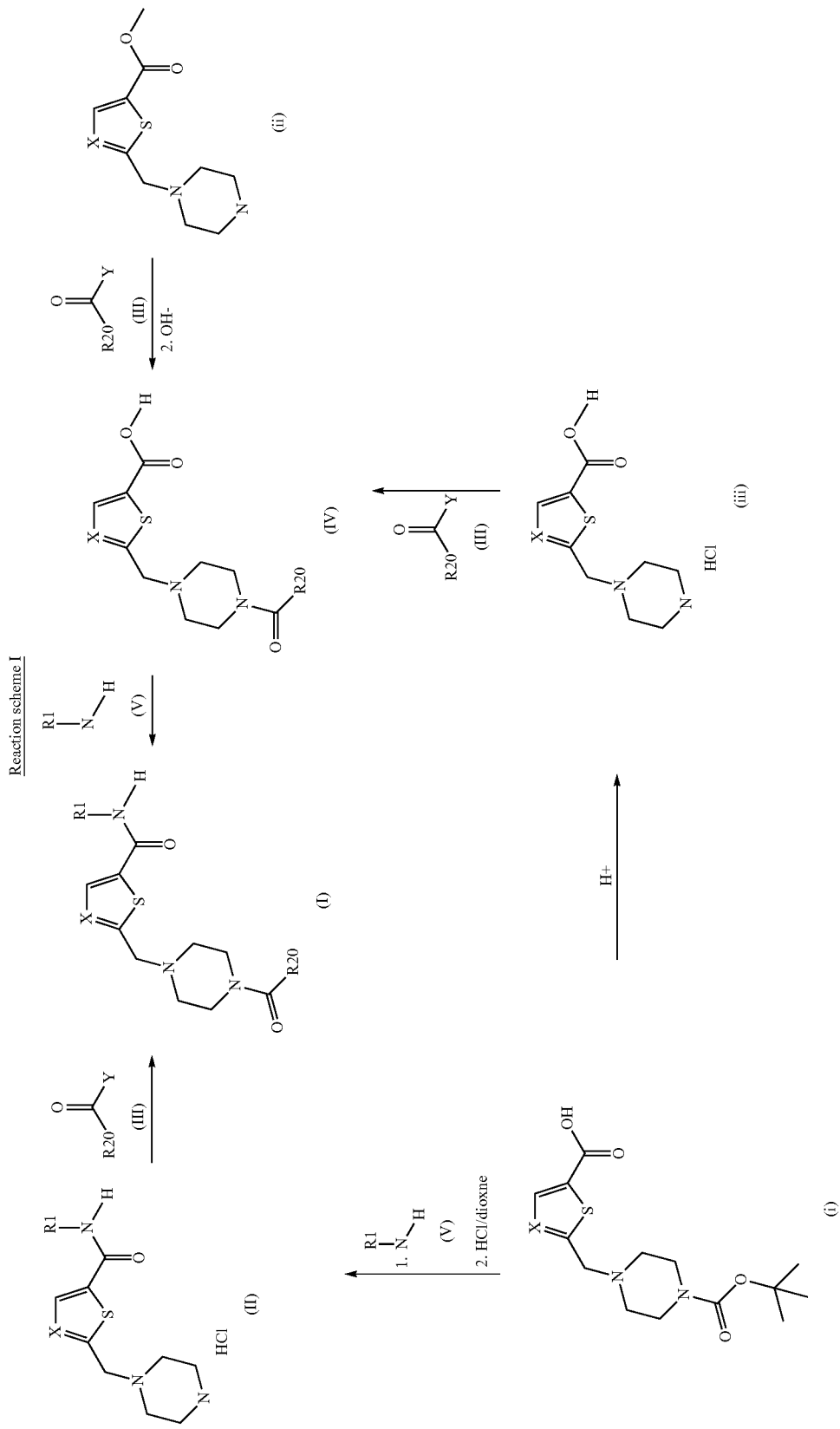
Reaction scheme I

A compound of formula I can be prepared, for example, starting with 4-(5-carboxy-thiophen-2-ylmethyl)-piperazine-1-carboxylic acid tert-butyl ester, which is an example of an intermediate (IV), wherein X is a carbon atom (see reaction scheme I). 4-(5-Carboxy-thiophen-2-ylmethyl)-piperazine-1-carboxylic acid tert-butyl ester can be prepared as described in WO2008079277, p 145, and can be transformed to a suitably derivative building block as described in reaction scheme I which are intermediates (II) or (IV). Said intermediates (II) or (IV) can be prepared by a variety of synthetic procedures known to a person skilled in the art.

The preparation of intermediate (II) involves the coupling of 4-(5-Carboxy-thiophen-2-ylmethyl)-piperazine-1-carboxylic acid tert-butyl ester (see intermediate (i) in reaction scheme I) with an amine following standard coupling procedures as described in e.g. C. Montalbetti, et al., Tetrahedron 2005, 61, 10827-10852; or E. Valeur, et al., Chemical Society Reviews 2009, 38, 606-631, and then deprotection of the t-butoxycarbonyl amino function by processes known to a person skilled in the art or described e.g. in P. G. M. Wuts and T. W. Greene, Greens Protective Groups in Organic Synthesis, 4th Edition (2006) John Wiley & Sons, pages 725-735.

An example of such a coupling procedure is the reaction of 4-(5-Carboxy-thiophen-2-ylmethyl)-piperazine-1-carboxylic acid tert-butyl ester with an amine using a coupling agent such as EDC and an additive such as HOBt or Oxymapure® in an appropriate solvent such as DMF or EtOAc at temperatures between 0° C. to 80° C. and in the presence of a base such as triethylamine or 4-methylmorpholine to render an intermediate (II), which can be purified by extraction or chromatography previous to deprotection of the boc group. For the deprotection of the boc group many synthetic procedures can be chosen e.g. treatment with a suitable acid such as trifluoroacetic acid or hydrochloric acid, without or in an appropriate solvent such as tetrahydrofurane, dioxane or dichloromethane at a suitable temperature.

Intermediate (II) or its corresponding salts are coupled with intermediate (III) (see reaction scheme I), which can be carboxylic acid or suitable activated derivatives thereof such as acid chlorides or imidazoyl derivatives by synthetic procedures known to a person skilled in the art. An example of such a coupling reaction is e.g. the coupling of an acid chloride, with intermediate (II) in the presence of an appropriate base such as triethylamine, or pyridine in an appropriate solvent such as THF or dichloromethane to prepare a compound of formula I.

Alternatively, intermediate (II) can be coupled with carboxylic acids in the presence of a coupling agent such as EDC, and an additive such as HOBt or Oxymapure® in the presence of a suitable base such as Hünig's base or 4-methylmorpholine without an appropriate solvent or in the presence of an appropriate solvent such as DMF or EtOAc.

In a further process intermediate (IV) can be prepared from 4-(5-Carboxy-thiophen-2-ylmethyl)-piperazine-1-carboxylic acid tert-butyl ester by initial deprotection of the t-butoxycarbonyl amino moiety by a process known to a person skilled in the art or described in e.g. in P. G. M. Wuts and T. W. Greene, Greens Protective Groups in Organic Synthesis, 4th Edition (2006) John Wiley & Sons, pages 725-735, to prepare an intermediate (iii) (see reaction scheme I). Intermediate (iii) or its corresponding salts are coupled with intermediate (III) (see reaction scheme I), which can be carboxylic acid or suitable activated derivatives thereof such as an acid chloride in a suitable solvent such as dichloromethane or tetrahydrofurane in the presence of an appropriate base such as Hünig's base or potassium carbonate, can be effected with or without previous reaction of intermediate (iii) with BSA. Converting intermediate (IV) to a compound of the formula I can be done by using a suitable coupling as described in C. Montalbetti, et al., Tetrahedron 2005, 61, 10827-10852. Coupling of intermediate (IV) with the corresponding amines of intermediate (V) (see reaction scheme I). can be done using the appropriate coupling agents such as EDC and HOBt or Oxymapure® in the presence of a suitable base such as Hünig's base or 4-methylmorpholine and in a suitable solvent such as DMF or EtOAc. In a further process step intermediate (IV) can be converted into its acid chloride by synthetic procedures known to a person skilled in the art such as the use of oxallyl chloride or N,N-dimethylchloropropenylamine which can be coupled to the corresponding amine intermediate (V) in the presence of a suitable base such as Hünig's base in a suitable solvent such as dichloromethane or tetrahydrofurane at a suitable temperature.

Alternatively, a compound of formula I can be prepared, for example, starting with 2-piperazin-1-ylmethyl-thiazole-5-carboxylic acid methyl ester, which is an example of a compound of formula (ii), wherein X is a nitrogen atom (see reaction scheme I). 2-piperazin-1-ylmethyl-thiazole-5-carboxylic acid methyl ester can be prepared from 2-bromomethyl-thiazole-5-carboxylic acid methyl ester (prepared as described in U.S. Pat. No. 6,162,808, page 14) and N-tert-butyloxycarbonylpiperazine by synthetic procedure similar to those described in WO2010025179, page 15. Intermediate (ii) or its corresponding salts are coupled with intermediate (III) (see reaction scheme I), which can be carboxylic acid or suitable activated derivatives thereof such as acid chlorides or imidazoyl derivatives by synthetic procedures known to a person skilled in the art or as described e.g. in C. Montalbetti, et al., Tetrahedron 2005, 61, 10827-10852 or E. Valeur, et al., Chemical Society Reviews 2009, 38, 606-631.

An example of such a coupling procedure is the reaction of intermediate (ii) with a carboxylic acid in the presence of EDC and an additive such as HOBt or Oxymapure® in the presence of a suitable base such as triethylamine or 4-methylmorpholine and in a suitable solvent such as EtOAc or DMF at temperatures between RT and 100° C. In a further process intermediate (ii) can be reacted with the corresponding acid chloride or imidazole (which are commercially available or easily prepared by known methods) in the presence of a suitable base such as triethylamine, potassium carbonate, or 4-methyl morpholine and most generally in an aprotic solvent such as THF or dichloromethane, and at temperatures ranging from 0° C. to 100° C. The compounds obtained can be transformed in intermediate (IV) by hydrolysis or the ester functionality by standard synthetic procedures known to a person skilled in the art, such as treatment of the carboxylic esters with a OH⁻ source such as NaOH or LiOH in an appropriate solvent such as THF:water mixtures and at temperatures from RT to 100° C. Intermediate (i) is commercially available or can be prepared by synthetic procedures known to a person skilled in the art.

A compound of the formula I can be prepared retro synthetically by coupling building blocks as shown in the following reaction scheme II:

Reaction scheme II

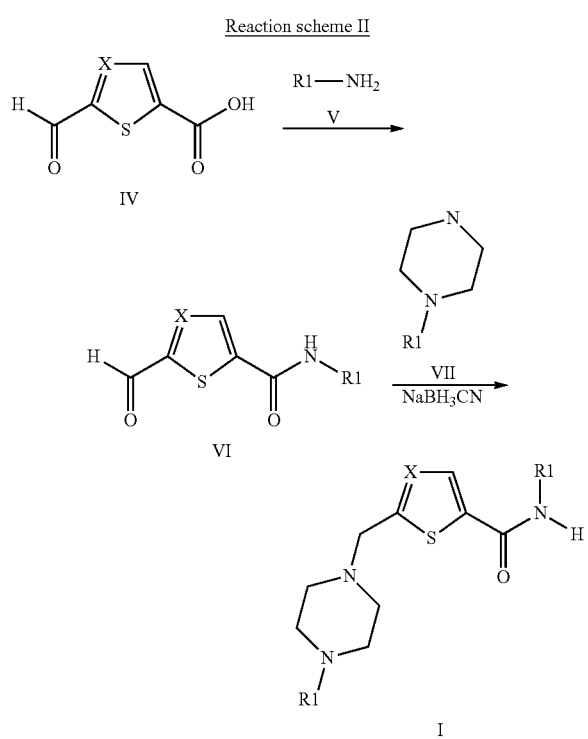

Compounds of formula I can be prepared from a suitable 2-formyl-thiazole-5-carboxylic acid or 2-formyl-thiophene-5-carboxylic acid, which are commercially available or can be made from commercially available starting materials and can be modified to a suitable compound of formula (VI) by a wide variety of synthetic procedures known to a person skilled in the art.

An example of such a coupling procedure is the reaction of the compound of formula IV with a compound of formula V under reaction conditions described in C. Montalbetti, et al., Tetrahedron 2005, 61, 10827-10852. An alternative coupling process is the treatment of a compound of formula IV with coupling reagents such as EDC in the presence of a suitable additive such as HOBt or Oxymapure® and a suitable base such as Hünig's base or 4-methylmorpholine in a suitable solvent such as DMF or EtOAc and at temperatures from about 0° C. to 100° C. The compounds of formula VI obtained can be treated with a compound of formula VII in the presence of a reducing agent such as sodium cyanoboronhydride or triacetoxyboronhydride at an appropriate pH and in an appropriate protic or aprotic solvent such MeOH or THF, with or without the presence of a suitable acid such as acetic acid at temperatures from about 0° C. to about 100° C. to give compounds of the formula I. In a further process step compounds of formula IV can be converted to their corresponding acid chlorides, by synthetic procedures known to a person skilled in the art such as treatment with oxallyl chloride and catalytic amounts of DMF in a suitable solvent such as dichloromethane or tetrahydrofurane at temperatures from 0° C. to about 80° C. or by treatment with N-dimethyl chloropropanylamine in an appropriate solvent such as dichloromethane or tetrahydrofurane at temperatures from 0° C. to about 80° C. Acid chlorides obtained by this way can be coupled with a compound of formula V by a variety of synthetic procedures known to a person skilled in the art. This reaction works best in aprotic solvents such as pyridine, dichloromethane or tetrahydrofurane with addition of a base such as triethylamine, Hünig's base, N-methylmorpholine or potassium carbonate and at temperatures from 0° C. to 100° C.

In general, protective groups that may still be present in the products obtained in the coupling reactions can be removed by standard procedures. For example, tert-butyl protecting groups, in particular a tert-butoxycarbonyl group, which is a protection form of an amino group, can be deprotected, i. e. converted into the amino group, by treatment with trifluoroacetic acid. After the coupling reaction other functional groups can be generated from suitable precursor groups.

In the preparation of the compounds of the formula I it can generally be advantageous or necessary in all reactions which are carried out in the course of the synthesis, to temporarily protect functional groups, which could lead to undesired reactions or side reactions in a synthesis step, or have them initially present in the form of precursor groups, and later deprotect them or convert them into the desired groups. Appropriate synthesis strategies and protective groups and precursor groups which are suitable for the respective case, are known to the person skilled in the art or can be found in P. G. M. Wuts and T. W. Greene, Greens Protective Groups in Organic Synthesis, 4th Edition (2006) John Wiley & Sons. Protecting groups that can be present on functional groups include allyl, tert.-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for amino and amidino groups. Ester, alkyl, aryl and silyl protecting groups can be used to block hydroxyl groups. Carboxylic acids can be protected as esters for example methyl-, ethyl- or benzyl-ester.

Protecting groups that can still be present in the products are then removed by standard procedures. In more detail, examples of protective groups which may be mentioned, are benzyl protective groups, for example benzyl ethers of hydroxyl compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with strong acids (e.g. hydrochloric acid, trifluoroacetic acid), acyl protective groups, for example ester and amides of hydroxyl compounds and amino compounds, which can be cleaved by treatment with strong bases (e.g. LiOH, NaOH, KOH) or strong acids (e.g. HCl) in the presence of water, alkoxycarbonyl protective groups, for example tert-butoxycarbonyl derivatives of amino compounds, which can be cleaved by treatment with strong acids (e.g. hydrochloric acid, trifluoroacetic acid), or benzyloxycarbonyl derivatives of amino compounds, which can be cleaved by catalytic hydrogenation in the presence of a palladium catalyst. Other examples of precursors are halogen atoms which can be replaced by many other groups as outlined above, or nitro groups which can be converted into amino groups, for example by catalytic hydrogenation.

As is usual and applies to all reactions performed in the course of the synthesis of a compound of formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of formula I and their intermediates, and adaptations have to be made.

In all processes for the preparation of the compounds of formula I, workup of the reaction mixture and the purification of the product is performed according to customary synthetic procedures known to a person skilled in the art, which include, quenching of a reaction mixture with water, adjustment to a certain pH, precipitation, extraction, drying, concentration, distillation, crystallization and chromatography including high performance liquid chromatography (HPLC), reversed phase-high performance liquid chromatography (RP-HPLC) and super critical fluid chromatography (SFC) or other s of separation based, for example, on the size, charge or hydrophobicity of the compound. The compounds of formula I are characterized by customary s e.g. NMR, IR and mass spectroscopy (MS).

The compounds of formula I can be isolated either in free form or, in the case of the presence of acidic or basic groups, converted into physiologically tolerable salts. Salts obtained by the processes described above can be converted into the corresponding free base by either subjecting them to ion exchange chromatography or for example by alkaline aqueous treatment and subsequent extraction with suitable organic solvents e.g. methyl tert. butyl ether, chloroform, ethyl acetate or isopropanol/dichloromethane mixtures and subsequent evaporation to dryness. The preparation of physiologically tolerable salts of compounds of formula I capable of salt formation, including their stereoisomeric forms, is carried out in a manner known per se. If the compounds of the formula I contain basic groups, stable acid addition salts can be prepared using strong acids e.g. both inorganic and organic acids such as hydrochloric, p-toluenesulfonic, or trifluoroacetic acid.

The compounds of the present invention are soluble epoxide hydrolase inhibitors. They are specific hydrolase inhibitors inasmuch as they do not substantially inhibit the activity of other hydrolases whose inhibition is not desired. The activity of the compounds of the formula I can be determined, for example, in the assays described below or in other assays known to those skilled in the art. With respect to soluble epoxide hydrolase inhibition, a preferred embodiment of the invention comprises compounds which have a $K_i < 1$ µM for soluble epoxide hydrolase inhibition as determined in the assays described below and which preferably do not substantially inhibit the activity of other hydrolases.

As inhibitors of soluble epoxide hydrolase the compounds of formula I and their physiologically tolerable salts are generally suitable for the therapy and prophylaxis of conditions in which the activity of soluble epoxide hydrolase plays a role or has an undesired extent, or which can favorably be influenced by inhibiting soluble epoxide hydrolase or decreasing their activity, or for the prevention, alleviation or cure of which an inhibition of soluble epoxide hydrolase or a decrease in their activity is desired by the physician.

The soluble epoxide hydrolase inhibitors according to the invention are generally suitable for treating hypertension, AngII-induced hypertension, salt-sensitive hypertension, for reducing blood pressure, for providing renal protection and for decreasing plasma levels of pro-inflammatory cytokines. Furthermore, the soluble epoxide hydrolase inhibitors according to the invention are also suitable for attenuating AngII- and TAC-induced hypertrophy or cardiac fibrosis. In addition, soluble epoxide hydrolase inhibitors according to the invention are suitable for improving glucose tolerance in diabetes mellitus or type 2 diabetes mellitus. Furthermore, soluble epoxide hydrolase inhibitors according to the invention are suitable for protecting kidney damage, especially in patients having diabetes mellitus or type 2 diabetes mellitus patients.

Important new fields emerging may include a role of CYP-derived epoxyeicosanoids in insulin secretion, in the mediation of inflammatory or anti-inflammatory processes and in pain.

The invention also relates to the treatment of disease states such as pain, inflammatory disease, atherosclerosis, coronary artery disease, aortic aneurysm, diabetes mellitus, diabetic complications like diabetic nephropathy, retinopathy, neuropathy, insulin resistance, renal failure/renal disease, peripheral vascular disease, vascular disease, cardiovascular disease including hypertension, cardiac failure, myocardial infarction, ischemic heart disease, angina, obesity, lipid metabolism disorder, peripheral vascular disease, stroke, chronic obstructive pulmonary disease, and wound healing.

The compounds of formula I and/or physiologically compatible salts thereof can also be used for the treatment and prevention of disorders where sEH requires only partial inhibition, for example by using a lower dosage.

The compounds of formula I and/or their pharmaceutically acceptable salts can be employed to produce medicaments with a sEH inhibitory effect for the therapy and prophylaxis of hypertension and organ failure or damage including maladaptive cardiac hypertrophy, heart failure, and liver failure, cardiac and renal fibrosis.

The compounds of formula I and/or their pharmaceutically acceptable salts are further suitable for producing a medicament for the therapy or prophylaxis of ischemic limb disease, endothelial dysfunction, erectile dysfunction, diabetic nephropathy, diabetic vasculopathy and diabetic retinopathy.

The compounds of formula I and/or their pharmaceutically acceptable salts are further suitable for producing a medicament for the therapy or prevention of atherothrombotic disorders including coronary artery disease, coronary vasospasm, myocardial ischemia, and hyperlipidemia/lipid metabolism disorder.

sEH is indirectly involved in the regulation of platelet function through its EETs. Thus, compounds of the invention are further suitable for the inhibition of platelet aggregation which is believed to decrease the risk of atherthrombotic events.

The compounds of formula I and/or their pharmaceutically acceptable salts are further suitable for producing a medicament for the therapy or prophylaxis of metabolic disorders including insulin resistance and diabetes-associated disorders (e.g. diabetic retinopathy, diabetic nephropathy, diabetic neuropathy and diabetic wound healing). The compounds of the formula I and/or their pharmaceutically acceptable salts are further suitable for producing a medicament for the therapy or prevention of inflammatory disorders including arthritis, inflammatory pain, overactive bladder, asthma, and chronic obstructive pulmonary disease.

The compounds of formula I and their physiologically tolerable salts can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenteral, for example intravenously, intramuscularly or subcutaneously, in the form of injection solutions or infusion solutions, microcapsules, implants or rods, or percutaneous or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of formula I and/or its (their) physiologically tolerable salts. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of formula I and/or their physiologically tolerable salts and/or their prodrugs. The amount of the active ingredient of formula I and/or its physiologically tolerable salts and/or its prodrugs in the pharmaceutical preparations normally is from about 0.5 mg to about 1000 mg, preferably from about 1 mg to about 500 mg.

In addition to the active ingredients of formula I and/or their physiologically acceptable salts and to carrier substances, the pharmaceutical preparations can contain additives such as, for example, fillers, disintegrates, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of formula I and/or their physiologically tolerable salts. In case a pharmaceutical preparation contains two or more compounds of formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of formula I allow a great deal of control over the biological and physico-chemical properties of the compounds and thus allows the selection of such desired compounds. Furthermore, in addition to at least one compound of formula I and/or a physiologically tolerable salt, the pharmaceutical preparations can also contain one or more other therapeutically or prophylactically active ingredients.

When using the compounds of formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Further, the compounds of formula I can be used as synthesis intermediates for the preparation of other compounds, in particular of other pharmaceutical active ingredients, which are obtainable from the compounds of formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. Those with skill in the art will readily understand that known variations of the conditions and processes described in the examples can be used to synthesize the compounds of the present invention. When in the final step of the synthesis of a compound an acid such as trifluoroacetic acid or hydrochloric acid was used, for example when trifluoroacetic acid was employed to remove a tert-butyl group, or when an example compounds containing a basic group were purified by preparative high performance liquid chromatography (HPLC) on reversed phase (RP) column material and, as customary, the eluent was a gradient mixture of water and acetonitrile containing trifluoroacetic acid, they were, depending on the details of the work-up procedure such as evaporation or lyophilization conditions, obtained partially or completely in the form of a salt of the acid used, for example in the form of the trifluoroacetic acid salt or hydrochloric acid salt.

It is understood that modifications that do not substantially affect the activity of the various embodiments of this invention are included within the invention disclosed herein. Accordingly, the following examples are intended to illustrate but not limit the present invention.

EXAMPLES

The prepared compounds were in general characterized by spectroscopic data and chromatographic data, in particular mass spectra and HPLC retention times (Rt; in min) which were obtained by combined analytical HPLC/MS characterization (LC/MS), and/or nuclear magnetic resonance (NMR) spectra. Unless specified otherwise, 1H-NMR spectra were recorded at 500 MHz in D6-dimethyl sulfoxide as solvent at RT or 300 MHz in CDCl$_3$ as solvent at RT. In the NMR characterization, the chemical shift δ (in ppm), the number of hydrogen atoms (H) and the multiplicity (s: singlet, d: doublet, t: triplet, m: multiplet) of the peaks are given. In the MS characterization, in general the detected mass number (m/z) of the peak of the molecular ion (M), for example (M+), or of a related ion such as the ion (M+1), for example (M+1+), i.e. the protonated molecular ion [M+H]+ (MH+), or the ion (M−1), for example (M−1)−, i.e. the deprotonated molecular ion [M−H]−, which was formed depending on the ionization used, is given. The particulars of the LC/MS s used are as follows. Unless specified otherwise, the MS ionization was electrospray ionization ES+LC/MS spectra were recorded according to the following methods:

Method 1: column: Waters UPLC BEH C18, 2.1×50 mm; 1.7 μM
solvent: H$_2$O+0.1% TFA:ACN+0.08% TFA (flow 0.9 ml/min)
gradient: 95:5 (0 min) to 5:95 (1.1 min) to 5:95 (1.7 min) to 95:5 (1.8 min) to 95:5 (2 min)

Method 2: column: Waters UPLC BEH C18, 2.1×50 mm; 1.7 μM
solvent: H$_2$O+0.05% TFA:ACN+0.035% TFA (flow 0.9 ml/min)
gradient: 95:5 (0 min) to 5:95 (1.1 min) to 5:95 (1.7 min) to 95:5 (1.8 min) to 95:5 (2 min)

Method 3: column: Waters UPLC BEH C18 2.1×50 mm; 1.7 μM,
solvent: H$_2$O+0.05% TFA:ACN+0.035% TFA (flow 0.9 ml/min)
gradient: 98:2 (0 min) to 5:95 (2.6 min) to 95:5 (2.7 min) to 95:5 (3 min)

Method 4: column: Waters XBridge C18, 4.6×50 mm; 2.5 μM
solvent: H$_2$O+0.1% TFA:ACN+0.1% FA (flow 1.3 ml/min)
gradient: 97:3 (0 min) to 40:60 (3.5 min) to 2:98 (4 min) to 2:98 (5 min) to 97:3 (5.2 min) to 97:3 (6.5 min)

Method 5: column: Luna C18, 10×2.0 mm; 3 μM
solvent: H$_2$O+0.05% TFA:ACN (flow 1.1 ml/min)
gradient: 99:1 (0 min) to 93:7 (1.0 min) to 5:95 (1.8 min) to 99:1 (1.85 min)]

Method 6: column: Waters UPLC BEH C18, 2.1×50 mm; 1.7 μM
solvent: H$_2$O+0.05% TFA:ACN+0.035% TFA (flow 0.9 ml/min)
gradient: 98:2 (0 min) to 5:95 (2 min) to 5:95 (2.6 min) to 95:5 (2.7 min) to 95:5 (3 min)

List of Abbreviations
ACN acetonitrile
BSA Bis(trimethylsilyl)acetamide
Boc tert-butyloxycarbonyl
DMAP 4-(Dimethylamino)-pyridine
DMF dimethylformamide
EDC 1-Ethyl-3-(3-dimethylaminopropyl)carbodiimide
e.g. for example
EtOAc ethyl acetate
HOBt 1-Hydroxybenzotriazole
HPLC high performance liquid chromatography
Hünig's base N,N-Diisopropylethylamine
MeOH methanol
MS mass spectra
NMM 4-Methylmorpholine
NMR nuclear magnetic resonance
PG protecting group
RP-HPLC reversed phase high performance liquid chromatography
RT room temperature (20° C. to 25° C.)
SFC supercritical fluid chromatography
TBS tert-butyldimethylsilyl
TBAF tetrabutylammoniumflouride
THF tetrahydrofuran
TFA trifluoroacetic acid TOTU O-(Cyano(ethoxycarbonyl)methylenamino)-1,1,3,3-tetramethyluronium tetrafluoroborate Synthesis Intermediates Intermediate 1:
5-Piperazin-1-ylmethyl-thiophene-2-carboxylic acid 2-trifluoromethoxy-benzylamide hydrochloride

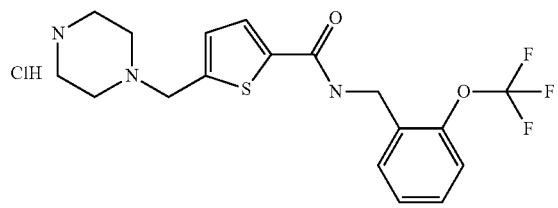 [SMILES: Cl ; O=C(NCc1ccccc1OC(F)(F)F)c1ccc(CN2CCNCC2)s1]

To a solution of 4-(5-Carboxy-thiophen-2-ylmethyl)-piperazine-1-carboxylic acid tert-butyl ester (4 g, 13.0 mmol), HOBt (1.9 gr, 14.3 mmol), 2-trifluoromethoxybenzylamine (2.7 g, 13.6 mmol) and NMM (3.9 g, 38.9 mmol) in DMF (20 ml), ECD*HCl was added (2.6 gr, 13.6 mmol). The mixture was stirred at RT, until conversion to product was observed (about 3 h). Then it was diluted with EtOAc and washed with water. The organic layer was then washed with diluted HCl (2×) and then with brine. The organic layer was dried over MgSO4 and the solvent was evaporated to give 4-[5-(2-trifluoromethoxy-benzylcarbamoyl)-thiophen-2-ylmethyl]-piperazine-1-carboxylic acid tert-butyl ester. The crude material was stirred at RT in 4 M HCl in dioxane (20 mL) for 2 hr. The formed solid was filtered off and dried, to give 5-piperazin-1-ylmethyl-thiophene-2-carboxylic acid 2-trifluoromethoxy-benzylamide (5.4 gr, 96%). 1H NMR (DMSO, 500 MHz) δ ppm 9.3-9.0 (m, 3H), 7.68 (d, 1H), 7.47-7.32 (m, 4H), 7.36 (bs, 1H), 4.53 (d, 2H), 4.3 (bm, 2H), 3.8-3.5 (m, broad, 4H), 3.3 (m, 2H), 3.1 (m, 2H). LC/MS (Method 2); Rt=1.37 min; detected mass: m/z=400.1 ([M+H]+).

Intermediate 2:
5-Piperazin-1-ylmethyl-thiophene-2-carboxylic acid 2,4-dichloro-benzylamide hydrochloride

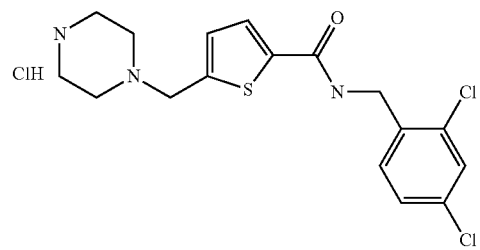 [SMILES: Cl ; O=C(NCc1ccc(Cl)cc1Cl)c1ccc(CN2CCNCC2)s1]

Synthesized in the same way as intermediate 1 but starting from 4-(5-Carboxy-thiophen-2-ylmethyl)-piperazine-1-carboxylic acid tert-butyl ester and 2-4-dichlororobenzylamide.
1H NMR (DMSO, 500 MHz) δ ppm 9.8 (bs, 2H), 9.51 (bs, 1H), 7.87 (bs, 1H), 7.60 (bs, 1H), 7.4 (m, 2H), 7.33 (d, 1H), 4.54 (bs, 2H), 4.48 (d, 2H), 3.7 (m, broad, 4H), 3.4-3.1 (bm, 4H). LC/MS (Method 4): Rt=2.94 min; detected mass: m/z=384.16 ([M+H]+).

Intermediate 3:
5-Piperazin-1-ylmethyl-thiophene-2-carboxylic acid 2-trifluoromethyl-benzylamide

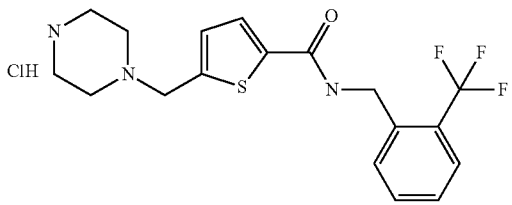 [SMILES: Cl ; O=C(NCc1ccccc1C(F)(F)F)c1ccc(CN2CCNCC2)s1]

The intermediate was synthesized in the same way as intermediate 1 but starting from 4-(5-Carboxy-thiophen-2-ylmethyl)-piperazine-1-carboxylic acid tert-butyl ester and 2-trifluoromethylbenzylamine.

1H NMR (DMSO, 500 MHz) δ ppm 9.08 (t, 1H), 8.5 (bs, 2H), 7.73 (m, 2H), 7.68 (m, 1H), 7.49 (m, 2H), 7.06 (m, 1H), 4.52 (m, 2H), 3.79 (s, 2H), 3.1 (bs, 4H), 2.58 (bm, 4H). LC/MS (Method 4): Rt=1.25 min; detected mass: m/z=384.05 ([M+H]+).

Intermediate 4: 5-piperazin-1-ylmethyl-thiophene-2-carboxylic acid (3-methyl-butyl)-amide Hydrochloride

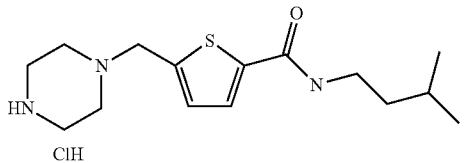 [SMILES: CC(C)CCNC(=O)c1ccc(CN2CCNCC2)s1 ; Cl]

To a solution of 4-(5-Carboxy-thiophen-2-ylmethyl)-piperazine-1-carboxylic acid tert-butyl ester (4 g, 13.0 mmol), HOBt (1.9 gr, 14.3 mmol), 3-Methyl-butylamine (1.18 g, 13.6 mmol) and NMM (3.9 g, 38.9 mmol) in DMF (20 ml), ECD*HCl was added (2.6 gr, 13.6 mmol). The mixture was stirred at RT, until conversion to product was observed (about 3 h). The received mixture was diluted with EtOAc and washed with water. The organic layer was then washed with diluted HCl (2×) and then with brine. The organic layer was dried over MgSO4 and the solvent was evaporated to give the above-identified intermediate (3.7 gr). The crude material was stirred at RT in 4 M HCl in dioxane (20 mL) for 2 hr. The formed solid was filtered off and dried to give 5-piperazin-1-ylmethyl-thiophene-2-carboxylic acid (3-methyl-butyl)-amide (Intermediate 4) as hydrochloride salt (3.18 gr, 74%). 1H NMR (DMSO, 500 MHz) δ ppm 9.5 (bs, 2H), 8.52 (bs, 1H), 7.7 (d, 1H), 7.33 (bs, 1H), 4.5 (bs, 2H), 3.65 (m, 2H), 3.38 (m, 4H), 3.22 (m, 4H), 1.59 (m, 1H), 1.40 (m, 2H), 0.9 (d, 6H). LC/MS (Method 4): Rt=2.43 min; detected mass: m/z=296.24 ([M+H]+).

Intermediate 5: 5-Piperazin-1-ylmethyl-thiophene-2-carboxylic acid (2-methoxy-pyridin-4-ylmethyl)-amide hydrochloride

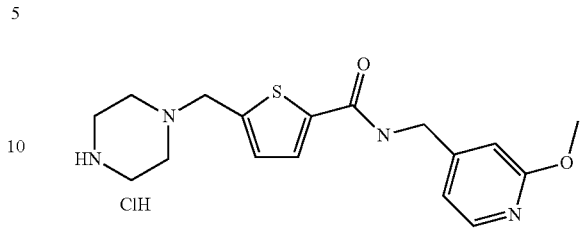

Synthesized in the same way as intermediate 1 but starting from 4-(5-Carboxy-thiophen-2-ylmethyl)-piperazine-1-carboxylic acid tert-butyl ester and C-(2-Methoxy-pyridin-4-yl)-methylamine.

1H NMR (DMSO, 400 MHz) δ ppm 9.25 (bm, 2H), 8.11 (d, 1H), 7.80 (d, 1H), 7.32 (bs, 1H), 6.90 (d, 1H), 6.19 (s, 1H), 4.43 (d, 2H), 4.34 (bs, 2H), 3.82 (s, 3H), 3.32 (bs, 4H), 3.17 (bs, 4H). LC/MS (Method 4): Rt=0.73 min; detected mass: m/z=347.1 ([M+H]+).

Intermediate 6: 5-[4-(2,4-Dimethyl-6-oxo-6H-pyran-3-carbonyl)-piperazin-1-ylmethyl]-thiophene-2-carboxylic acid hydrochloride

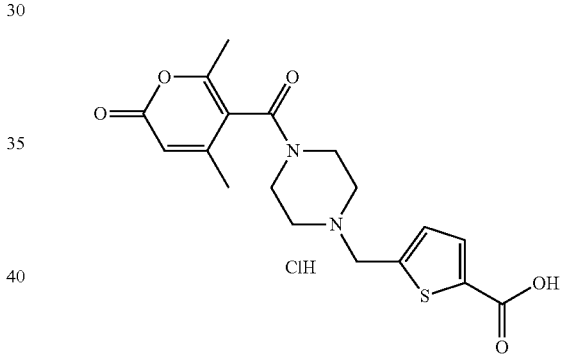

46 mL of 5N HCl were added to solid 4-(5-Carboxy-thiophen-2-ylmethyl)-piperazine-1-carboxylic acid tert-butyl ester (15.2 g, 46.4 mmol) at RT. The mixture was warmed at 50° C. for about 1 hour and the initial suspension turns into a clear solution. After 1 hour and 45 min, LC/MS showed full conversion to the above-identified intermediate. The pH of the resulting solution was adjusted to pH 6.8 by addition of a 32% aqueous solution of NaOH under cooling in an ice bath. The resulting light yellow solution was concentrated under reduced pressure. Then toluene was added (50 mL) and the mixture evaporated (2×). After addition of heptane (50 mL) the mixture was also evaporated (2×) and the crude material used in the following step without further purification. The resulting solid contains 5-Piperazin-1-ylmethyl-thiophene-2-carboxylic acid in about. 43% purity and NaCl.

The previous solid (22.4 gr, 43% purity, 42.5 mmol) was suspended in MeCN (150 mL) under Argon and BSA (25.98 g, 127.7 mmol) was added. The mixture was heated for 1 h at 82° C. until formation of a yellow solution. The mixture was left to cool down and at 43° C., isodehydroacetic acid chloride (prepared in situ from the corresponding acid and thionyl chloride, using standard procedures) (7.94 gr, 42.5 mmol) was added. The mixture was again warmed at 82° C. After 1 h, the reaction mixture was allowed to cool down and at 40° C., NaCl was filtered off and washed with MeCN. The solvent was then evaporated and the residue was taken up in 125 mL of water. The formed suspension was filtered off and the mother liquor was acidified with 5.2 g of 32% aq. HCl until pH 1.4 was reached. The water was evaporated and the residue suspended in toluene and evaporated (2×50 mL) and then suspended in heptane and evaporated (2×50 mL). The crude material was then warmed at 58° C. in acetone (235 ml) containing 2 mL of water (2 mL) for 1 h and the formed crystals were collected at 43° C. and washed with acetone. The product was again recrystallized in about 150 mL of a acetone: water (3:1) mixture to give d 5-[4-(2,4-Dimethyl-6-oxo-6H-pyran-3-carbonyl)-piperazin-1-ylmethyl]-thiophene-2-carboxylic acid hydrochloride (Intermediate 6) as a creme solid. (7.4 gr, 24%). 1H NMR (D$_2$O, 400 MHz) δ ppm 7.71 (d, 1H), 7.32 (d, 1H), 6.28 (s, 1H), 4.57 (s, 2H), 3.9-3.2 (m, 8H), 2.2 (s, 3H), 2.0 (s, 3H). LC/MS (Method 5); Rt=3.60 min; detected mass: m/z=377.43 ([M+H]+).

Intermediate 7: 5-Formyl-thiophene-2-carboxylic acid 2,4-dichloro-benzylamide

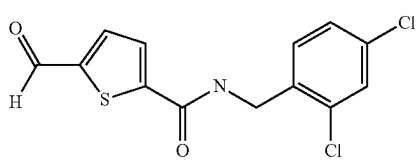 [SMILES: O=Cc1ccc(C(=O)NCc2ccc(Cl)cc2Cl)s1]

To a suspension of 5-Formyl-2-thiophenecarboxylic acid (2 g, 12.81 mmol) in 50 ml dichloromethane at 0° C., 1-Chlor-N,N,2-trimethylpropinylamin (1.88 g, 14.1 mmol) was added. The mixture was stirred 5 min at 000° C. and then was allowed to reach RT and stirred at this temperature for 15 min. To the obtained clear solution, a solution of 2,4-dichlorobenzylamine (2.5 g, 14.1 mmol) and triethylamine (19.2 mmol) in 10 ml dichloromethane were added and the reaction was stirred at RT overnight. The mixture was diluted with dichloromethane and washed with aqueous HCl (0.25 M). The organic layer was dried, filtered off and concentrated under reduced pressure. The obtained residue-5-Formyl-thiophene-2-carboxylic acid 2,4-dichloro-benzylamide (Intermediate 7)-(3.3 g, 82%) was used in the next step without further purification. 1H NMR (DMSO-d6, 500 MHz) δ ppm 9.9 (s, 1H), 9.41 (t, 1H), 8.07 (d, 1H), 7.98 (d, 1H), 7.53 (s, 1H), 7.49-7.35 (m, 2H), 4.52 (d, 2H). LC/MS (Method 2) Rt=1.73 min; detected mass: m/z=360.12 ([M+H]+).

Intermediate 8: 5-Formyl-thiophene-2-carboxylic acid 4-methoxy-2-trifluoromethoxy-benzylamide

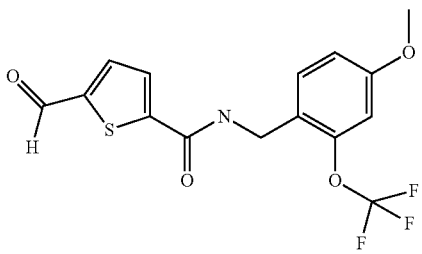 [SMILES: COc1ccc(CNC(=O)c2ccc(C=O)s2)c(OC(F)(F)F)c1]

To a solution of 5-Formyl-2-thiophenecarboxylic acid (100 mg, 0.64 mmol) and (4-methoxy-2-(trifluoromethoxy)phenyl)methanamine (141 mg, 0.64 mmol) in 4 ml DMF, HOBt (117 mg, 196 mmol) and 4-methylmorpholine (196 mg, 1.9 mmol) were added. Then 1-(3-Dimethylaminopropyl)-3-ethylcarbodiimide hydrochloride (168 mg, 0.83 mmol) was added and the mixture stirred at RT over night. The resulting solution was filtered, 0.1 mL TFA was added and purified by HPLC to give 5-Formyl-thiophene-2-carboxylic acid 4-methoxy-2-trifluoromethoxy-benzylamide (Intermediate 8)-(78 mg, 26%). 1H NMR (DMSO-d6, 500 MHz) δ ppm 9.9 (s, 1H), 9.28 (t, 1H), 8.05 (d, 1H), 7.91 (d, 1H), 7.40 (dd, 1H), 6.99 (dd, 1H), 6.90 (s, 1H), 4.48 (d, 2H) 3.80 (s, 3H). LC/MS (Method 3); Rt=1.88 min; detected mass: m/z=314.10 ([M+H]+).

Intermediate 9: 5-Formyl-thiophene-2-carboxylic acid 2-trifluoromethoxy-benzylamide

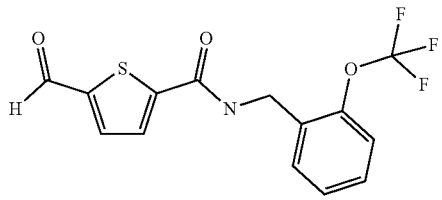 [SMILES: O=Cc1ccc(C(=O)NCc2ccccc2OC(F)(F)F)s1]

To a suspension of 5-Formyl-2-thiophenecarboxylic acid (2 g, 12.8 mmol) in 50 ml dichloromethane at 0° C., 1-Chlor-N,N,2-trimthylpropinylamin (1.8 g, 14.1 mmol) was added. The mixture was stirred 5 min at 000° C. and then was allowed to reach RT and stirred at this temperature for 15 min. To the obtained clear solution, a solution of 2,4-dichlorobenzylamine (2.69 g, 14.1 mmol) and diisorpopylethylamine (14.1 mmol) in 10 ml dichloromethane were added and the reaction was stirred at RT overnight. The mixture was diluted with dichloromethane and washed with aq. HCl (0.25 M). The organic layer was dried, filtered off and concentrated under reduced pressure to give the desired compound 5-Formyl-thiophene-2-carboxylic acid 2-trifluoromethoxybenzylamide (Intermediate 93.5 gr, 86%), which was used in the next step without further purification. 1H NMR (DMSO-d6, 500 MHz) δ ppm 9.9 (s, 1H), 9.39 (t, 1H), 8.06 (d, 1H), 7.95 (d, 1H), 7.5-7.3 (m, 4H), 4.52 (d, 2H). LC/MS (Method 3); Rt=1.86 min; detected mass: m/z=330.03 ([M+H]+).

Intermediate 10: 5-[4-(2,4-Dimethyl-6-oxo-6H-pyran-3-carbonyl)-piperazin-1-ylmethyl]-4-methyl-thiophene-2-carboxylic acid

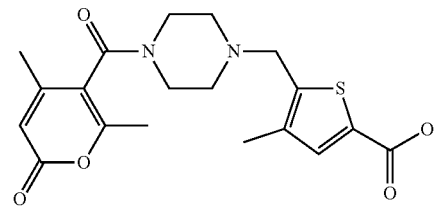 [SMILES: Cc1cc(C(=O)O)sc1CN1CCN(C(=O)c2c(C)cc(=O)oc2C)CC1]

To a solution of isodehydracetic acid (2 g, 7.22 mmol) in dioxane (5 mL) at 0° C., 1-chloro-N,N,2-trimethylpropynylamine was added in portions (1.33 g, 7.9 mmol). The mixture was stirred 1 h at RT and was added slowly to a suspension of 4-methyl-5-(piperazin-1-ylmethyl)thiophene-2-carboxylic acid (commercially available or easily prepared from known commercial starting materials) and sodium bicarbonate (1.5 gr, 2.5 mmol) in dioxan (10 ml). The mixture was allowed to stir overnight at RT and then the solvent was evaporated. 10 mL of pyridine was added and 1 mL of water and the mixture stirred for 4 h at RT. Toluene was added, the mixture evaporated and the residue purified by HPLC to give 5-[4-(2,4-Dimethyl-6-oxo-6H-pyran-3-carbonyl)-piperazin-1-ylmethyl]-4-methyl-thiophene-2-carboxylic acid (intermediate 10) as a white solid (1.68 g, 60%). 1H NMR (DMSO-d6, 500 MHz) δ ppm 7.54 (s, 1H), 7.28 (s, 1H), 6.12 (s, 1H), 4.5 (bs, 2H), 3.5 (bm, 8H), 2.22 (s, 3H), 2.12 (s, 3H), 2.0 (s, 3H).

Intermediate 11: 5-[4-(2-Hydroxy-propionyl)-piperazin-1-ylmethyl]-thiophene-2-carboxylic acid hydrochloride

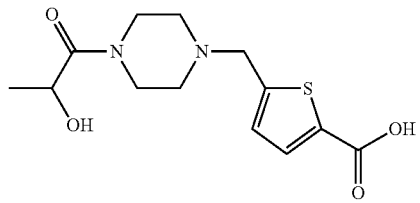 [SMILES: CC(O)C(=O)N1CCN(Cc2ccc(C(=O)O)s2)CC1]

To a solution of 4-(5-Carboxy-thiophen-2-ylmethyl)-piperazine-1-carboxylic acid tert-butyl ester (9.8 g, 30.0 mmol) in dichloromethane (300 mL) at 0° C., oxalyl chloride was added (10.3 ml, 120 mmol). The mixture was stirred at this temperature for 30 min and then quenched with MeOH (100 mL). The solvent was evaporated and the resulting residue taken up in dichloromethane (200 mL) and trifluoroacetic acid was added (50 mL) and the mixture stirred at RT overnight. The solvent was evaporated and the resulting solid suspended in boiling THF. After cooling down to RT the resulting solid was filtered off and washed with diisopropylether to give 5-Piperazin-1-ylmethyl-thiophene-2-carboxylic acid methyl ester as the trifluoroacetate salt (8.8 g, 78%).

To a solution of 5-Piperazin-1-ylmethyl-thiophene-2-carboxylic acid methyl ester trifluoroacetate salt (6.9 g, 24.9 mmol) and sodium-2-(tert-Butyl-dimethyl-silanyloxy)-propionate (6.77 g, 29.92 mmol)-prepared from methyl lactate and tert butyldiemthylchlorosilane using standard procedures- and triethylamine (10.6 ml, 74.8 mmol) in THF (200 mL) at RT, TOTU (9.8 g, 29.92 mmol) was added and the mixture stirred at RT overnight. EtOAc was added (200 mL) and the organic layer was washed with water (2 times) and concentrated under reduced pressure to give an oil (6.9 g, 65%). LC/MS (Method 6); Rt=4.11 min; detected mass: m/z=427.29 ([M+H]+).

The above obtained oil (4.8 g, 11.25 mmol) was dissolved in MeOH (25 ml) and then 1M NaOH was added (15 ml). The mixture was stirred at RT overnight and the solvent was evaporated. The resulting oil was suspended in toluol and after evaporation (2 times) sodium 5-{4-[2-(tert-Butyl-dimethyl-silanyloxy)-propionyl]-piperazin-1-ylmethyl}-thiophene-2-carboxylate as a white solid (4.7 g, 96%) was prepared. LC/MS (Method 3); Rt=1.57 min; detected mass: m/z=413.3 ([M+H]+).

A solution of sodium 5-{4-[2-(tert-Butyl-dimethyl-silanyloxy)-propionyl]-piperazin-1-ylmethyl}-thiophene-2-carboxylate (40 mg, 0.097 mmol) in 5M HCl in isopropanol (4 mL) was stirred at RT overnight. The solvent was evaporated and the residue purified by supercritical fluid chromatography to give 5-[4-(2-Hydroxy-propionyl)-piperazin-1-ylmethyl]-thiophene-2-carboxylic acid hydrochloride as an oil (35 mg; 100%): 1H NMR (DMSO-d6, 400 MHz) δ ppm 9.12 (s, 1H), 9.39 (t, 1H), 8.06 (d, 1H), 7.95 (d, 1H), 7.5-7.3 (m, 4H), 4.52 (d, 2H). LC/MS (Method 2); Rt=0.43 min; detected mass: m/z=299.17 ([M+H]+).

Intermediate 12:
2-Piperazin-1-ylmethyl-thiazole-5-carboxylic acid 2,4-dichloro-benzylamide dihydrochloride

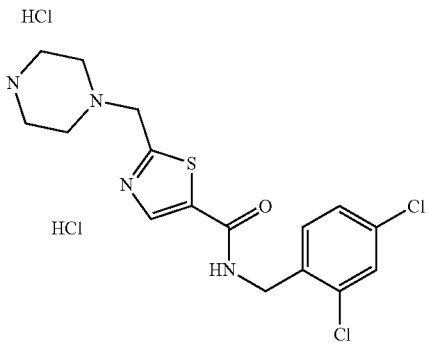 [SMILES: Cl ; O=C(NCc1ccc(Cl)cc1Cl)c1cnc(CN2CCNCC2)s1 ; Cl]

Step 1

Synthesis of 4-(5-Ethoxycarbonyl-thiazol-2-ylmethyl)-piperazine-1-carboxylic acid tert-butyl ester A mixture of 2-Bromomethyl-thiazole-5-carboxylic acid methyl ester [U.S. Pat. No. 6,162,808 A1 page 14] (17.5 g, 70 mmol), tert-butyl 1-piperazinecarboxylate (13.03 g, 70 mmol), K₂CO₃ (19.35 g, 140 mmol) and NaI (2.09, 14 mmol) in dry acetonitrile (576 mL) was stirred at reflux under nitrogen atmosphere for 1 h. After cooling down, the solvent was removed under reduced pressure and the residue was suspended in dichloromethane (0.5 L). The solid was removed by filtration, washed with dichloromethane and the filtrate was concentrated to dryness. The crude reaction product was purified by flash column chromatography (SiO2, c-Hex/AcOEt) to give 18 g of 4-(5-Ethoxycarbonyl-thiazol-2-ylmethyl)-piperazine-1-carboxylic acid tert-butyl ester (72%). 1H NMR (CDCl3, 500 MHz) δ 8.27 (s, 1H), 4.34 (dd, 2H), 3.83 (s, 2H), 3.46 (m, 4H), 2.54 (m, 4H), 1.44 (s, 9H), 1.36 (t, 3H). MS-(ESI) 356.13/357.13 [M+]

Step 2

To a solution of 4-(5-Ethoxycarbonyl-thiazol-2-ylmethyl)-piperazine-1-carboxylic acid tert-butyl ester (4.0 gr, 11.25 mmol) in EtOH (40 mL), 3.4 mL of a 5M NaOH solution in water were added. The mixture was allowed to stir at RT overnight and then the solvent was evaporated. 50 mL of water were added and the solution was acidified by adding 5M aqueous HCl (3.7 mL). The resulting suspension was cooled for 1 h in an ice bath and then filtered off. The solid was washed with water and dried with ethyl ether and used in the following amide coupling without further purification.

To a solution of the previous solid (3.4 g, 10.6 mmol), 2,4-dichlorobenzylamine (1.96 g, 11.3 mmol), N-Methyl morpholine (2.6 gr, 26.5 mmol) and HOBt (1.6 gr, 11.66 mmol) in DMF (63 mL), 1-(3-dimethylaminopropyl)-3-ethylcarbodiimide (1.8 gr, 11.66 mmol) were added. The mixture was stirred at RT overnight and then DMF was evaporated under reduced pressure. The crude material was diluted in EtOAc and washed with water and saturated NaHCO$_3$ solution. The organic layer was dried, filtered off and evaporated to give crude 4-[5-(2,4-Dichloro-benzylcarbamoyl)-thiazol-2-ylmethyl]-piperazine-1-carboxylic acid tert-butyl ester (5.4 g). The residue was dissolved in dioxane (30 mL) and then 40 mL of 4M HCl in dioxane were added. The mixture was allowed to stir at RT overnight and the resulting solid was filtered off and washed with dioxane and diisopropylether.

2-Piperazin-1-ylmethyl-thiazole-5-carboxylic acid 2,4-dichloro-benzylamide dihydrochloride (Intermediate 12) (4.85 g, 88%) was obtained as a colorless solid in about 90% purity.

$^1$H NMR (DMSO-d6, 400 MHz) δ 9.36 (bs, 1H), 9.20 (bs, 2H), 8.49 (s, 1H), 7.52 (s, 1H), 7.40 (m, 2H), 4.5 (d, 2H), 4.25 (bs, 2H), 3.22 (bs, 4H), 3.04 (bs, 4H). LC/MS (Method 3): Rt=1.29 min; detected mass: m/z=385.18 ([M+H]+).

General Procedure for the Coupling of Intermediates II (1-5 and 12):

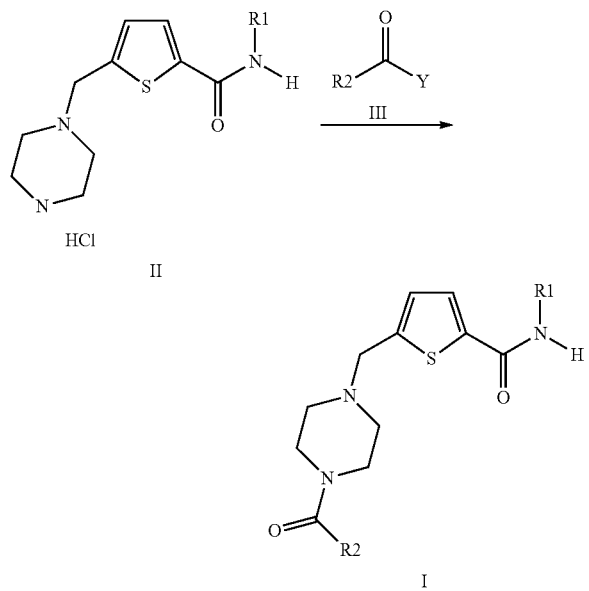

Method 1

A reaction vessel was filled with a solution containing the corresponding carboxylic acid (0.13 mmol). Then 0.75 ml of a stock solution containing HOBt*H2O (0.13 mmol), N-methylmorpholine (1 mmol) and DMAP (0.01 mmol) were added and the mixture was stirred at RT until the acid had dissolved. Subsequently a solution of the corresponding intermediate (1-5) in 1 ml of DMF was added, followed by EDC (neat, 0.13 mmol). The tube was closed with a screw cap and shaken over night at 40° C. 0.1 ml TFA was added and the volume was adjusted to 2.2 ml with DMF. The solution was filtered and submitted to prep. RP-HPLC purification.

Method 2:

General Procedure for the Coupling of Intermediates IV (6, 10, 11)

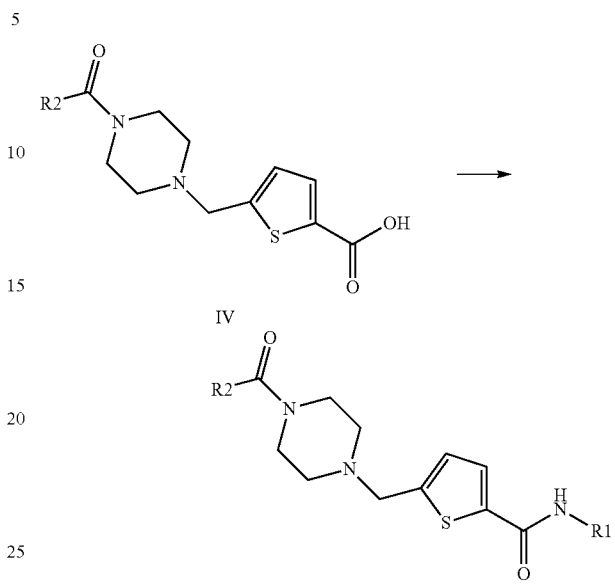

Method 1: Amide Coupling

To a solution of the corresponding thiophen-2-carboxylic acid intermediate (IV) (14.85 mmol) in DMF (100 mL), HOBt x H2O (17.55 mmol) and N-methyl morpholine (81 mmol) were added. Then EDC (17.55 mmol) was added and the mixture was stirred for 40 minutes at RT to form the active ester. The volume was adjusted to 135 ml with DMF.

The corresponding amine (0.15 mmol) was weighed into a reaction tube and 1 ml of the above stock solution (containing about 0.11 mmol of the active ester) was added, the tube was closed with a screw cap and shaken at RT overnight. The mixture was diluted with 15 ml ethyl acetate and washed twice with 5 ml 5% NaHCO3 (aq) each, then dried by passage through a XTR Chroma bond column, and evaporated. The residue was submitted to SFC purification.

Method 2: Via Acid Chloride

Step 1: In a round bottom flask was introduced the corresponding thiophene-2-carboxylic acid (IV) (4.3 mmol) and suspended in dry CH$_2$Cl$_2$ (50 mL). The flask was fitted with a dropping funnel and an Argon bubbler, purged with Argon, and then cooled in an ice bath. Then 1-chloro-2,2,N-trimethylpropenylamine (7.1 mmol) in dry CH2Cl2 (5 mL) was added drop wise during 30 min with stirring. The reaction was allowed to stir for 3 h at RT until conversion of the acid to acid chloride was observed by LCMS. If the conversion was not complete additional amount 1-chloro-2,2,N-trimethylpropenylamine was added and further stirring at RT was done until complete conversion was achieved. The resulting solution was used in the next step without further treatment.

Step 2: In a reaction flask was introduced a solution of the corresponding amine (0.15 mmol) in THF (1 mL). Then diisopropylethylamine (0.5 mmol) was added followed by the corresponding amount of the solution generated in step 1 (containing 0.11 mmol of acid chloride). The reaction was purged with Ar and stirred overnight at RT. Then, the solvent was evaporated, a mixture of DMF and TFA was added (19:1 2 mL) and the products purified by HPLC.

General Procedures for the Reductive Aminations of Intermediates VI (7-9)

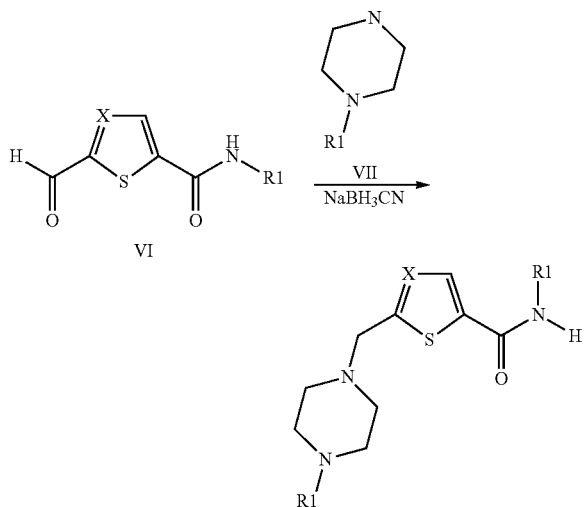

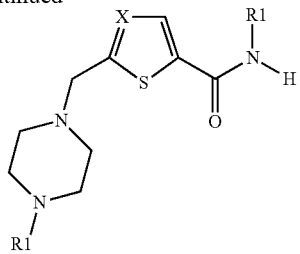

Method 1:
To a reaction vessel containing the corresponding amine VII (0.16 mmol), NaOAc (0.18 mmol) was added (+0.18 mmol for hydrochlorides per HCl), followed by the corresponding thiophenealdehyde or thiazolaldehyde VI (0.15 mmol) in 2 ml of THF, 0.4 ml glacial acetic acid, and finally 0.3 mmol polymer-bound cyanoborohydride. The tube was closed with a screw cap and shaken at RT overnight. The resin was filtered off and washed with 2×2 ml THF. The filtrate was diluted with 5 ml toluene and evaporated. The residue was dissolved in 15 ml ethyl acetate and washed with 2×5 ml 10% NaHCO3 (aqua), then dried by passage through an XTR Chroma bond column. The column was washed with 2 ml ethyl acetate. The filtrate was evaporated, the residue was dissolved in 2 ml DMF, filtered, and submitted to SFC to give the desired compound.

Method 2:
To a solution of the corresponding amine (VII) (0.41 mmol) and the corresponding 5-Formyl-thiophene-2-carboxylic amide (VI) (0.32 mmol), THF (6 mL) was added followed by glacial acetic acid (0.8 mL) and polymer-bound cyanoborohydride (0.64 mmol). The reaction tube was closed with a screw cap and shaken at RT overnight. The resin was filtered off and washed with 2×4 ml THF. The filtrate was diluted with 10 ml toluene and evaporated. The residue was dissolved in 4 ml DMF, filtered, and submitted to HPLC purification.

Method 3—Two Step Procedure:
Step 1: In a round bottom flask was introduced 5-formylthiophene-2-carboxylic acid (6.45 mmol) and suspended in 20 mL of dry CH2Cl2. The flask was fitted with a dropping funnel and an Argon bubbler, purged with Argon, and then cooled in an ice bath. Then 1-chloro-2,2,N-trimethylpropenylamine (7.75 mmol) in dry CH2Cl2 (5 mL) was added drop wise with stirring. The reaction was allowed to warm to RT and stirred for a further 30 minutes after all solids had dissolved. The solution was again cooled in an ice bath and a mixture of 6.75 mmol of the benzyl amine and 7.1 mmol diisopropyl ethyl amine in 5 ml dry THF was added drop wise with stirring. After the addition was complete the solution was allowed to warm to RT and stirred for another hour at this temperature. The solution was diluted with THF to a volume of 86 ml and used in the next step without further treatment.

Step 2:
In a reaction tube was introduced the corresponding piperazine (0.16 mmol). Then NaOAc (0-18 mmol, +0.18 mmol for hydrochlorides per HCl) was added, followed by 2 ml of the solution from step 1 (containing ca. 0.15 mmol of the corresponding intermediate VI), glacial acetic acid (0.4 ml), and finally polymer-bound cyanoborohydride (0.3 mmol). The tube was closed with a screw cap and shaken at RT overnight. The resin was filtered off and washed with 2×2 ml THF. The filtrate was diluted with 5 ml toluene and evaporated. The residue was dissolved in 15 ml ethyl acetate and washed with 2×5 ml 10% aqueous NaHCO3, then dried by passage through an XTR Chroma bond column. The column was washed with 2 ml ethyl acetate. The filtrate was evaporated and the residue was dissolved in 2 ml DMF, filtered, and submitted to SFC purification.

The following examples illustrate the invention.

Example 30: 5-[4-((R)-2-Hydroxy-3-methyl-butyryl)-piperazin-1-ylmethyl]-thiophene-2-carboxylic acid (2-methoxy-pyridin-4-ylmethyl)-amide

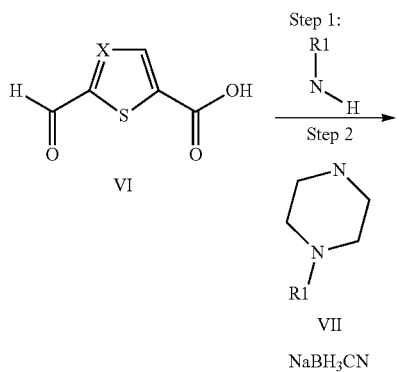

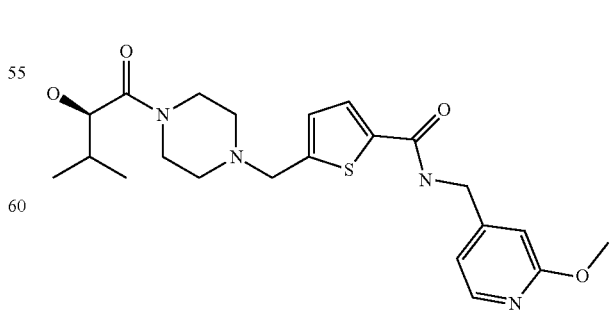

To (R)-(+)-2-Hydroxy-3-methylbutyric acid (15 mg, 0.13 mmol), a solution containing HOBt*H2O (0.13 mmol), N-methylmorpholine and 0.01 mmol DMAP in 0.75 ml DMF was added and the mixture was stirred at RT until the acid had dissolved. Then 5-piperazin-1-ylmethyl-thiophene-2-carboxylic acid (2-methoxy-pyridin-4-ylmethyl)-amide (Intermediate 5) (42 mg, 0.11 mmol) in 1 ml DMF was added, followed by 0.13 mmol EDC (neat). The tube was closed with a screw cap and shaken over night at 40° C. 0.1 ml TFA was added and the volume was adjusted to 2.2 ml with DMF. The solution was filtered and submitted to SFC purification to give the title compound as a colorless film (17 mg, 30%). 1H NMR (DMSO-d6, 500 MHz) δ ppm 9.02 (t, 1H), 8.1 (d, 1H), 7.66 (d, 1H), 7.02 (d, 1H), 6.90 (d, 1H), 6.68 (s, 1H), 4.6 (bs, 1H), 4.41 (d, 2H), 4.03 (d, 1H), 3.82 (s, 3H), 3.7 (s, 2H), 3.6-3.4 (m, 4H), 2.45-2.3 (m, 4H), 1.89 (m, 1H), 0.88 (d, 3H), 0.78 (d, 3H). LC/MS (Method 3); Rt=1.26 min; detected mass: m/z=447.20 ([M+H]+).

Example 54: 5-[4-(2-Hydroxy-propionyl)-piperazin-1-ylmethyl]-thiophene-2-carboxylic acid 2-trifluoromethoxy-benzylamide, trifluoroacetate

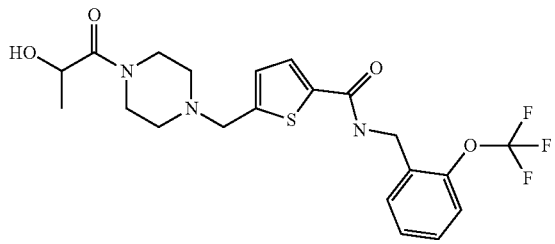 [SMILES: CC(O)C(=O)N1CCN(Cc2ccc(C(=O)NCc3ccccc3OC(F)(F)F)s2)CC1]

A solution containing HOBt*H2O (0.13 mmol), N-methylmorpholine (0.26 mmol) and 0.01 mmol DMAP in 0.75 ml DMF was added to a reaction vessel containing lactic acid (12 mg, 0.13 mmol) and the mixture was stirred at RT until the acid had dissolved. Then 5-piperazin-1-ylmethyl-thiophene-2-carboxylic acid 2-trifluoromethoxy-benzylamide hydrochloride (intermediate 1) (42 mg, 0.11 mmol) in 1 ml DMF was added, followed by 0.13 mmol EDC (neat). The tube was closed with a screw cap and shaken over night at 40° C. 0.1 ml TFA was added and the volume was adjusted to 2.2 ml with DMF. The solution was filtered and submitted to preparative RP-HPLC purification to give the title compound as a colorless film (42 mg, 65%). 1H NMR (DMSO-d6, 500 MHz) δ ppm 9.14 (bs, 1H), 7.8 (s, 1H), 7.49-7.36 (m, 4H), 7.26 (bs, 1H), 4.51 (d, 2H), 4.5 (bs, 2H), 3.8-3.3 (m, 6H), 3.0 (m, 2H), 1.19 (2, 3H), 0.88 (d, 3H), 0.78 (d, 3H). LC/MS (Method 3); Rt=1.00 min; detected mass: m/z=472.22 ([M+H]+).

Example 60: 5-[4-(2,4-Dimethyl-6-oxo-6H-pyran-3-carbonyl)-piperazin-1-ylmethyl]-thiophene-2-carboxylic acid 4-chloro-2-fluoro-benzylamide

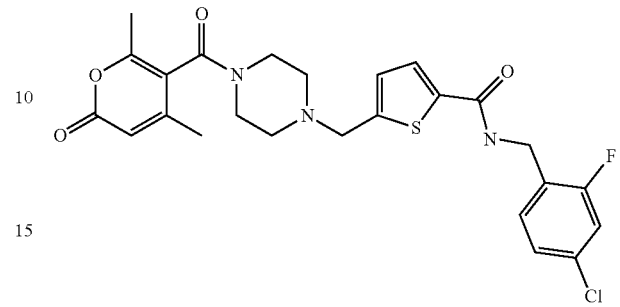

To a solution containing 5-[4-(2,4-dimethyl-6-oxo-6H-pyran-3-carbonyl)-piperazin-1-ylmethyl]-thiophene-2-carboxylic acid hydrochloride (intermediate 6) (45 mg, 0.11 mmol), HOBt*H2O (0.13 mmol), N-methylmorpholine (0.55 mmol) in 1 mL DMF, EDC (0.13 mmol) was added and the mixture was stirred at RT for 40 min. Then 4-chloro-2-fluoro-benzylamine (0.15 mmol) was added and the mixture stirred at RT over night. The mixture was diluted with 15 ml ethyl acetate and washed twice with 5 ml 5% NaHCO3 (aq) each, then dried by passage through a XTR Chromabond column, and evaporated. The residue was submitted to SFC purification to give the title compound as colorless oil (14 mg, 25%). 1H NMR (DMSO-d6, 500 MHz) δ ppm 8.99 (t, 1H), 7.8 (s, 1H), 7.49-7.36 (m, 4H), 7.26 (bs, 1H), 4.51 (d, 2H), 4.5 (bs, 2H), 3.8-3.3 (m, 6H), 3.0 (m, 2H), 1.19 (2, 3H), 0.88 (d, 3H), 0.78 (d, 3H). LC/MS (Method 1); Rt=1.07 min; detected mass: m/z=518.12 ([M+H]+).

Example 115: 5-[4-(1-Amino-cyclopropanecarbonyl)-piperazin-1-ylmethyl]-thiophene-2-carboxylic acid 2-trifluoromethoxy-benzylamide, trifluoroacetate

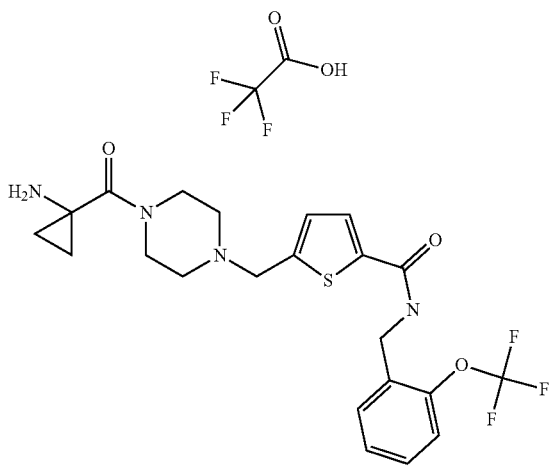

To a solution of 1-[(tert-butoxycarbonyl)amino]cyclopropanecarboxylic acid (114 mg, 0.57 mmol), ethyl cyanoglioxylate-2-oxyma (81 mg, 0.57 mmol), DMAP (2 mg, 0.017 mmol) and 5-piperazin-1-ylmethyl-thiophene-2-carboxylic acid 2-trifluoromethoxy-benzylamide hydrochloride (intermediate 1) (200 mg, 0.47 mmol) in 4 ml DMF, 4 methylmorpholine (0.12 mL, 1.04 mmol) was added, followed by 1-ethyl-3-(3-dimethylaminopropyl)carbodiimide hydrochloride (109 mg, 0.57 mmol). The mixture was stirred at RT over night. The resulting solution was extracted with EtOAc and a saturated solution of sodium bicarbonate. The phases were separated and the organic layer concentrated under reduced pressure and redissolved in 2 mL DMF. 0.1 ml TFA was added and the volume was adjusted to 2.2 ml with DMF. The solution was filtered and submitted to preparative RP-HPLC purification to give (1-{4-[5-(2-trifluoromethoxy-benzylcarbamoyl)-thiophen-2-ylmethyl]-piperazine-1-carbonyl}-cyclopropyl)-carbamic acid tert-butyl ester as a white solid (232 mg, 83%).

To a solution of (1-{4-[5-(2-Trifluoromethoxy-benzylcarbamoyl)-thiophen-2-ylmethyl]-piperazine-1-carbonyl}-cyclopropyl)-carbamic acid tert-butyl ester (190 mg, 3.26 mmol) in dichloromethane (2.5 mL) at 0° C., 2.5 mL of trifluoroacetic acid were added and the mixture stirred at RT for 2 h. Then the solvent was evaporated to get 5-[4-(1-Amino-cyclopropanecarbonyl)-piperazin-1-ylmethyl]-thiophene-2-carboxylic acid 2-trifluoromethoxy-benzylamide trifluoroacetate as a white solid (194 mg, 100%). 1H NMR (DMSO-d6, 500 MHz) δ ppm 9.17 (t, 1H), 8.7 (bs, 2H), 7.8 (d, 1H), 7.49-7.36 (m, 4H), 7.26 (bs, 1H), 4.51 (d, 2H), 4.5 (bs, 2H), 3.8-3.3 (m, 6H), 3.0 (m, 2H), 1.2 (bs, 2H). LC/MS (Method 4); Rt=2.50 min; detected mass: m/z=483.32 ([M+H]+).

Example 120: 5-[4-(2,6-Dimethyl-pyridin-4-yl)-piperazin-1-ylmethyl]-thiophene-2-carboxylic acid 2,4-dichloro-benzylamide

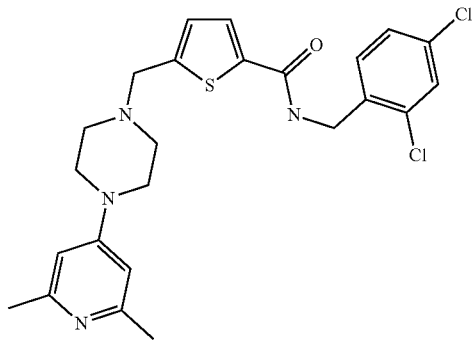 [SMILES: Cc1cc(N2CCN(Cc3ccc(C(=O)NCc4ccc(Cl)cc4Cl)s3)CC2)cc(C)n1]

Step 2:
0.16 mmol of the 1-(2,6-Dimethyl-pyridin-4-yl)-piperazine was weighed into a reaction tube. 0.18 mmol NaOAc was added, followed by a solution of 5-formyl-thiophene-2-carboxylic acid 2,4-dichloro-benzylamide (intermediate 7) (0.15 mmol) in 2 mL of THF. Then 0.4 ml glacial acetic acid and finally polymer-bound cyanoborohydride (0.3 mmol) were added and shaken at RT over night. The resin was filtered off and washed with 2×2 ml THF. The filtrate was diluted with 5 ml toluene and evaporated. The residue was dissolved in 15 ml ethyl acetate and washed with 2×5 ml 10% NaHCO3(aq), dried by passage through an XTR Chromabond column. The column was washed with 2 ml ethyl acetate. The received filtrate was evaporated, the residue was dissolved in 2 ml DMF, filtered, and submitted to SFC purification to give the 5-[4-(2,6-Dimethyl-pyridin-4-yl)-piperazin-1-ylmethyl]-thiophene-2-carboxylic acid 2,4-dichloro-benzylamide (5.6 mg, 8%). 1H NMR (DMSO-d6, 500 MHz) δ ppm 9.0 (t, 1H), 7.7 (d, 1H), 7.62 (s, 1H), 7.44 (dd, 1H), 7.37 (dd, 1H), 7.02 (d, 1H), 6.5 (bs, 2H), 4.49 (d, 2H), 3.7 (s, 2H), 3.3 (bs, 4H), 2.5 (bs, 4H), 2.29 (s, 6H). LC/MS (Method 4); Rt=1.51 min; detected mass: m/z=491.24 ([M+2H]+; 489.25 ([M]+).).

Example 139: 5-[4-(3,5-Dimethyl-1H-pyrazole-4-carbonyl)-piperazin-1-ylmethyl]-thiophene-2-carboxylic acid (2-methoxy-pyridin-4-ylmethyl)-amide trifluoroacetate

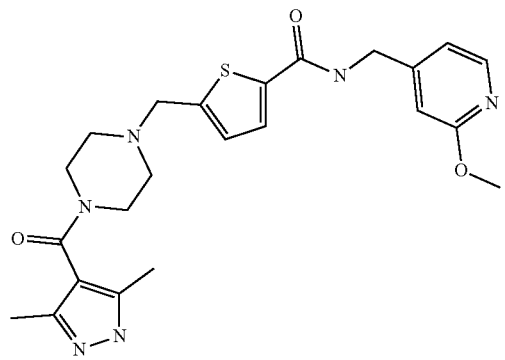

To a solution of 3,5-dimethyl-1H-pyrazole-4-carboxylic acid (18 mg, 0.13 mmol), HOBt*H2O (0.13 mmol), N-Methylmorpholine (1 mmol), 4-Dimethylaminopyridine (0.01 mmol) in 0.75 mL of DMF, a solution of intermediate 5 (0.11 mmol in 1 mL DMF) was added followed by EDC (neat, 0.13 mmol). The tube was closed with a screw cap and shaken over night at 40° C. 0.1 ml TFA was added and the volume was adjusted to 2.2 ml with DMF. The solution was filtered and submitted to preparative RP-HPLC purification to give 5-[4-(3,5-Dimethyl-1H-pyrazole-4-carbonyl)-piperazin-1-ylmethyl]-thiophene-2-carboxylic acid (2-methoxy-pyridin-4-ylmethyl)-amide trifluoroacetate as a colorless film (33 mg, 52%). 1H NMR (DMSO-d6, 500 MHz) δ ppm 9.22 (t, 1H), 8.1 (d, 1H), 7.80 (d, 1H), 7.30 (bs, 1H), 6.90 (d, 1H), 6.69 (s, 1H), 4.6 (bs, 2H), 4.40 (bs, 2H), 4.3-3.7 (broad signal, 4H), 3.7 (s, 3H), 3.5-3.0 (broad signal, 4H), 2.13 (s, 6H). LC/MS (Method 3); Rt=1.15 min; detected mass: m/z=469.31 ([M+H]+)

Example 149: 5-[4-(3,6-Difluoro-pyridine-2-carbonyl)-piperazin-1-ylmethyl]-thiophene-2-carboxylic acid (2-methoxy-pyridin-4-ylmethyl)-amide

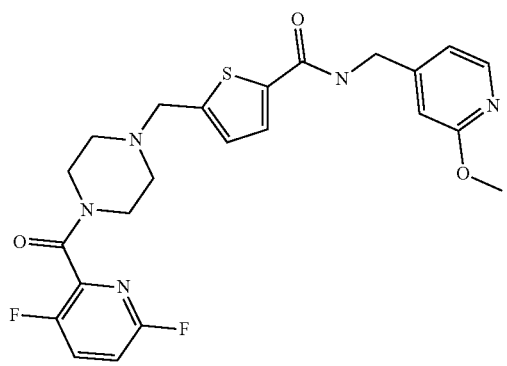 [SMILES: COc1cc(CNC(=O)c2ccc(CN3CCN(C(=O)c4nc(F)ccc4F)CC3)s2)ccn1]

To a solution of 3,6-difluoro-pyridine-2-carboxylic acid (20 mg, 0.13 mmol), HOBt*H₂O (0.13 mmol), N-methyl-morpholine (1 mmol), 4-dimethylaminopyridine (0.01 mmol) in 0.75 mL of DMF, a solution of intermediate 5 (0.11 mmol in 1 mL DMF) was added followed by EDC (neat, 0.13 mmol). The tube was closed with a screw cap and shaken over night at 40° C. 0.1 ml TFA was added and the volume was adjusted to 2.2 ml with DMF. The solution was filtered and submitted to preparative RP-HPLC purification. The resulting product obtained after freeze drying was redissolved in DMF and submitted to SFC purification to give 5-[4-(3,6-Difluoro-pyridine-2-carbonyl)-piperazin-1-ylmethyl]-thiophene-2-carboxylic acid (2-methoxy-pyridin-4-ylmethyl)-amide as a colorless film (19 mg, 35%). 1H NMR (DMSO-d6, 500 MHz) δ ppm 9.01 (t, 1H), 8.08 (m, 2H), 7.56 (d, 1H), 7.40 (m, 1H), 7.02 (d, 1H), 6.90 (d, 1H), 6.57 (s, 1H), 4.39 (d, 2H), 3.82 (s, 3H), 3.75 (s, 2H), 3.62 (m, 2H), 3.25 (m, 4H). LC/MS (Method 3); Rt=1.33 min; detected mass: m/z=488.23 ([M+H]+)

Example 177: 2-[4-(2-Dimethylamino-propionyl)-piperazin-1-ylmethyl]-thiazole-5-carboxylic acid 2,4-dichloro-benzylamide

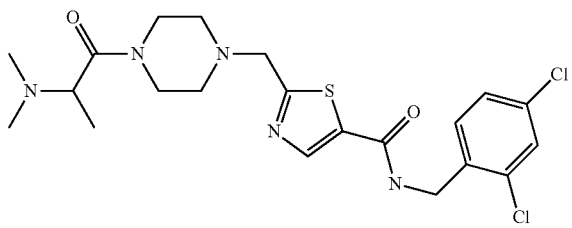 [SMILES: CC(C(=O)N1CCN(Cc2ncc(C(=O)NCc3ccc(Cl)cc3Cl)s2)CC1)N(C)C]

To a solution of 2-dimethylamino-propionic acid (15 mg, 0.13 mmol), intermediate 12 (50 mg, 0.11 mmol), HOBt (18 mg, 0.13 mmol) and N-methylmorpholine (101 mg, 1.0 mmol) in DMF (2 mL), EDC was added (20 mg, 0.13 mmol). The reaction vessel was closed with a screw cap and the reaction stirred at 40° C. over night. The reaction mixture was diluted with 15 ml ethyl acetate and washed twice with 5 ml 5% NaHCO₃ each. The organic phase was dried by passage through an XTR Chromabond column, and evaporated. The residue was dissolved in 2 ml DMF and submitted to SFC purification to give 2-[4-(2-Dimethylamino-propionyl)-piperazin-1-ylmethyl]-thiazole-5-carboxylic acid 2,4-dichloro-benzylamide (24 mg, 45%). 1H NMR (DMSO-d6, 400 MHz) δ 9.29 (t, 1H), 8.33 (s, 1H), 7.62 (s, 1H), 7.4 (dd, 2H), 4.5 (d, 2H), 3.82 (s, 2H), 3.7-3.5 (m, 4H), 3.4 (m, 2H). 2.5 (m, 2H), 2.42 (m, 1H), 2.14 (s, 6H), 1.01 (d, 3H). LC/MS (Method 3): Rt=1.21 min; detected mass: m/z=484.21 ([M+H]+).

According to the previous examples the following compounds were prepared in close analogy.

In case of trifluoroacetic acid salts formed by the procedure described above, the free base could be isolated via following procedure: The respective trifluoroacetic acid salt was partitioned between an organic solvent (dichloromethane, tert.-butyl methyl ether or ethyl acetate) and saturated aqueous sodium carbonate solution and stirred for 30 min. The organic layer was separated, washed with water, dried over magnesium sulfate, filtered and evaporated to give free base.

| No | Starting compound | Chemical name | Mass (from LC/MS) | $R_t$ (from LC/MS) (min) | LC/MS Method |
|---|---|---|---|---|---|
| 1 | Intermediate 1 | 5-[4-((R)-2-Hydroxy-propionyl)-piperazin-1-ylmethyl]-thiophene-2-carboxylic acid 2-trifluoromethoxy-benzylamide; Trifluoroacetate | 472.28 | 2.88 | 4 |
| 2 | Intermediate 2 | 5-[4-(3,5-Dimethyl-isoxazole-4-carbonyl)-piperazin-1-ylmethyl]-thiophene-2-carboxylic acid 2,4-dichloro-benzylamide; Trifluoroacetate | 507.14 | 0.99 | 2 |
| 3 | Intermediate 3 | 5-{4-[2-(2-Chloro-phenyl)-acetyl]-piperazin-1-ylmethyl}-thiophene-2-carboxylic acid 2-trifluoromethyl-benzylamide; Trifluoroacetate | 536.2 | 1.02 | 2 |
| 4 | Intermediate 3 | 5-[4-(Pyridine-3-carbonyl)-piperazin-1-ylmethyl]-thiophene-2-carboxylic acid 2-trifluoromethyl-benzylamide; Trifluoroacetate | 489.23 | 0.89 | 2 |
| 5 | Intermediate 4 | 5-[4-((1R,2R)-2-Phenyl-cyclopropane-carbonyl)-piperazin-1-ylmethyl]-thiophene-2-carboxylic acid (3-methyl-butyl)-amide | 440.14 | 1.12 | 2 |
| 6 | Intermediate 3 | 5-[4-(Bicyclo[4.2.0]octa-1(6),2,4-triene-7-carbonyl)-piperazin-1-ylmethyl]-thiophene-2-carboxylic acid 2-trifluoro-methyl-benzylamide; Trifluoroacetate | 514.22 | 1.01 | 2 |
| 7 | Intermediate 2 | 5-[4-(2-Methoxy-pyridine-3-carbonyl)-piperazin-1-ylmethyl]-thiophene-2-carboxylic acid 2,4-dichloro-benzylamide; Trifluoroacetate | 519.11 | 0.98 | 2 |
| 8 | Intermediate 2 | 5-[4-(Pyrazolo[1,5-a]pyridine-3-carbonyl)-piperazin-1-ylmethyl]-thiophene-2-carboxylic acid 2,4-dichloro-benzylamide; Trifluoroacetate | 528.14 | 0.95 | 2 |

-continued

| No | Starting compound | Chemical name | Mass (from LC/MS) | R_t (from LC/MS) (min) | LC/MS Method |
|---|---|---|---|---|---|
| 9 | Intermediate 6 | 5-[4-(2,4-Dimethyl-6-oxo-6H-pyran-3-carbonyl)-piperazin-1-ylmethyl]-thiophene-2-carboxylic acid 4-methoxy-2-trifluoromethyl-benzylamide | 564.25 | 1.1 | 2 |
| 10 | Intermediate 6 | 5-[4-(2,4-Dimethyl-6-oxo-6H-pyran-3-carbonyl)-piperazin-1-ylmethyl]-thiophene-2-carboxylic acid (3,3-dimethyl-butyl)-amide | 460.28 | 1.06 | 2 |
| 11 | Intermediate 6 | 5-[4-(2,4-Dimethyl-6-oxo-6H-pyran-3-carbonyl)-piperazin-1-ylmethyl]-thiophene-2-carboxylic acid [3-(5-methyl-3-trifluoromethyl-pyrazol-1-yl)-propyl]-amide | 566.1 | 1.05 | 2 |
| 12 | Intermediate 4 | 5-[4-(5-Bromo-3-methyl-benzofuran-2-carbonyl)-piperazin-1-ylmethyl]-thiophene-2-carboxylic acid (3-methyl-butyl)-amide; Trifluoroacetate | 532.07 | 1.23 | 1 |
| 13 | Intermediate 4 | 5-[4-(2-Difluoromethyl-2H-pyrazole-3-carbonyl)-piperazin-1-ylmethyl]-thiophene-2-carboxylic acid (3-methyl-butyl)-amide; Trifluoroacetate | 440.14 | 1.05 | 1 |
| 14 | Intermediate 7 | 2-{4-[5-(2,4-Dichloro-benzylcarbamoyl)-thiophen-2-ylmethyl]-piperazin-1-yl}-N-methyl-nicotinamide; Trifluoroacetate | 518.2 | 1.52 | 3 |
| 15 | Intermediate 3 | 5-[4-(Imidazo[1,2-a]pyridine-6-carbonyl)-piperazin-1-ylmethyl]-thiophene-2-carboxylic acid 2-trifluoromethyl-benzylamide; Trifluoroacetate | 528.24 | 0.8 | 2 |
| 16 | Intermediate 3 | 5-[4-(Pyridine-2-carbonyl)-piperazin-1-ylmethyl]-thiophene-2-carboxylic acid 2-trifluoromethyl-benzylamide; Trifluoroacetate | 489.23 | 0.91 | 2 |
| 17 | Intermediate 3 | 5-[4-(2-Phenoxy-acetyl)-piperazin-1-ylmethyl]-thiophene-2-carboxylic acid 2-trifluoromethyl-benzylamide; Trifluoroacetate | 518.22 | 1 | 2 |
| 18 | Intermediate 3 | 5-[4-(4-Bromo-thiophene-3-carbonyl)-piperazin-1-ylmethyl]-thiophene-2-carboxylic acid 2-trifluoromethyl-benzylamide; Trifluoroacetate | 572.11 | 1.01 | 2 |
| 19 | Intermediate 1 | 5-[4-(Pyrrolidine-1-carbonyl)-piperazin-1-ylmethyl]-thiophene-2-carboxylic acid 2-trifluoromethoxy-benzylamide | 497.26 | 1.04 | 2 |
| 20 | Intermediate 2 | 5-[4-(2-Hydroxy-propionyl)-piperazin-1-ylmethyl]-thiophene-2-carboxylic acid 2,4-dichloro-benzylamide; Trifluoroacetate | 456.3 | 1.33 | 3 |
| 21 | Intermediate 7 | 5-[4-(4-Hydroxy-6-methoxymethyl-pyrimidin-2-yl)-piperazin-1-ylmethyl]-thiophene-2-carboxylic acid 2,4-dichloro-benzylamide; Trifluoroacetate | 522.19 | 1.6 | 3 |
| 22 | Intermediate 8 | 5-[4-(6-Hydroxy-pyridazin-3-yl)-piperazin-1-ylmethyl]-thiophene-2-carboxylic acid 4-methoxy-2-trifluoromethoxy-benzylamide; Trifluoroacetate | 524.25 | 1.5 | 3 |
| 23 | Intermediate 6 | 5-[4-(2,4-Dimethyl-6-oxo-6H-pyran-3-carbonyl)-piperazin-1-ylmethyl]-thiophene-2-carboxylic acid (indan-1-ylmethyl)-amide | 506.11 | 1.08 | 2 |
| 24 | Intermediate 10 | 5-[4-(2,4-Dimethyl-6-oxo-6H-pyran-3-carbonyl)-piperazin-1-ylmethyl]-4-methyl-thiophene-2-carboxylic acid 2-trifluoromethoxy-benzylamide | 564.07 | 1.14 | 2 |
| 25 | Intermediate 3 | 5-[4-(5-tert-Butyl-2-methyl-2H-pyrazole-3-carbonyl)-piperazin-1-ylmethyl]-thiophene-2-carboxylic acid 2-trifluoromethyl-benzylamide; Trifluoroacetate | 548.28 | 1.06 | 2 |
| 26 | Intermediate 9 | 5-(3',6'-Dimethyl-2,3,5,6-tetrahydro-[1,2']bipyrazinyl-4-ylmethyl)-thiophene-2-carboxylic acid 2-trifluoromethoxy-benzylamide | 506.3 | 1.62 | 3 |
| 27 | Intermediate 7 | 5-(4-Cyclobutyl-piperazin-1-ylmethyl)-thiophene-2-carboxylic acid 2,4-dichloro-benzylamide | 438.22 | 1.6 | 3 |

-continued

| No | Starting compound | Chemical name | Mass (from LC/MS) | R$_t$ (from LC/MS) (min) | LC/MS Method |
|---|---|---|---|---|---|
| 28 | Intermediate 10 | 5-[4-(2,4-Dimethyl-6-oxo-6H-pyran-3-carbonyl)-piperazin-1-ylmethyl]-4-methyl-thiophene-2-carboxylic acid (3,3-dimethyl-butyl)-amide; Trifluoroacetate | 474.53 | 1.48 | 3 |
| 29 | Intermediate 10 | 5-[4-(2,4-Dimethyl-6-oxo-6H-pyran-3-carbonyl)-piperazin-1-ylmethyl]-4-methyl-thiophene-2-carboxylic acid (2,3-dihydro-benzo[1,4]dioxin-5-ylmethyl)-amide; Trifluoroacetate | 538.26 | 1.36 | 3 |
| 31 | Intermediate 3 | 5-{4-[2-(3-Trifluoromethyl-phenyl)-acetyl]-piperazin-1-ylmethyl}-thiophene-2-carboxylic acid 2-trifluoromethyl-benzylamide; Trifluoroacetate | 570.26 | 1.06 | 2 |
| 32 | Intermediate 11 | 5-[4-(2-Hydroxy-propionyl)-piperazin-1-ylmethyl]-thiophene-2-carboxylic acid 4-methoxy-2-trifluoromethoxy-benzylamide | 502.2 | 1.38 | 3 |
| 33 | Intermediate 6 | 5-[4-(2,4-Dimethyl-6-oxo-6H-pyran-3-carbonyl)-piperazin-1-ylmethyl]-thiophene-2-carboxylic acid 4-trifluoromethyl-benzylamide | 534.06 | 1.09 | 2 |
| 34 | Intermediate 6 | 5-[4-(2,4-Dimethyl-6-oxo-6H-pyran-3-carbonyl)-piperazin-1-ylmethyl]-thiophene-2-carboxylic acid (2-methoxy-pyridin-4-ylmethyl)-amide | 497.07 | 0.89 | 2 |
| 35 | Intermediate 6 | 5-[4-(2,4-Dimethyl-6-oxo-6H-pyran-3-carbonyl)-piperazin-1-ylmethyl]-thiophene-2-carboxylic acid 2-trifluoromethoxy-benzylamide | 550.13 | 3.33 | 4 |
| 36 | Intermediate 6 | 5-[4-(2,4-Dimethyl-6-oxo-6H-pyran-3-carbonyl)-piperazin-1-ylmethyl]-thiophene-2-carboxylic acid 2-trifluoromethyl-benzylamide; Trifluoroacetate | 534.06 | 1.08 | 2 |
| 37 | Intermediate 1 | 5-[4-(1-Hydroxy-cyclopropanecarbonyl)-piperazin-1-ylmethyl]-thiophene-2-carboxylic acid 2-trifluoromethoxy-benzylamide; Trifluoroacetate | 484.23 | 1.02 | 2 |
| 38 | Intermediate 9 | 5-(4-Cyclopentyl-3-oxo-piperazin-1-ylmethyl)-thiophene-2-carboxylic acid 2-trifluoromethoxy-benzylamide | 482.28 | 1.9 | 3 |
| 39 | Intermediate 9 | 5-(6'-Methyl-2,3,5,6-tetrahydro-[1,2']bipyrazinyl-4-ylmethyl)-thiophene-2-carboxylic acid 2-trifluoromethoxy-benzylamide | 490.29 | 1.62 | 3 |
| 40 | Intermediate 5 | 5-[4-(2,2-Dimethyl-5-oxo-tetrahydro-furan-3-carbonyl)-piperazin-1-ylmethyl]-thiophene-2-carboxylic acid (2-methoxy-pyridin-4-ylmethyl)-amide | 487.29 | 1.25 | 3 |
| 41 | Intermediate 1 | 5-[4-((2S,3R)-3-Hydroxy-2-methylamino-butyryl)-piperazin-1-ylmethyl]-thiophene-2-carboxylic acid 2-trifluoromethoxy-benzylamide; Trifluoroacetate | 515.21 | 1.25 | 3 |
| 42 | Intermediate 2 | 5-[4-(2-Phenoxy-acetyl)-piperazin-1-ylmethyl]-thiophene-2-carboxylic acid 2,4-dichloro-benzylamide; Trifluoroacetate | 518.17 | 1.03 | 2 |
| 43 | Intermediate 2 | 5-[4-(2-Chloro-4-fluoro-benzoyl)-piperazin-1-ylmethyl]-thiophene-2-carboxylic acid 2,4-dichloro-benzylamide; Trifluoroacetate | 540.1 | 1.08 | 2 |
| 44 | Intermediate 1 | 5-[4-(1-Methyl-5-oxo-pyrrolidine-3-carbonyl)-piperazin-1-ylmethyl]-thiophene-2-carboxylic acid 2-trifluoromethoxy-benzylamide; Trifluoroacetate | 525.27 | 1 | 2 |
| 45 | Intermediate 3 | 5-[4-(Isoquinoline-1-carbonyl)-piperazin-1-ylmethyl]-thiophene-2-carboxylic acid 2-trifluoromethyl-benzylamide; Trifluoroacetate | 539.25 | 1 | 2 |
| 46 | Intermediate 3 | 5-[4-(2,4-Dimethyl-6-oxo-6H-pyran-3-carbonyl)-piperazin-1-ylmethyl]-thiophene-2-carboxylic acid 2-trifluoromethyl-benzylamide; Trifluoroacetate | 534.06 | 1.08 | 2 |
| 47 | Intermediate 9 | 5-(3-Oxo-4-thiazol-2-yl-piperazin-1-ylmethyl)-thiophene-2-carboxylic acid 2-trifluoromethoxy-benzylamide; Trifluoroacetate | 497.16 | 1.94 | 3 |

-continued

| No | Starting compound | Chemical name | Mass (from LC/MS) | R$_t$ (from LC/MS) (min) | LC/MS Method |
|---|---|---|---|---|---|
| 48 | Intermediate 2 | 5-[4-(2-Amino-3-fluoro-propionyl)-piperazin-1-ylmethyl]-thiophene-2-carboxylic acid 2,4-dichloro-benzylamide; Trifluoroacetate | 473.14 | 1.27 | 3 |
| 49 | Intermediate 1 | 5-[4-(Morpholine-3-carbonyl)-piperazin-1-ylmethyl]-thiophene-2-carboxylic acid 2-trifluoromethoxy-benzylamide; Trifluoroacetate | 513.2 | 1.25 | 3 |
| 50 | Intermediate 7 | 5-[4-(6-Hydroxy-pyridazin-3-yl)-piperazin-1-ylmethyl]-thiophene-2-carboxylic acid 2,4-dichloro-benzylamide; Trifluoroacetate | 478.16 | 1.48 | 3 |
| 51 | Intermediate 3 | 5-[4-(1-Methyl-1H-pyrrole-2-carbonyl)-piperazin-1-ylmethyl]-thiophene-2-carboxylic acid 2-trifluoromethyl-benzylamide; Trifluoroacetate | 491.21 | 0.95 | 2 |
| 52 | Intermediate 3 | 5-[4-(4-Bromo-2-methyl-2H-pyrazole-3-carbonyl)-piperazin-1-ylmethyl]-thiophene-2-carboxylic acid 2-trifluoromethyl-benzylamide; Trifluoroacetate | 570.15 | 1.02 | 2 |
| 53 | Intermediate 3 | 5-[4-(2-Ethoxy-benzoyl)-piperazin-1-ylmethyl]-thiophene-2-carboxylic acid 2-trifluoromethyl-benzylamide; Trifluoroacetate | 532.24 | 1.01 | 2 |
| 55 | Intermediate 1 | 5-[4-(Tetrahydro-furan-3-carbonyl)-piperazin-1-ylmethyl]-thiophene-2-carboxylic acid 2-trifluoromethoxy-benzylamide; Trifluoroacetate | 498.25 | 1.02 | 2 |
| 56 | Intermediate 8 | 5-[3-Oxo-4-(2,2,2-trifluoro-ethyl)-piperazin-1-ylmethyl]-thiophene-2-carboxylic acid 4-methoxy-2-trifluoro-methoxy-benzylamide; Trifluoroacetate | 526.19 | 1.91 | 3 |
| 57 | Intermediate 3 | 5-[4-(2-Methoxy-pyridine-3-carbonyl)-piperazin-1-ylmethyl]-thiophene-2-carboxylic acid 2-trifluoromethyl-benzylamide; Trifluoroacetate | 519.22 | 0.95 | 2 |
| 58 | Intermediate 2 | 5-[4-(1-Phenyl-cyclopropanecarbonyl)-piperazin-1-ylmethyl]-thiophene-2-carboxylic acid 2,4-dichloro-benzyl-amide; Trifluoroacetate | 528.19 | 1.05 | 2 |
| 59 | Intermediate 2 | 5-[4-(2,4-Dimethyl-6-oxo-6H-pyran-3-carbonyl)-piperazin-1-ylmethyl]-thiophene-2-carboxylic acid 2,4-dichloro-benzylamide | 534.03 | 3.4 | 4 |
| 61 | Intermediate 11 | 5-[4-(2-Hydroxy-propionyl)-piperazin-1-ylmethyl]-thiophene-2-carboxylic acid 2-chloro-4-cyano-benzylamide | 447.2 | 1.15 | 3 |
| 62 | Intermediate 9 | 5-(2,2-Dimethyl-3-oxo-piperazin-1-ylmethyl)-thiophene-2-carboxylic acid 2-trifluoromethoxy-benzylamide; Trifluoroacetate | 442.21 | 1.76 | 3 |
| 63 | Intermediate 2 | 5-[4-(2-Phenyl-propionyl)-piperazin-1-ylmethyl]-thiophene-2-carboxylic acid 2,4-dichloro-benzylamide; Trifluoroacetate | 516.22 | 1.04 | 2 |
| 64 | Intermediate 3 | 5-[4-(2-Chloro-4-fluoro-benzoyl)-piperazin-1-ylmethyl]-thiophene-2-carboxylic acid 2-trifluoromethyl-benzylamide; Trifluoroacetate | 540.17 | 1.05 | 2 |
| 65 | Intermediate 2 | 5-[4-(Isoquinoline-1-carbonyl)-piperazin-1-ylmethyl]-thiophene-2-carboxylic acid 2,4-dichloro-benzylamide; Trifluoroacetate | 539.19 | 1.03 | 2 |
| 66 | Intermediate 1 | 5-[4-(2-Oxo-1,2-dihydro-pyridine-3-carbonyl)-piperazin-1-ylmethyl]-thiophene-2-carboxylic acid 2-trifluoromethoxy-benzylamide; Trifluoroacetate | 521.25 | 0.99 | 2 |
| 67 | Intermediate 1 | 5-[4-(3,6-Dimethoxy-pyridine-2-carbonyl)-piperazin-1-ylmethyl]-thiophene-2-carboxylic acid 2-trifluoromethoxy-benzylamide; Trifluoroacetate | 565.28 | 1.1 | 2 |

| No | Starting compound | Chemical name | Mass (from LC/MS) | R$_t$ (from LC/MS) (min) | LC/MS Method |
|---|---|---|---|---|---|
| 68 | Intermediate 1 | 5-[4-(1-Methoxymethyl-cyclopropanecarbonyl)-piperazin-1-ylmethyl]-thiophene-2-carboxylic acid 2-trifluoromethoxy-benzylamide; Trifluoroacetate | 512.26 | 1.05 | 2 |
| 69 | Intermediate 2 | 5-{4-[2-(2-Chloro-phenyl)-acetyl]-piperazin-1-ylmethyl}-thiophene-2-carboxylic acid 2,4-dichloro-benzylamide; Trifluoroacetate | 536.13 | 1.05 | 2 |
| 70 | Intermediate 2 | 5-[4-(Bicyclo[4.2.0]octa-1(6),2,4-triene-7-carbonyl)-piperazin-1-ylmethyl]-thiophene-2-carboxylic acid 2,4-dichloro-benzylamide; Trifluoroacetate | 514.13 | 1.04 | 2 |
| 71 | Intermediate 2 | 5-[4-((1R,2R)-2-Phenyl-cyclopropanecarbonyl)-piperazin-1-ylmethyl]-thiophene-2-carboxylic acid 2,4-dichloro-benzylamide; Trifluoroacetate | 528.19 | 1.05 | 2 |
| 72 | Intermediate 1 | 5-[4-(6-Methyl-pyridine-2-carbonyl)-piperazin-1-ylmethyl]-thiophene-2-carboxylic acid 2-trifluoromethoxy-benzylamide; Trifluoroacetate | 519.26 | 1.07 | 2 |
| 73 | Intermediate 9 | 5-(2,3,5,6-Tetrahydro-[1,2']bipyrazinyl-4-ylmethyl)-thiophene-2-carboxylic acid 2-trifluoromethoxy-benzylamide | 478.27 | 1.57 | 3 |
| 74 | Intermediate 8 | 2-{4-[5-(4-Methoxy-2-trifluoromethoxy-benzylcarbamoyl)-thiophen-2-ylmethyl]-piperazin-1-yl}-N-methyl-nicotinamide; Trifluoroacetate | 564.3 | 1.56 | 3 |
| 75 | Intermediate 3 | 5-[4-(1-Phenyl-cyclopropanecarbonyl)-piperazin-1-ylmethyl]-thiophene-2-carboxylic acid 2-trifluoromethyl-benzylamide; Trifluoroacetate | 528.29 | 1.02 | 2 |
| 76 | Intermediate 3 | 5-[4-((1R,2R)-2-Phenyl-cyclopropanecarbonyl)-piperazin-1-ylmethyl]-thiophene-2-carboxylic acid 2-trifluoromethyl-benzylamide; Trifluoroacetate | 528.28 | 1.03 | 2 |
| 77 | Intermediate 2 | 5-[4-(Pyridine-2-carbonyl)-piperazin-1-ylmethyl]-thiophene-2-carboxylic acid 2,4-dichloro-benzylamide; Trifluoroacetate | 489.12 | 0.94 | 2 |
| 78 | Intermediate 6 | 5-[4-(2,4-Dimethyl-6-oxo-6H-pyran-3-carbonyl)-piperazin-1-ylmethyl]-thiophene-2-carboxylic acid (2-propyl-2H-pyrazol-3-ylmethyl)-amide | 498.12 | 0.9 | 2 |
| 79 | Intermediate 1 | 5-[4-(3-Hydroxy-6-methyl-pyridine-2-carbonyl)-piperazin-1-ylmethyl]-thiophene-2-carboxylic acid 2-trifluoromethoxy-benzylamide; Trifluoroacetate | 535.15 | 3.11 | 4 |
| 80 | Intermediate 6 | 5-[4-(2,4-Dimethyl-6-oxo-6H-pyran-3-carbonyl)-piperazin-1-ylmethyl]-thiophene-2-carboxylic acid 2-chloro-4-cyano-benzylamide | 525.22 | 1.02 | 2 |
| 81 | Intermediate 3 | 5-[4-(2,6-Dichloro-benzoyl)-piperazin-1-ylmethyl]-thiophene-2-carboxylic acid 2-trifluoromethyl-benzylamide; Trifluoroacetate | 556.15 | 1.08 | 2 |
| 82 | Intermediate 1 | 5-[4-(3-Hydroxy-pyridine-2-carbonyl)-piperazin-1-ylmethyl]-thiophene-2-carboxylic acid 2-trifluoromethoxy-benzylamide; Trifluoroacetate | 521.24 | 1.03 | 2 |
| 83 | Intermediate 1 | 5-{4-[2-(2-Methoxy-ethoxy)-acetyl]-piperazin-1-ylmethyl}-thiophene-2-carboxylic acid 2-trifluoromethoxy-benzylamide; Trifluoroacetate | 516.27 | 1.03 | 2 |
| 84 | Intermediate 7 | 5-(4-Cyclopentyl-3-oxo-piperazin-1-ylmethyl)-thiophene-2-carboxylic acid 2,4-dichloro-benzylamide | 466.24 | 4.25 | 4 |
| 85 | Intermediate 9 | 5-[4-(1,1-Dioxo-tetrahydro-1lambda6-thiophen-3-yl)-piperazin-1-ylmethyl]-thiophene-2-carboxylic acid 2-trifluoromethoxy-benzylamide; Trifluoroacetate | 518.22 | 1.5 | 3 |

-continued

| No | Starting compound | Chemical name | Mass (from LC/MS) | R_t (from LC/MS) (min) | LC/MS Method |
|---|---|---|---|---|---|
| 86 | Intermediate 1 | 5-[4-((S)-5,5-Dimethyl-pyrrolidine-2-carbonyl)-piperazin-1-ylmethyl]-thiophene-2-carboxylic acid 2-trifluoromethoxy-benzylamide; Trifluoroacetate | 525.25 | 1.32 | 3 |
| 87 | Intermediate 9 | 5-[4-(5-Hydroxymethyl-pyridin-2-yl)-piperazin-1-ylmethyl]-thiophene-2-carboxylic acid 2-trifluoromethoxy-benzylamide; Trifluoroacetate | 507.23 | 1.48 | 3 |
| 88 | Intermediate 3 | 5-[4-(3,5-Dimethyl-isoxazole-4-carbonyl)-piperazin-1-ylmethyl]-thiophene-2-carboxylic acid 2-trifluoromethyl-benzylamide; Trifluoroacetate | 507.21 | 0.96 | 2 |
| 89 | Intermediate 23 | 5-[4-(Pyridine-3-carbonyl)-piperazin-1-ylmethyl]-thiophene-2-carboxylic acid 2,4-dichloro-benzylamide; Trifluoroacetate | 489.15 | 0.92 | 2 |
| 90 | Intermediate 2 | 5-[4-(5-Ethyl-isoxazole-4-carbonyl)-piperazin-1-ylmethyl]-thiophene-2-carboxylic acid 2,4-dichloro-benzylamide; Trifluoroacetate | 507.13 | 1.01 | 2 |
| 91 | Intermediate 2 | 5-[4-(2,4-Dimethyl-6-oxo-6H-pyran-3-carbonyl)-piperazin-1-ylmethyl]-thiophene-2-carboxylic acid 2,3-dichloro-benzylamide | 534 | 1.1 | 2 |
| 92 | Intermediate 6 | 5-[4-(3-Hydroxy-butyryl)-piperazin-1-ylmethyl]-thiophene-2-carboxylic acid 2-trifluoromethoxy-benzylamide; Trifluoroacetate | 486.25 | 1 | 2 |
| 93 | Intermediate 1 | 5-[4-((R)-2-Methoxy-propionyl)-piperazin-1-ylmethyl]-thiophene-2-carboxylic acid 2-trifluoromethoxy-benzylamide; Trifluoroacetate | 486.25 | 1.04 | 2 |
| 94 | Intermediate 1 | 5-[4-((1R,2S)-2-Hydroxy-cyclopentanecarbonyl)-piperazin-1-ylmethyl]-thiophene-2-carboxylic acid 2-trifluoromethoxy-benzylamide; Trifluoroacetate | 512.28 | 1.04 | 2 |
| 95 | Intermediate 1 | 5-[4-(2-Hydroxy-2-methyl-butyryl)-piperazin-1-ylmethyl]-thiophene-2-carboxylic acid 2-trifluoromethoxy-benzylamide; Trifluoroacetate | 500.28 | 1.05 | 2 |
| 96 | Intermediate 1 | 5-[4-((R)-2-Hydroxy-butyryl)-piperazin-1-ylmethyl]-thiophene-2-carboxylic acid 2-trifluoromethoxy-benzylamide; Trifluoroacetate | 486.25 | 1.03 | 2 |
| 97 | Intermediate 1 | 5-[4-(3-Methoxy-pyridine-2-carbonyl)-piperazin-1-ylmethyl]-thiophene-2-carboxylic acid 2-trifluoromethoxy-benzylamide; Trifluoroacetate | 535.27 | 1.05 | 2 |
| 98 | Intermediate 3 | 5-[4-(2-Phenyl-propionyl)-piperazin-1-ylmethyl]-thiophene-2-carboxylic acid 2-trifluoromethyl-benzylamide; Trifluoroacetate | 516.25 | 1.01 | 2 |
| 99 | Intermediate 4 | 5-[4-(4-Bromo-2-ethyl-5-methyl-2H-pyrazole-3-carbonyl)-piperazin-1-ylmethyl]-thiophene-2-carboxylic acid (3-methyl-butyl)-amide | 510.15 | 1.16 | 2 |
| 100 | Intermediate 2 | 5-{4-[2-(3-Trifluoromethyl-phenyl)-acetyl]-piperazin-1-ylmethyl}-thiophene-2-carboxylic acid 2,4-dichloro-benzylamide; Trifluoroacetate | 570.18 | 1.08 | 2 |
| 101 | Intermediate 1 | 5-[4-((R)-2-Hydroxy-3-methyl-butyryl)-piperazin-1-ylmethyl]-thiophene-2-carboxylic acid 2-trifluoromethoxy-benzylamide; Trifluoroacetate | 500.29 | 1.07 | 2 |
| 102 | Intermediate 1 | 5-[4-(5-Oxo-pyrrolidine-2-carbonyl)-piperazin-1-ylmethyl]-thiophene-2-carboxylic acid 2-trifluoromethoxy-benzylamide; Trifluoroacetate | 511.17 | 1.33 | 3 |
| 103 | Intermediate 2 | 5-[4-((S)-5,5-Dimethyl-thiazolidine-4-carbonyl)-piperazin-1-ylmethyl]-thiophene-2-carboxylic acid 2,4-dichloro-benzylamide; Trifluoroacetate | 527.17 | 1.49 | 3 |

| No | Starting compound | Chemical name | Mass (from LC/MS) | R_t (from LC/MS) (min) | LC/MS Method |
|---|---|---|---|---|---|
| 104 | Intermediate 8 | 5-(5,6-Dihydro-8H-[1,2,4]triazolo[4,3-a]pyrazin-7-ylmethyl)-thiophene-2-carboxylic acid 4-methoxy-2-trifluoromethoxy-benzylamide; Trifluoroacetate | 468.23 | 1.56 | 3 |
| 105 | Intermediate 7 | 5-[4-(3-Methyl-pyridin-2-yl)-3-oxo-piperazin-1-ylmethyl]-thiophene-2-carboxylic acid 2,4-dichloro-benzylamide; Trifluoroacetate | 489.18 | 1.85 | 3 |
| 106 | Intermediate 1 | 5-[4-(3-Hydroxy-propionyl)-piperazin-1-ylmethyl]-thiophene-2-carboxylic acid 2-trifluoromethoxy-benzylamide; Trifluoroacetate | 472.23 | 0.98 | 2 |
| 107 | Intermediate 1 | 5-[4-(4-Oxo-1,4-dihydro-pyrimidine-5-carbonyl)-piperazin-1-ylmethyl]-thiophene-2-carboxylic acid 2-trifluoromethoxy-benzylamide; Trifluoroacetate | 522.22 | 0.98 | 2 |
| 108 | Intermediate 2 | 5-[4-(1-Methyl-6-oxo-1,6-dihydro-pyridazin-4-yl)-piperazin-1-ylmethyl]-thiophene-2-carboxylic acid 2,4-dichloro-benzylamide | 492.17 | 3.07 | 4 |
| 109 | Intermediate 2 | 5-[4-(1-Amino-cyclopropanecarbonyl)-piperazin-1-ylmethyl]-thiophene-2-carboxylic acid 2,4-dichloro-benzylamide; Trifluoroacetate | 467.21 | 1.4 | 3 |
| 110 | Intermediate 1 | 5-[4-((S)-5,5-Dimethyl-thiazolidine-4-carbonyl)-piperazin-1-ylmethyl]-thiophene-2-carboxylic acid 2-trifluoromethoxy-benzylamide; Trifluoroacetate | 543.23 | 1.47 | 3 |
| 111 | Intermediate 9 | 5-[3-Oxo-4-(2,2,2-trifluoro-ethyl)-piperazin-1-ylmethyl]-thiophene-2-carboxylic acid 2-trifluoromethoxy-benzylamide; Trifluoroacetate | 496.17 | 1.9 | 3 |
| 112 | Intermediate 9 | 5-[4-(3-Methyl-pyridin-2-yl)-3-oxo-piperazin-1-ylmethyl]-thiophene-2-carboxylic acid 2-trifluoromethoxy-benzylamide; Trifluoroacetate | 505.24 | 1.81 | 3 |
| 113 | Intermediate 8 | 5-[4-(1-Methyl-1H-imidazol-2-yl)-piperazin-1-ylmethyl]-thiophene-2-carboxylic acid 4-methoxy-2-trifluoromethoxy-benzylamide; Trifluoroacetate | 510.26 | 1.44 | 3 |
| 114 | Intermediate 7 | 5-(6-Oxo-hexahydro-pyrrolo[1,2-a]pyrazin-2-ylmethyl)-thiophene-2-carboxylic acid 2,4-dichloro-benzylamide | 438.18 | 1.58 | 3 |
| 116 | Intermediate 1 | 5-[4-(3-Methoxy-propionyl)-piperazin-1-ylmethyl]-thiophene-2-carboxylic acid 2-trifluoromethoxy-benzylamide; Trifluoroacetate | 486.25 | 1.02 | 2 |
| 117 | Intermediate 3 | 5-[4-(5-Ethyl-isoxazole-4-carbonyl)-piperazin-1-ylmethyl]-thiophene-2-carboxylic acid 2-trifluoromethyl-benzylamide; Trifluoroacetate | 507.21 | 0.98 | 2 |
| 118 | Intermediate 4 | 5-[4-(2-Ethoxy-benzoyl)-piperazin-1-ylmethyl]-thiophene-2-carboxylic acid (3-methyl-butyl)-amide | 444.14 | 1.09 | 2 |
| 119 | Intermediate 3 | 5-[4-(2-Fluoro-benzoyl)-piperazin-1-ylmethyl]-thiophene-2-carboxylic acid 2-trifluoromethyl-benzylamide; Trifluoroacetate | 506.18 | 1 | 2 |
| 121 | Intermediate 1 | 5-[4-(Pyridine-2-carbonyl)-piperazin-1-ylmethyl]-thiophene-2-carboxylic acid 2-trifluoromethoxy-benzylamide; Trifluoroacetate | 505.22 | 1.05 | 2 |
| 122 | Intermediate 1 | 5-[4-(3,5-Dimethyl-isoxazole-4-carbonyl)-piperazin-1-ylmethyl]-thiophene-2-carboxylic acid 2-trifluoromethoxy-benzylamide; Trifluoroacetate | 523.25 | 1.1 | 2 |
| 123 | Intermediate 1 | 5-[4-(2-Hydroxy-2-methyl-propionyl)-piperazin-1-ylmethyl]-thiophene-2-carboxylic acid 2-trifluoromethoxy-benzylamide; Trifluoroacetate | 486.25 | 1.01 | 2 |

-continued

| No | Starting compound | Chemical name | Mass (from LC/MS) | R$_t$ (from LC/MS) (min) | LC/MS Method |
|---|---|---|---|---|---|
| 124 | Intermediate 8 | 5-(4-Pyridin-2-yl-piperazin-1-ylmethyl)-thiophene-2-carboxylic acid 4-methoxy-2-trifluoromethoxy-benzylamide; Trifluoroacetate | 507.26 | 1.57 | 3 |
| 125 | Intermediate 9 | 5-[4-(2-Hydroxy-ethyl)-piperazin-1-ylmethyl]-thiophene-2-carboxylic acid 2-trifluoromethoxy-benzylamide; Trifluoroacetate | 444.25 | 1.5 | 3 |
| 126 | Intermediate 8 | 5-[4-(3-Methyl-pyridin-2-yl)-3-oxo-piperazin-1-ylmethyl]-thiophene-2-carboxylic acid 4-methoxy-2-trifluoromethoxy-benzylamide; Trifluoroacetate | 535.28 | 1.82 | 3 |
| 127 | Intermediate 8 | 5-[4-(4-Methyl-pyridin-2-yl)-piperazin-1-ylmethyl]-thiophene-2-carboxylic acid 4-methoxy-2-trifluoromethoxy-benzylamide; Trifluoroacetate | 521.29 | 1.57 | 3 |
| 128 | Intermediate 1 | 5-[4-(3-Hydroxy-3-methyl-butyryl)-piperazin-1-ylmethyl]-thiophene-2-carboxylic acid 2-trifluoromethoxy-benzylamide; Trifluoroacetate | 500.27 | 1.03 | 2 |
| 129 | Intermediate 8 | 5-[4-(3,6-Difluoro-pyridine-2-carbonyl)-piperazin-1-ylmethyl]-thiophene-2-carboxylic acid 2-trifluoromethoxy-benzylamide; Trifluoroacetate | 541.24 | 1.12 | 2 |
| 130 | Intermediate 2 | 5-[4-(1-Methyl-1H-pyrrole-2-carbonyl)-piperazin-1-ylmethyl]-thiophene-2-carboxylic acid 2,4-dichloro-benzylamide; Trifluoroacetate | 491.14 | 0.98 | 2 |
| 131 | Intermediate 2 | 5-[4-(2-Fluoro-benzoyl)-piperazin-1-ylmethyl]-thiophene-2-carboxylic acid 2,4-dichloro-benzylamide; Trifluoroacetate | 506.14 | 1.03 | 2 |
| 132 | Intermediate 1 | 5-[4-(6-Hydroxy-pyridine-2-carbonyl)-piperazin-1-ylmethyl]-thiophene-2-carboxylic acid 2-trifluoromethoxy-benzylamide; Trifluoroacetate | 521.24 | 1.02 | 2 |
| 133 | Intermediate 2 | 5-[4-(4-Amino-tetrahydro-pyran-4-carbonyl)-piperazin-1-ylmethyl]-thiophene-2-carboxylic acid 2,4-dichloro-benzylamide; Trifluoroacetate | 511.17 | 1.28 | 3 |
| 134 | Intermediate 8 | 5-(4-Methyl-3-oxo-piperazin-1-ylmethyl)-thiophene-2-carboxylic acid 4-methoxy-2-trifluoromethoxy-benzylamide; Trifluoroacetate | 458.2 | 1.69 | 3 |
| 135 | Intermediate 9 | N-Methyl-2-{4-[5-(2-trifluoromethoxy-benzylcarbamoyl)-thiophen-2-ylmethyl]-piperazin-1-yl}-nicotinamide; Trifluoroacetate | 534.28 | 1.53 | 3 |
| 136 | Intermediate 9 | 5-[4-(6-Hydroxy-pyridazin-3-yl)-piperazin-1-ylmethyl]-thiophene-2-carboxylic acid 2-trifluoromethoxy-benzylamide; Trifluoroacetate | 494.21 | 1.46 | 3 |
| 137 | Intermediate 1 | 5-[4-(3-Methylsulfanyl-propionyl)-piperazin-1-ylmethyl]-thiophene-2-carboxylic acid 2-trifluoromethoxy-benzylamide; Trifluoroacetate | 502.22 | 1.07 | 2 |
| 138 | Intermediate 1 | 5-[4-(2-Dimethylamino-propionyl)-piperazin-1-ylmethyl]-thiophene-2-carboxylic acid 2-trifluoromethoxy-benzylamide; Trifluoroacetate | 499.28 | 0.95 | 2 |
| 140 | Intermediate 1 | 5-[4-(4-Methoxy-butyryl)-piperazin-1-ylmethyl]-thiophene-2-carboxylic acid 2-trifluoromethoxy-benzylamide | 500.27 | 1.04 | 2 |
| 141 | Intermediate 1 | 5-(4-Cyclopropanecarbonyl-piperazin-1-ylmethyl)-thiophene-2-carboxylic acid 2-trifluoromethoxy-benzylamide; Trifluoroacetate | 468.18 | 3.13 | 4 |
| 142 | Intermediate 9 | 5-(4-[1,3,4]Thiadiazol-2-yl-piperazin-1-ylmethyl)-thiophene-2-carboxylic acid 2-trifluoromethoxy-benzylamide; Trifluoroacetate | 484.19 | 1.57 | 3 |

| No | Starting compound | Chemical name | Mass (from LC/MS) | R$_t$ (from LC/MS) (min) | LC/MS Method |
|---|---|---|---|---|---|
| 143 | Intermediate 1 | 5-[4-(1-Amino-cyclobutanecarbonyl)-piperazin-1-ylmethyl]-thiophene-2-carboxylic acid 2-trifluoromethoxy-benzylamide; Trifluoroacetate | 497.19 | 1.26 | 3 |
| 144 | Intermediate 1 | 5-[4-(2-Amino-3-fluoro-propionyl)-piperazin-1-ylmethyl]-thiophene-2-carboxylic acid 2-trifluoromethoxy-benzylamide; Trifluoroacetate | 489.18 | 1.24 | 3 |
| 145 | Intermediate 1 | 5-[4-(4-Amino-tetrahydro-pyran-4-carbonyl)-piperazin-1-ylmethyl]-thiophene-2-carboxylic acid 2-trifluoromethoxy-benzylamide; Trifluoroacetate | 527.21 | 1.25 | 3 |
| 146 | Intermediate 8 | 5-[4-(5-Hydroxymethyl-pyridin-2-yl)-piperazin-1-ylmethyl]-thiophene-2-carboxylic acid 4-methoxy-2-trifluoromethoxy-benzylamide; Trifluoroacetate | 537.28 | 1.52 | 3 |
| 147 | Intermediate 10 | 5-[4-([1,4]Dioxane-2-carbonyl)-piperazin-1-ylmethyl]-thiophene-2-carboxylic acid 2-trifluoromethoxy-benzylamide; Trifluoroacetate | 514.26 | 1.03 | 2 |
| 148 | Intermediate 6 | 5-[4-(2,4-Dimethyl-6-oxo-6H-pyran-3-carbonyl)-piperazin-1-ylmethyl]-4-methyl-thiophene-2-carboxylic acid 2-trifluoromethoxy-benzylamide | 564.07 | 1.14 | 2 |
| 150 | Intermediate 3 | 5-[4-(2,4-Dimethyl-6-oxo-6H-pyran-3-carbonyl)-piperazin-1-ylmethyl]-thiophene-2-carboxylic acid 2-difluoromethoxy-benzylamide | 532.07 | 1.04 | 2 |
| 151 | Intermediate 3 | 5-[4-(Pyrazolo[1,5-a]pyridine-3-carbonyl)-piperazin-1-ylmethyl]-thiophene-2-carboxylic acid 2-trifluoromethyl-benzylamide; Trifluoroacetate | 528.24 | 0.92 | 2 |
| 152 | Intermediate 3 | 5-[4-(5-Methyl-thiophene-2-carbonyl)-piperazin-1-ylmethyl]-thiophene-2-carboxylic acid 2-trifluoromethyl-benzylamide; Trifluoroacetate | 508.18 | 1 | 2 |
| 153 | Intermediate 2 | 5-[4-((1R,2R)-2-Phenyl-cyclopropanecarbonyl)-piperazin-1-ylmethyl]-thiophene-2-carboxylic acid 2,4-dichloro-benzylamide; Trifluoroacetate | 528.19 | 1.05 | 2 |
| 154 | Intermediate 2 | 5-[4-(5-Methyl-thiophene-2-carbonyl)-piperazin-1-ylmethyl]-thiophene-2-carboxylic acid 2,4-dichloro-benzylamide; Trifluoroacetate | 508.09 | 1.03 | 2 |
| 155 | Intermediate 1 | 5-[4-(2-Hydroxy-propionyl)-piperazin-1-ylmethyl]-thiophene-2-carboxylic acid 2-trifluoromethoxy-benzylamide; Trifluoroacetate | 472.22 | 1.01 | 2 |
| 156 | Intermediate 1 | 5-{4-[2-(2-Oxo-oxazolidin-3-yl)-acetyl]-piperazin-1-ylmethyl}-thiophene-2-carboxylic acid 2-trifluoromethoxy-benzylamide; Trifluoroacetate | 527.25 | 1.01 | 2 |
| 157 | Intermediate 1 | 5-[4-(1-Amino-cyclohexanecarbonyl)-piperazin-1-ylmethyl]-thiophene-2-carboxylic acid 2-trifluoromethoxy-benzylamide; Trifluoroacetate | 525.24 | 1.31 | 3 |
| 158 | Intermediate 1 | 5-[4-(4-Hydroxy-6-methoxymethyl-pyrimidin-2-yl)-piperazin-1-ylmethyl]-thiophene-2-carboxylic acid 2-trifluoromethoxy-benzylamide; Trifluoroacetate | 538.27 | 1.56 | 3 |
| 159 | Intermediate 10 | 5-[4-(2,4-Dimethyl-6-oxo-6H-pyran-3-carbonyl)-piperazin-1-ylmethyl]-4-methyl-thiophene-2-carboxylic acid (3,3-dimethyl-butyl)-amide; Trifluoroacetate | 474.53 | 1.48 | 3 |
| 160 | Intermediate 12 | 2-[4-(3,5-Dimethyl-isoxazole-4-carbonyl)-piperazin-1-ylmethyl]-thiazole-5-carboxylic acid 2,4-dichloro-benzylamide | 508.14 | 3.85 | 4 |

| No | Starting compound | Chemical name | Mass (from LC/MS) | R_t (from LC/MS) (min) | LC/MS Method |
|---|---|---|---|---|---|
| 161 | Intermediate 12 | 2-[4-(2,2-Dimethyl-5-oxo-tetrahydro-furan-3-carbonyl)-piperazin-1-ylmethyl]-thiazole-5-carboxylic acid 2,4-dichloro-benzylamide | 525.17 | 3.71 | 4 |
| 162 | Intermediate 12 | 2-[4-(2,4-Dimethyl-6-oxo-6H-pyran-3-carbonyl)-piperazin-1-ylmethyl]-thiazole-5-carboxylic acid 2,4-dichloro-benzylamide | 535.16 | 1.65 | 3 |
| 163 | Intermediate 12 | 2-[4-(3-Hydroxy-propionyl)-piperazin-1-ylmethyl]-thiazole-5-carboxylic acid 2,4-dichloro-benzylamide | 457.19 | 1.41 | 3 |
| 164 | Intermediate 12 | 2-[4-(3-Methylsulfanyl-propionyl)-piperazin-1-ylmethyl]-thiazole-5-carboxylic acid 2,4-dichloro-benzylamide | 487.09 | 3.66 | 4 |
| 165 | Intermediate 12 | 2-{4-[2-(3,5-Dimethyl-isoxazol-4-yl)-acetyl]-piperazin-1-ylmethyl}-thiazole-5-carboxylic acid 2,4-dichloro-benzylamide | 522.13 | 3.64 | 4 |
| 166 | Intermediate 12 | 2-[4-(4-Methoxy-butyryl)-piperazin-1-ylmethyl]-thiazole-5-carboxylic acid 2,4-dichloro-benzylamide | 485.21 | 1.56 | 3 |
| 167 | Intermediate 12 | 2-[4-(2-Hydroxy-2-methyl-butyryl)-piperazin-1-ylmethyl]-thiazole-5-carboxylic acid 2,4-dichloro-benzylamide | 485.18 | 3.43 | 4 |
| 168 | Intermediate 12 | 2-{4-[2-(2-Oxo-pyrrolidin-1-yl)-acetyl]-piperazin-1-ylmethyl}-thiazole-5-carboxylic acid 2,4-dichloro-benzylamide | 510.19 | 1.49 | 3 |
| 169 | Intermediate 12 | 2-{4-[2-(2-Oxo-pyrrolidin-1-yl)-propionyl]-piperazin-1-ylmethyl}-thiazole-5-carboxylic acid 2,4-dichloro-benzylamide | 524.18 | 3.4 | 4 |
| 170 | Intermediate 12 | 2-[4-([1,4]Dioxane-2-carbonyl)-piperazin-1-ylmethyl]-thiazole-5-carboxylic acid 2,4-dichloro-benzylamide | 499.17 | 1.54 | 3 |
| 171 | Intermediate 12 | 2-(4-Cyclopropanecarbonyl-piperazin-1-ylmethyl)-thiazole-5-carboxylic acid 2,4-dichloro-benzylamide | 453.17 | 1.58 | 3 |
| 172 | Intermediate 12 | 2-[4-(2-Hydroxy-2-methyl-propionyl)-piperazin-1-ylmethyl]-thiazole-5-carboxylic acid 2,4-dichloro-benzylamide | 471.15 | 1.49 | 3 |
| 173 | Intermediate 12 | 2-[4-(3-Methoxy-propionyl)-piperazin-1-ylmethyl]-thiazole-5-carboxylic acid 2,4-dichloro-benzylamide | 471.15 | 1.52 | 3 |
| 174 | Intermediate 12 | 2-[4-(6-Methyl-pyridine-2-carbonyl)-piperazin-1-ylmethyl]-thiazole-5-carboxylic acid 2,4-dichloro-benzylamide | 504.18 | 1.63 | 3 |
| 175 | Intermediate 12 | 2-[4-(6-Hydroxy-pyridine-2-carbonyl)-piperazin-1-ylmethyl]-thiazole-5-carboxylic acid 2,4-dichloro-benzylamide | 506.18 | 1.52 | 3 |
| 176 | Intermediate 12 | 2-[4-(3-Hydroxy-2,2-dimethyl-propionyl)-piperazin-1-ylmethyl]-thiazole-5-carboxylic acid 2,4-dichloro-benzylamide | 485.19 | 1.54 | 3 |
| 178 | Intermediate 12 | 2-[4-(2-Oxo-1,2-dihydro-pyridine-3-carbonyl)-piperazin-1-ylmethyl]-thiazole-5-carboxylic acid 2,4-dichloro-benzylamide | 506.13 | 1.42 | 3 |
| 179 | Intermediate 12 | 2-[4-((R)-2-Hydroxy-butyryl)-piperazin-1-ylmethyl]-thiazole-5-carboxylic acid 2,4-dichloro-benzylamide | 471.19 | 3.47 | 4 |
| 180 | Intermediate 12 | 2-[4-(3,6-Difluoro-pyridine-2-carbonyl)-piperazin-1-ylmethyl]-thiazole-5-carboxylic acid 2,4-dichloro-benzylamide | 526.15 | 1.71 | 3 |
| 181 | Intermediate 12 | 2-[4-(2-Hydroxy-acetyl)-piperazin-1-ylmethyl]-thiazole-5-carboxylic acid 2,4-dichloro-benzylamide | 443.13 | 1.44 | 3 |
| 182 | Intermediate 12 | 2-[4-(Tetrahydro-furan-2-carbonyl)-piperazin-1-ylmethyl]-thiazole-5-carboxylic acid 2,4-dichloro-benzylamide | 483.19 | 1.56 | 3 |
| 183 | Intermediate 12 | 2-[4-(Tetrahydro-furan-3-carbonyl)-piperazin-1-ylmethyl]-thiazole-5-carboxylic acid 2,4-dichloro-benzylamide | 483.16 | 1.53 | 3 |
| 184 | Intermediate 12 | 2-[4-((S)-1-Methyl-pyrrolidine-2-carbonyl)-piperazin-1-ylmethyl]-thiazole-5-carboxylic acid 2,4-dichloro-benzylamide | 496.22 | 1.33 | 3 |

-continued

| No | Starting compound | Chemical name | Mass (from LC/MS) | R_t (from LC/MS) (min) | LC/MS Method |
|---|---|---|---|---|---|
| 185 | Intermediate 12 | 2-[4-(3-Hydroxy-3-methyl-butyryl)-piperazin-1-ylmethyl]-thiazole-5-carboxylic acid 2,4-dichloro-benzylamide | 485.19 | 1.54 | 3 |
| 186 | Intermediate 12 | 2-[4-(Pyridine-2-carbonyl)-piperazin-1-ylmethyl]-thiazole-5-carboxylic acid 2,4-dichloro-benzylamide | 490.16 | 1.58 | 3 |
| 187 | Intermediate 12 | 2-[4-(3-Hydroxy-pyridine-2-carbonyl)-piperazin-1-ylmethyl]-thiazole-5-carboxylic acid 2,4-dichloro-benzylamide | 506.16 | 1.55 | 3 |
| 188 | Intermediate 12 | 2-{4-[2-(2-Methoxy-ethoxy)-acetyl]-piperazin-1-ylmethyl}-thiazole-5-carboxylic acid 2,4-dichloro-benzylamide | 501.15 | 3.36 | 4 |
| 189 | Intermediate 12 | 2-[4-(2-Hydroxy-propionyl)-piperazin-1-ylmethyl]-thiazole-5-carboxylic acid 2,4-dichloro-benzylamide | 457.13 | 1.49 | 3 |
| 190 | Intermediate 12 | 2-[4-(1-Methyl-piperidine-4-carbonyl)-piperazin-1-ylmethyl]-thiazole-5-carboxylic acid 2,4-dichloro-benzylamide | 510.23 | 1.28 | 3 |
| 191 | Intermediate 12 | 2-[4-((S)-2-Hydroxy-butyryl)-piperazin-1-ylmethyl]-thiazole-5-carboxylic acid 2,4-dichloro-benzylamide | 471.19 | 1.57 | 3 |
| 192 | Intermediate 12 | 2-[4-(2-Methoxy-acetyl)-piperazin-1-ylmethyl]-thiazole-5-carboxylic acid 2,4-dichloro-benzylamide | 457.17 | 1.51 | 3 |
| 193 | Intermediate 12 | 2-{4-[2-(2-Oxo-oxazolidin-3-yl)-acetyl]-piperazin-1-ylmethyl}-thiazole-5-carboxylic acid 2,4-dichloro-benzylamide | 512.18 | 1.49 | 3 |
| 194 | Intermediate 12 | 2-[4-(3-Methyl-pyridine-2-carbonyl)-piperazin-1-ylmethyl]-thiazole-5-carboxylic acid 2,4-dichloro-benzylamide | 504.18 | 3.68 | 4 |
| 195 | Intermediate 12 | 2-[4-(2-Cyano-acetyl)-piperazin-1-ylmethyl]-thiazole-5-carboxylic acid 2,4-dichloro-benzylamide | 452.14 | 1.56 | 3 |
| 196 | Intermediate 12 | 2-[4-(3-Methoxy-pyridine-2-carbonyl)-piperazin-1-ylmethyl]-thiazole-5-carboxylic acid 2,4-dichloro-benzylamide | 520.2 | 1.59 | 3 |
| 197 | Intermediate 12 | 2-[4-(1-Methyl-5-oxo-pyrrolidine-3-carbonyl)-piperazin-1-ylmethyl]-thiazole-5-carboxylic acid 2,4-dichloro-benzylamide | 510.18 | 1.48 | 3 |
| 198 | Intermediate 12 | 2-[4-((R)-2-Hydroxy-3-methyl-butyryl)-piperazin-1-ylmethyl]-thiazole-5-carboxylic acid 2,4-dichloro-benzylamide | 485.19 | 1.66 | 3 |
| 199 | Intermediate 12 | 2-[4-(3-Dimethylamino-propionyl)-piperazin-1-ylmethyl]-thiazole-5-carboxylic acid 2,4-dichloro-benzylamide | 484.21 | 1.28 | 3 |
| 200 | Intermediate 12 | 2-[4-(1-Amino-cyclopropanecarbonyl)-piperazin-1-ylmethyl]-thiazole-5-carboxylic acid 2,4-dichloro-benzylamide | 468.19 | 1.31 | 3 |
| 201 | Intermediate 12 | 2-[4-(1-Hydroxy-cyclopropanecarbonyl)-piperazin-1-ylmethyl]-thiazole-5-carboxylic acid 2,4-dichloro-benzylamide | 469.18 | 1.48 | 3 |
| 202 | Intermediate 12 | 2-[4-(6-Methoxy-pyridine-2-carbonyl)-piperazin-1-ylmethyl]-thiazole-5-carboxylic acid 2,4-dichloro-benzylamide | 520.19 | 1.71 | 3 |
| 203 | Intermediate 12 | 2-[4-(2-Oxo-imidazolidine-4-carbonyl)-piperazin-1-ylmethyl]-thiazole-5-carboxylic acid 2,4-dichloro-benzylamide | 497.17 | 1.43 | 3 |
| 204 | Intermediate 12 | 2-[4-((R)-2-Methoxy-propionyl)-piperazin-1-ylmethyl]-thiazole-5-carboxylic acid 2,4-dichloro-benzylamide | 471.19 | 3.48 | 4 |
| 205 | Intermediate 12 | 2-[4-(1-Methoxymethyl-cyclopropanecarbonyl)-piperazin-1-ylmethyl]-thiazole-5-carboxylic acid 2,4-dichloro-benzylamide | 497.19 | 3.53 | 4 |
| 206 | Intermediate 12 | 2-[4-(3,5-Dimethyl-1H-pyrazole-4-carbonyl)-piperazin-1-ylmethyl]-thiazole-5-carboxylic acid 2,4-dichloro-benzylamide | 507.19 | 1.51 | 3 |
| 207 | Intermediate 12 | 2-[4-(2-Methoxy-2-methyl-propionyl)-piperazin-1-ylmethyl]-thiazole-5-carboxylic acid 2,4-dichloro-benzylamide | 485.18 | 3.7 | 4 |
| 208 | Intermediate 12 | 2-[4-(Oxetane-2-carbonyl)-piperazin-1-ylmethyl]-thiazole-5-carboxylic acid 2,4-dichloro-benzylamide | 469.18 | 1.52 | 3 |

-continued

| No | Starting compound | Chemical name | Mass (from LC/MS) | R$_t$ (from LC/MS) (min) | LC/MS Method |
|---|---|---|---|---|---|
| 209 | Intermediate 12 | 2-[4-(3-Hydroxy-cyclopentanecarbonyl)-piperazin-1-ylmethyl]-thiazole-5-carboxylic acid 2,4-dichloro-benzylamide | 497.23 | 1.47 | 3 |
| 210 | Intermediate 12 | 2-{4-[2-((S)-4-Hydroxy-2-oxo-pyrrolidin-1-yl)-acetyl]-piperazin-1-ylmethyl}-thiazole-5-carboxylic acid 2,4-dichloro-benzylamide | 526.2 | 1.41 | 3 |
| 211 | Intermediate 12 | 2-{4-[2-(3-Hydroxy-pyrrolidin-1-yl)-acetyl]-piperazin-1-ylmethyl}-thiazole-5-carboxylic acid 2,4-dichloro-benzylamide | 512.22 | 1.29 | 3 |
| 206 | Intermediate 12 | 2-[4-(3,5-Dimethyl-1H-pyrazole-4-carbonyl)-piperazin-1-ylmethyl]-thiazole-5-carboxylic acid 2,4-dichloro-benzylamide | 507.19 | 1.51 | 3 |
| 207 | Intermediate 12 | 2-[4-(2-Methoxy-2-methyl-propionyl)-piperazin-1-ylmethyl]-thiazole-5-carboxylic acid 2,4-dichloro-benzylamide | 485.18 | 3.7 | 4 |
| 208 | Intermediate 12 | 2-[4-(Oxetane-2-carbonyl)-piperazin-1-ylmethyl]-thiazole-5-carboxylic acid 2,4-dichloro-benzylamide | 469.18 | 1.52 | 3 |
| 209 | Intermediate 12 | 2-[4-(3-Hydroxy-cyclopentanecarbonyl)-piperazin-1-ylmethyl]-thiazole-5-carboxylic acid 2,4-dichloro-benzylamide | 497.23 | 1.47 | 3 |
| 210 | Intermediate 12 | 2-{4-[2-((S)-4-Hydroxy-2-oxo-pyrrolidin-1-yl)-acetyl]-piperazin-1-ylmethyl}-thiazole-5-carboxylic acid 2,4-dichloro-benzylamide | 526.2 | 1.41 | 3 |
| 211 | Intermediate 12 | 2-{4-[2-(3-Hydroxy-pyrrolidin-1-yl)-acetyl]-piperazin-1-ylmethyl}-thiazole-5-carboxylic acid 2,4-dichloro-benzylamide | 512.22 | 1.29 | 3 |

Pharmacological Testing:

The ability of the compounds of the formula I to inhibit soluble epoxide hydrolase can be determined as follows:

Compounds were tested in a biochemical screening assay using recombinant sEH purified from Sf9 insect cells and an artificial substrate, (3-phenyl-oxiranyl)-acetic acid cyano-(6-methoxy-naphtalen-2-yl)-methyl ester, Phome. The biochemical assay was performed in analogy to a fluorometric described in the literature (P. D. Jones et al., Anal. Biochem. 2005, 343, 66-75). The assay principle bases on the sEH-catalyzed hydrolysis of an artificial α-cyano-ester substrate. O-deacetylation liberates a cyanohydrin intermediate that rapidly decomposes to the highly fluorescent 6-methoxy-2-naphtaldehyde. To discriminate sample autofluorescence, the assay was carried out as a kinetic measurement with two time points. The first measurement is performed immediately before addition of the substrate and the 15 second measurement is done after completion of the assay. The assay format is either in 96- or in 384-well format.

Details of the assay using a 96-well plate format are described below. 40 µl recombinant sEH enzyme and 5 µl test compound are pre-incubated for 15 minutes at 30° C. Following pre-incubation, the reaction is started by addition of 5 µl Phome. The assay mixture containing 2 nM final sEH concentration, test compound ranging in a concentration from 0.0001-10 µM and 5 µM Phome is incubated for 60 minutes at 30° C.

Fluorescence is measured with any suitable detector for instance a TECAN Safire or Tecan Ultra at 340 nm emission and 465 nm extinction. % inhibition of recombinant sEH activity is used for calculation of corresponding IC50 values as illustrated and described in the examples.

The NCBI gene bank reference sequence with the accession number NM_001979 for EPHX2/sEH was applied for recombinant protein production:

The following commercially available materials have been used:

Incubation reagent: 25 mM Hepes (Sigma-Aldrich, Cat. No H-3375), 0.01% bovine albumin (Sigma-Aldrich Cat. No PA9205)

Substrate: 3-Phenyl-oxiranyl)-acetic acid cyano-(6-methoxy-naphtalen-2-yl)-methyl ester, Phome (Biozol Cat. No 10003134)

Microtiter plates: 96-well plates (Greiner Cat. No 655180; Costar Cat. No 3915)

The results for inhibition of soluble epoxide hydrolase are shown in Table 1.

TABLE 1

| Example | sEH IC$_{50}$ (µM) |
|---|---|
| 1 | 0.000122 |
| 2 | 0.000502 |
| 3 | 0.000407 |
| 4 | 0.000168 |
| 5 | 0.000432 |
| 6 | 0.000528 |
| 7 | 0.000524 |
| 8 | 0.000512 |
| 9 | 0.00306 |
| 10 | 0.00294 |
| 11 | 0.00295 |
| 12 | 0.0254 |
| 13 | 0.00298 |
| 14 | 0.00293 |
| 15 | 0.000604 |
| 16 | 0.000534 |
| 17 | 0.000699 |
| 18 | 0.000678 |
| 19 | 0.000695 |
| 20 | 0.000539 |
| 21 | 0.0029 |
| 22 | 0.0028 |

TABLE 1-continued

| Example | sEH IC$_{50}$ (μM) |
|---|---|
| 23 | 0.00275 |
| 24 | 0.00187 |
| 25 | 0.00276 |
| 26 | 0.00275 |
| 27 | 0.000803 |
| 28 | 0.000803 |
| 29 | 0.000803 |
| 30 | 0.000803 |
| 31 | 0.000758 |
| 32 | 0.000756 |
| 33 | 0.000906 |
| 34 | 0.000906 |
| 35 | 0.000916 |
| 36 | 0.000906 |
| 37 | 0.000929 |
| 38 | 0.000803 |
| 39 | 0.00275 |
| 40 | 0.00275 |
| 41 | 0.00275 |
| 42 | 0.0027 |
| 43 | 0.00274 |
| 44 | 0.00272 |
| 45 | 0.00267 |
| 46 | 0.000906 |
| 47 | 0.00269 |
| 48 | 0.00269 |
| 49 | 0.00268 |
| 50 | 0.00267 |
| 51 | 0.000994 |
| 52 | 0.000955 |
| 53 | 0.00102 |
| 54 | 0.000976 |
| 55 | 0.00105 |
| 56 | 0.00101 |
| 57 | 0.00113 |
| 58 | 0.00117 |
| 59 | 0.00115 |
| 60 | 0.0011 |
| 61 | 0.00118 |
| 62 | 0.00114 |
| 63 | 0.00121 |
| 64 | 0.00125 |
| 65 | 0.00119 |
| 66 | 0.00125 |
| 67 | 0.00121 |
| 68 | 0.00119 |
| 69 | 0.00261 |
| 70 | 0.00262 |
| 71 | 0.00256 |
| 72 | 0.00259 |
| 73 | 0.00259 |
| 74 | 0.00266 |
| 75 | 0.00255 |
| 76 | 0.00253 |
| 77 | 0.00249 |
| 78 | 0.00254 |
| 79 | 0.00254 |
| 80 | 0.00253 |
| 81 | 0.00236 |
| 82 | 0.00237 |
| 83 | 0.00237 |
| 84 | 0.00235 |
| 85 | 0.00244 |
| 86 | 0.00238 |
| 87 | 0.00241 |
| 88 | 0.00144 |
| 89 | 0.0014 |
| 90 | 0.00143 |
| 91 | 0.00142 |
| 92 | 0.00139 |
| 93 | 0.00131 |
| 94 | 0.0015 |
| 95 | 0.00151 |
| 96 | 0.00157 |
| 97 | 0.0016 |
| 98 | 0.00152 |
| 99 | 0.00153 |
| 100 | 0.0023 |
| 101 | 0.00228 |
| 102 | 0.00233 |
| 103 | 0.00232 |
| 104 | 0.00233 |
| 105 | 0.00233 |
| 106 | 0.00218 |
| 107 | 0.00226 |
| 108 | 0.00215 |
| 109 | 0.00216 |
| 110 | 0.00216 |
| 111 | 0.00223 |
| 112 | 0.00164 |
| 113 | 0.00167 |
| 114 | 0.00167 |
| 115 | 0.00164 |
| 116 | 0.0016 |
| 117 | 0.00164 |
| 118 | 0.00172 |
| 119 | 0.00168 |
| 120 | 0.0053 |
| 121 | 0.00168 |
| 122 | 0.00174 |
| 123 | 0.00169 |
| 124 | 0.00169 |
| 125 | 0.00168 |
| 126 | 0.00175 |
| 127 | 0.00173 |
| 128 | 0.00173 |
| 129 | 0.00173 |
| 130 | 0.00173 |
| 131 | 0.00213 |
| 132 | 0.00209 |
| 133 | 0.00214 |
| 134 | 0.00215 |
| 135 | 0.00214 |
| 136 | 0.00213 |
| 137 | 0.00176 |
| 138 | 0.00627 |
| 139 | 0.00285 |
| 140 | 0.00181 |
| 141 | 0.00186 |
| 142 | 0.00182 |
| 143 | 0.00185 |
| 144 | 0.00179 |
| 145 | 0.00188 |
| 146 | 0.00194 |
| 147 | 0.00196 |
| 148 | 0.00187 |
| 149 | 0.0082 |
| 150 | 0.00187 |
| 151 | 0.00197 |
| 152 | 0.00207 |
| 153 | 0.00256 |
| 154 | 0.00205 |
| 155 | 0.00199 |
| 156 | 0.002 |
| 157 | 0.00208 |
| 158 | 0.00204 |
| 159 | 0.00080 |
| 160 | 0.00141 |
| 161 | 0.00611 |
| 162 | 0.0122 |
| 163 | 0.0252 |
| 164 | 0.0114 |
| 165 | 0.00961 |
| 166 | 0.0213 |
| 167 | 0.0122 |
| 168 | 0.0779 |
| 169 | 0.00876 |
| 170 | 0.018 |
| 171 | 0.0158 |
| 172 | 0.0108 |
| 173 | 0.0334 |
| 174 | 0.0148 |
| 175 | 0.0204 |
| 176 | 0.0134 |
| 177 | 0.0911 |
| 178 | 0.0586 |

TABLE 1-continued

| Example | sEH IC$_{50}$ (μM) |
|---|---|
| 179 | 0.0241 |
| 180 | 0.00846 |
| 181 | 0.0521 |
| 182 | 0.0184 |
| 183 | 0.0188 |
| 184 | 0.115 |
| 185 | 0.0138 |
| 186 | 0.0337 |
| 187 | 0.0832 |
| 188 | 0.0159 |
| 189 | 0.0289 |
| 190 | >1 |
| 191 | 0.014 |
| 192 | 0.0353 |
| 193 | 0.0152 |
| 194 | 0.032 |
| 195 | 0.0736 |
| 196 | 0.0364 |
| 197 | 0.0495 |
| 198 | 0.0133 |
| 199 | 0.208 |
| 200 | 0.00257 |
| 201 | 0.00637 |
| 202 | 0.0133 |
| 203 | 0.0363 |
| 204 | 0.0188 |
| 205 | 0.0057 |
| 206 | 0.00524 |
| 207 | 0.00631 |
| 208 | 0.00967 |
| 209 | 0.00349 |
| 210 | 0.0524 |
| 211 | 0.0909 |

These data show that compounds of formula I exhibit a highly potent and selective sEH inhibitory activity.

The invention claimed is:

1. A compound selected from the group consisting of:
   5-[4-((R)-2-Hydroxy-3-methyl-butyryl)-piperazin-1-ylmethyl]-thiophene-2-carboxylic acid (2-methoxy-pyridin-4-ylmethyl)-amide;
   5-[4-(2-Hydroxy-propionyl)-piperazin-1-ylmethyl]-thiophene-2-carboxylic acid 2-trifluoromethoxy-benzylamide;
   5-[4-(2,4-Dimethyl-6-oxo-6H-pyran-3-carbonyl)-piperazin-1-ylmethyl]-thiophene-2-carboxylic acid 4-chloro-2-fluoro-benzylamide;
   5-[4-(1-Amino-cyclopropanecarbonyl)-piperazin-1-ylmethyl]-thiophene-2-carboxylic acid 2-trifluoromethoxy-benzylamide;
   5-[4-(2,6-Dimethyl-pyridin-4-yl)-piperazin-1-ylmethyl]-thiophene-2-carboxylic acid 2,4-dichloro-benzylamide;
   5-[4-(3,5-Dimethyl-1H-pyrazole-4-carbonyl)-piperazin-1-ylmethyl]-thiophene-2-carboxylic acid (2-methoxy-pyridin-4-ylmethyl)-amide;
   5-[4-(3,6-Difluoro-pyridine-2-carbonyl)-piperazin-1-ylmethyl]-thiophene-2-carboxylic acid (2-methoxy-pyridin-4-ylmethyl)-amide; and
   2-[4-(2-Dimethylamino-propionyl)-piperazin-1-ylmethyl]-thiazole-5-carboxylic acid 2,4-dichloro-benzylamide,
   or a stereoisomeric form thereof, or a physiologically tolerable salt of any of the foregoing.

2. A pharmaceutical composition comprising at least one compound of claim 1, a stereoisomeric form thereof or a mixture of stereoisomeric forms thereof in any ratio, or a physiologically tolerable salt of any of the foregoing, and a pharmaceutically acceptable carrier.

* * * * *